United States Patent [19]
Jacobson et al.

[11] Patent Number: 6,066,642
[45] Date of Patent: May 23, 2000

[54] DIHYDROPYRIDINE-, PYRIDINE-, BENZOPYRAN-4-ONE- AND TRIAZOLOQUINAZOLINE DERIVATIVE, THEIR PREPARATION AND THEIR USE AS ADENOSINE RECEPTOR ANTAGONISTS

[75] Inventors: Kenneth A. Jacobson, Silver Spring, Md.; Ji-Long Jiang, North York, Canada; Yong-Chul Kim, Rockville, Md.; Yishai Karton, Ness-Ziona, Israel; Albert M. Van Rhee, Durham, N.C.

[73] Assignee: The United States of America as represented by the Department of Health and Human Services, Washington, D.C.

[21] Appl. No.: 09/117,598

[22] PCT Filed: Jan. 29, 1997

[86] PCT No.: PCT/US97/01252

§ 371 Date: Dec. 7, 1998

§ 102(e) Date: Dec. 7, 1998

[87] PCT Pub. No.: WO97/27177

PCT Pub. Date: Jul. 31, 1997

Related U.S. Application Data

[60] Provisional application No. 60/010,737, Jan. 29, 1996, and provisional application No. 60/021,191, Jul. 3, 1996.

[51] Int. Cl.[7] .......................... A01N 43/54; A01N 43/16; C07D 211/40; C07D 311/04; C07D 471/00
[52] U.S. Cl. .......................... 514/267; 514/278; 514/299; 514/311; 514/327; 514/329; 514/330; 514/345; 514/348; 514/354; 514/355; 514/456; 544/251; 546/102; 546/207; 546/220; 546/222; 546/218; 546/223; 546/224; 546/229; 546/242; 546/243; 546/244; 546/248; 546/246; 546/247; 549/401; 549/402; 549/403
[58] Field of Search ..................... 546/192, 207, 546/220, 222, 218, 223, 224, 229, 242, 243, 244, 248, 246, 247; 544/251; 549/401, 402, 403; 514/267, 278, 299, 311, 327, 329, 330, 345, 348, 354, 355, 456

[56] References Cited

U.S. PATENT DOCUMENTS

| | | | |
|---|---|---|---|
| 3,932,645 | 1/1976 | Meyer et al. | 424/266 |
| 4,048,171 | 9/1977 | Bossert et al. | 260/256.4 |
| 4,380,547 | 4/1983 | Materne | 424/270 |
| 4,532,248 | 7/1985 | Franckowiak et al. | 514/302 |
| 5,502,064 | 3/1996 | Junge et al. | 514/336 |

FOREIGN PATENT DOCUMENTS

| | | |
|---|---|---|
| 0 161 877 | 11/1985 | European Pat. Off. |
| 0 197 488 | 4/1986 | European Pat. Off. |
| 0 212 340 | 3/1987 | European Pat. Off. |
| 0 217 530 | 4/1987 | European Pat. Off. |
| 0 239 186 | 9/1987 | European Pat. Off. |
| 0 387 070 | 9/1990 | European Pat. Off. |
| 2 228 377 | 1/1974 | Germany . |

OTHER PUBLICATIONS

Ali et al., "$A_3$ Adenosine Receptor in the Airways of Allergic Rabbits," *Experimental Biology*, (1997).
Ares et al., "The Binding of Flavonoids to Adenosine Receptors." *Abstracts of Papers of the American Chemical Society*, 209, 190–MEDI, (1995).
Carruthers et al., "Adenosine $A_3$ Receptors: Two in One Won't Go," *Trends in Pharmacological Sciences*, 14 8, 290–291 (1993).
Eynde et al., "Old Reagents, New Results: Aromitization of Hantzsch 1,4–Dihydropyridines with Manganese Dioxide and 2,3–Dichloro–5,6–dicyano–1,4–benzoquinone," *Tetrahedron*, 51 23, 6511–6516 (1995).
Francis et al., "Structure–Activity Profile of a Series of Novel Triazoloquinazoline Adenosine Antagonists," *J. Med. Chem.*, 31, 1014–1020 (1988).
Hu et al., "Interaction of Dihydropyridine Calcium Channel Agonists and Antagonists with Adenosine Receptors," *Pharmacology and Technology*, 61, 121–125 (1987).
Ismail et al., "Effect of Calcium Channel Antagonists in Modifying the Inhibitory Influence of Adenosine on Insulin Secretion." *Arzneimittel–Forschung/Drug Research*, 45 8, 865–868 (1995).
Jacobson et al., "$A_3$–Adenosine Receptors: Design of Selective Ligands and Therapeutic Prospects," *Drugs of the Future*, 20 7, 686–699 (1995).
Jacobson et al., "$A_3$ Adenosine Receptors: Novel Ligands and Paradoxical Effects," *Trends Pharmcol. Sci.*, 19, 184–191 (1998).
Jacobson et al., "Pharmacological Characterization of Novel $A_3$ Adenosine Receptor–Selective Antagonists," *Neuropharmacology*, 36, 1157–1165 (1997).
Jiang et al., "6–Phenyl–1,4–dihydropyridine Derivatives as Potent and Selective $A_3$ Adenosine Receptor Antagonist," *J. Med. Chem.*, 39, 4667–4675 (1996).
Jiang et al., "Structure Activity Relationships of 4–Phenylethynyl–6–Phenyl–1, 4–Dihydropyridines as Highly Selective $A_3$ Adenosine Receptor Antagonists," *J. Med. Chem.*, 40, 2596–2608 (1997).
Marangos, "Calcium Antagonists and the Brain Adenosine System," *Chemical Abstracts*, 105: 127265g (1986).

(List continued on next page.)

*Primary Examiner*—John Kight
*Assistant Examiner*—Raymond Covington
*Attorney, Agent, or Firm*—Leydig, Voit & Mayer

[57] ABSTRACT

The present invention provides certain novel compounds, compositions, and a method of treating a mammal by blocking its adenosine receptors comprising administering at least one compound of the present invention. Examples of the present inventive compounds include certain flavonoids of formulae (I) and (II), wherein $R_1$ to $R_4$ are as defined in the description, and M is —CH(OH)—CH($R_2$)— or —C(OH)=C($R_2$)— and $R_1$, $R_2$ are as defined in the description; or dihydropyridines of formula (III), wherein $R_2$ to $R_6$ are as defined in the description; or pyridines of formula (IV), wherein $R_2$ to $R_6$ are as defined in the description, or triazoloquinazolines of formula (V), wherein $R_1$ and $R_2$ are as defined in the description; and their derivatives, or pharmaceutically acceptable salts thereof.

33 Claims, 17 Drawing Sheets

OTHER PUBLICATIONS

Meade, et al., "In Vivo Role of the Adenosine $A_3$ Receptor: $N^6$2–(4–Aminophenyl)ethyladenosine Induces Bronchospasm in BDE Rats by a Neurally Mediated Mechanism involving Cells resembling Mast Cells," *Journal of Pharmacology and Experimental Therapeutics*, 279 5, 1148–1156, 1990.

Mustafa et al., "Adenosine–Induced Bronchoconstriction and Contraction of Airway Smooth Muscle from Allergic Rabbits with Late–Phase Airway Obstruction: Evidence for an Inducible Adenosine $A_1$ Receptor[1]," *Journal of Pharmacology and Experimental Therapeutics*, 268 3, 1328–1334 (1994).

Murphy et al., "Adenosine Receptor Binding and Specific Receptors for Calcium Channel Drugs," *Chemical Abstracts*, 99: 187500x (1983).

Pfister, "Rapid, High–Yield Oxidation of Hantzsch–Type 1,4–Dihydropyridines with Ceric Ammonium Nitrate," *Synthesis*, 8, 689–690 (1990).

Van Rhee et al., "Interaction of 1,4–Dihydropyridine and Pyridine Derivatives with Adenosine Receptors: Selectivity for $A_3$ Receptors," *Journal of Medicinal Chemistry*, 39 15, 2980–2989 (1996).

Van Rhee et al., "Tetrahydrobenzothiophenone Derivatives as a Novel Class of Adenosine Receptor Antagonists," *Journal of Medicinal Chemistry*, 39 2, 398–406 (1996).

Yao, Y. et al., "Adenosine $A_3$ Receptor Agonists Proteet HL–60 and U–937 Cells from Apoptosis Induced by $A_3$ Antagonists," *Biochem. Biophys. Res. Comm.*, 232, 317–322 (1997).

DIHYDROPYRIDINE-, PYRIDINE-, BENZOPYRAN-4-ONE- AND TRIAZOLOQUINAZOLINE DERIVATIVE, THEIR PREPARATION AND THEIR USE AS ADENOSINE RECEPTOR ANTAGONISTS

CROSS-REFERENCE TO RELATED APPLICATIONS

This is a continuation-in-part application of U.S. provisional patent application Serial No. 60/010,737, filed Jan. 29, 1996, and Serial No. 60/021,191, filed July 3, 1996, the disclosures of which are incorporated herein in their entirety by reference.

TECHNICAL FIELD OF THE INVENTION

The present invention relates to adenosine receptor antagonists, pharmaceutical compositions, and methods of selectively blocking adenosine receptors in a mammal. The present invention also relates to methods of treating various medical disorders with adenosine receptor antagonists.

BACKGROUND OF THE INVENTION

The use of caffeine and other alkylxanthines as physiological stimulants is well known. The principle mechanism by which caffeine and other alkylxanthines act as physiological stimulants is by blocking the effects of the ubiquitous neuromodulator adenosine. Daly, "Mechanism of action of caffeine", in *Caffeine, Coffee and Health*, (S. Garattini, ed), Chapter 4, pp. 97–150 (1993). Adenosine is produced locally in response to increased activity or stress to the system. This feedback mechanism allows the organ to compensate for the stress by decreasing energy demand (depressant activity) and increasing oxygen supply (e.g., by vasodilation). Bruns, *Nucleosides & Nucleotides*, 10, 931–944 (1991).

Adenosine plays several key physiological roles. In addition to its role in intermediary metabolism, adenosine displays a number of receptor-mediated physiological actions, including dilation of coronary vessels, inhibition of platelet aggregation, and inhibition of lipolysis. Bruns et al., *Proc. Nat. Acad. Sci. U.S.A.*, 77, 5547–5551 (1980). Adenosine receptors, belonging to the superfamily of the G protein-coupled receptors, are generally divided into two major subclasses, $A_1$ and $A_2$, on the basis of the differential affinities of a number of adenosine receptor agonists and antagonists for the receptors, their primary structures, and the secondary messenger systems to which they couple. Thus, $A_2$ receptors, which can be further subdivided into $A_{2a}$ and $A_{2b}$, stimulate adenylate cyclase, whereas $A_1$ receptors may couple to a variety of secondary messenger systems, including those involved in the inhibition of adenylate cyclase, the inhibition or stimulation of phosphoinositol turnover, the activation of guanylate cyclase, the activation of potassium influx, and the inhibition of calcium influx (van Galen et al., *Med. Res. Rev.*, 12, 423–471 (1992); Jacobson et al., *J. Med. Chem.*, 35, 407–422 (1992)).

Recently, a novel adenosine receptor was identified on the basis of its primary structure and cloned from rat brain (Zhou et al., *Proc. Natl. Acad. Sci. U.S.A.*, 89, 7432–7436 (1992)) and rat testes (Meyerhof et al., *FEBS Lett.*, 284, 155–160 (1991)). The putative transmembrane domains of the novel adenosine receptor, which has been designated the $A_3$ receptor, show 58% identity with the canine $A_1$ receptor and 57% with the canine $A_{2a}$ receptor. Like the $A_1$ receptor, the $A_3$ receptor is negatively coupled to adenylate cyclase (Zhou et al.).

The distribution of the $A_3$ receptor is found primarily in the central nervous system (CNS) (Zhou et al.), brain, testes (Meyerhof et al.), and immune system, where it appears to be involved in the modulation of release from mast cells of mediators of the immediate hypersensitivity reaction (Ramkumar et al., *J. Biol. Chem.*, 268, 16887–16890 (1993)). It is believed that $A_3$-selective compounds will have utility in the therapeutic and/or prophylactic treatment of cardiac disease, infertility, kidney disease, and CNS disorders.

It is further believed that selective $A_3$-adenosine receptor antagonists should serve as cerebroprotective, anti-asthmatic, or anti-inflammatory agents. Beaven et al., *Trends Pharmacol. Sci.*, 15, 13–4 (1994); Jacobson et al., *Drugs of the Future*, 20, 689–699 (1995); von Lubitz et al., *Eur. J. Pharmacol.*, 275, 23–29 (1995).

Copending U.S. patent applications Ser. No. 08/274,628, filed Jul. 13, 1994, and Ser. No. 08/396,111, filed Feb. 28, 1995, disclose certain $A_3$ selective agonists, particularly $N^6$-benzyladenosine-5'-uronamide and related substituted compounds, xanthine riboside derivatives, pharmaceutical compositions comprising such compounds, and the method of use of such compounds.

The foregoing indicates that there is a need for antagonists for adenosine receptors. The present invention seeks to provide such compounds, as well as methods of using these compounds to selectively block adenosine receptors in mammals, and pharmaceutical compositions comprising such compounds. These and other objects and advantages of the present invention, as well as additional inventive features, will be apparent from the description of the invention provided herein.

SUMMARY OF THE INVENTION

The present invention provides a compound of the formula I

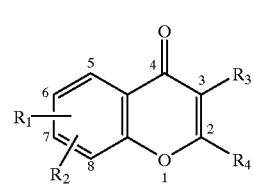

wherein $R_1$ and $R_3$ are selected from the group consisting of hydrogen, hydroxy, $C_1$–$C_6$ alkyloxy, and $C_1$–$C_6$ alkylcarbonyloxy; $R_2$ is selected from the group consisting It is further believed that selective $A_3$-adenosine receptor antagonists should serve as cerebroprotective, anti-asthmatic, or anti-inflammatory agents. Beaven et al., *Trends Pharmacol. Sci.*, 15, 13–4 (1994); Jacobson et al., *Drugs of the Future*, 20, 689–699 (1995); von Lubitz et al., *Eur. J. Pharmacol.*, 275, 23–29 (1995).

Certain documents provide the relevant background art of the present invention and are discussed herein below.

DE-A-20 05 116, DE-A-21 17 571, and EP-A-0 239 186, EP-A-0 042 089, and EP-A-0 595 166 disclose certain dihydropyridine derivatives wherein the substituents at the 2- and 6-positions of the dihydropyridine moiety are both alkyl. These compounds are said to be useful in the treatment of cardiovascular diseases.

*Synthesis*, 8, 689–690 (1990), discloses a method of oxidation of 1,4-dihydropyridines with ceric ammonium nitrate. *Tetrahedron*, 51, 6511–6516 (1995), discloses the aromatization of 1,4-dihydropyridines with manganese dioxide and 2,3-dichloro-5,6-dicyano-1,4-benzoquinone.

DE-A-22 28 377 discloses certain generic dihydropyridine derivatives effective as cardiovascular agents wherein the substituents at the dihydropyridine 2- and 6-positions are selected from the group consisting of hydrogen, alkyl, and aryl. However, this document does not disclose a subgenus or specific compounds wherein the 2-substituent is alkyl and the 6-substituent is aryl.

EP-A-0 071 819 discloses certain generic dihydropyridine derivatives useful in increasing the influx of $Ca^{2+}$ into cells wherein the substituents at the dihydropyridine 2- and 6-positions can be alkyl or aryl. However, this document does not disclose a subgenus or specific compounds wherein the 2-substituent is alkyl and the 6-substituent is aryl.

EP-A-0 197 488 discloses certain dihydropyridine derivatives useful in the treatment and prevention of cardiopathy and antihypertensive and coronary vasodilating action, wherein the dihydropyridyl 2-substituent is methyl and the 6-substituent is methyl or 4-p-(fluorobenzyl)-1-piperidylmethyl. EP-A-0 212 340 discloses certain dihydropyridine derivatives having antihypertensive activity, wherein the 2-substituent is an alkyl and the 6-substituent is a methyl substituted with halo, ammonium, or phosphonium group.

EP-A-0 217 530 discloses certain dihydropyridine derivatives which are said to be peripheral and cerebral vasodilators possessing bradycardiac activity. The substituents at the dihydropyridyl 2- and 6-positions are selected from the group consisting of hydrogen, methyl, and amino groups.

*Chemical Abstracts,* 99(23), 187500x (1983), discloses that a calcium channel antagonist, nifedipine, was potent in reducing the binding of adenosine receptor specific [$^3$H]cyclohexyladenosine and [$^3$H]1,3-diethyl-8-phenylxanthine. The document also discloses that other calcium antagonists, diltiazem and verapamil, had negligible effects on adenosine receptor binding.

*Chemical Abstracts,* 105(15), 127265g (1986), discloses that dihydropyridine $Ca^{2+}$ antagonists interacted with brain adenosine receptor and uptake sites in canine brain in vitro. *Arzneimittel Forsch./Drug Res.,* 45(II)(8), 865–868 (1995), discloses that calcium channel antagonists, nifedipine and verapamil, may not interact with adenosine receptors which mediate adenosine's inhibitory effect on insulin secretion from pancreatic islets.

*J. Med. Chem.,* 31, 1014–1020 (1988), discloses certain triazoloquinazoline derivatives as $A_1$ and $A_2$ adenosine receptor antagonists. EP-A-0 387 070 discloses certain substituted pyridine derivatives which are said to possess a reducing effect of reperfusion injury and cardioprotective effect such as an improving or enhancing effect on the depressed cardiac metabolism.

*J. Med. Chem.,* 39, 2980–2989 (1996) ("van Rhee et al."), and *J. Med. Chem.,* 39, 4667–4675 (1996) ("Jiang et al."), include as co-authors some of the inventors of the invention described in this application and report some of the work discussed in this application. Thus, van Rhee et al. discusses the selectivity and interaction of certain 1,4-dihydropyridine and pyridine derivatives with $A_3$ adenosine receptor sites. Jiang et al. discloses that 6-phenyl-1,4-dihydropyridine derivatives are potent and selective $A_3$ adenosine receptor antagonists.

Copending U.S. patent applications Ser. No. 08/274,628, filed Jul. 13, 1994, and Ser. No. 08/396,111, filed Feb. 28, 1995, now U.S. Pat. No. 5,688,774, disclose certain $A_3$ selective agonists, particularly $N^6$-benzyladenosine-5'-uronamide and related substituted compounds, xanthine riboside derivatives, pharmaceutical compositions comprising such compounds, and the method of using such compounds.

The foregoing indicates that there is a need for antagonists for adenosine receptors. The present invention seeks to provide such compounds, as well as methods of using these compounds to selectively block adenosine receptors in mammals, and pharmaceutical compositions comprising such compounds. These and other objects and advantages of the present invention, as well as additional inventive features, will be apparent from the description of the invention provided herein.

SUMMARY OF THE INVENTION

The present invention provides a compound of the formula I

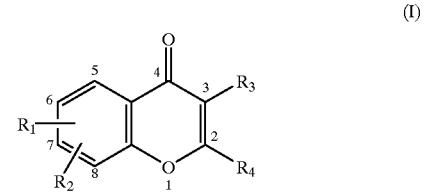

wherein $R_1$ and $R_3$ are selected from the group consisting of hydrogen, hydroxy, $C_1$–$C_6$ alkyloxy, and $C_1$–$C_6$ alkylcarbonyloxy; $R_2$ is selected from the group consisting of hydrogen, hydroxy, $C_1$–$C_6$ alkyloxy, and $C_2$–$C_6$ alkenyloxy, said alkenyloxy together with the carbon atom of the phenyl ring forming an oxygen heterocycle; and $R_4$ is selected from the group consisting of phenyl, styryl, phenylbutadienyl, phenylacetylenyl, and —CH=N-phenyl, and substituted phenyl, styryl, phenylacetylenyl, and phenylbutadienyl, wherein the phenyl ring is substituted with 1 to 5 $C_1$–$C_6$ alkyloxy groups; with the provisos that when $R_3$ is hydrogen, $R_1$ and $R_2$ are neither hydroxy nor alkyloxy; when $R_1$, $R_2$, and $R_3$ are hydrogen, $R_4$ is neither phenyl nor alkyloxyphenyl; when $R_3$ is hydrogen and $R_4$ is phenyl, neither $R_1$ nor $R_2$ is alkylcarbonyloxy; and when $R_3$ is hydroxy or alkyloxy, $R_1$ and $R_2$ are not dihydroxy.

The present invention further provides a compound of the formula II

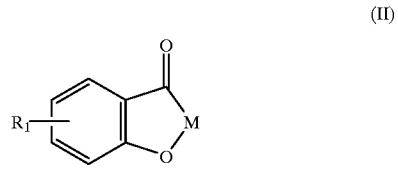

wherein $R_1$ is selected from the group consisting of hydroxyl and $C_1$–$C_6$ alkoxy, and M is a divalent radical selected from the group consisting of —CH(OH)—CH($R_2$)— and —C(OH)=C($R_2$)—, wherein $R_2$ is selected from the group consisting of styryl and phenylacetylenyl.

The present invention provides a compound of the formula III (III)

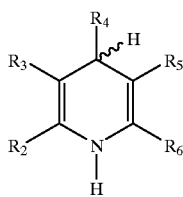

or a pharmaceutically acceptable salt thereof, wherein $R_2$ is a $C_1$–$C_6$ alkyl; $R_6$ is selected from the group consisting $C_1$–$C_6$ alkyl, $C_1$–$C_6$ haloalkyl, and phenyl which may be further substituted with $C_1$–$C_6$ alkyl, halo, nitro, furyl, or thienyl; $R_3$ is selected from the group consisting of $C_1$–$C_6$ alkyl, $C_1$–$C_6$ alkyloxycarbonyl, aryl $C_1$–$C_6$ alkyloxycarbonyl, $C_1$–$C_6$ alkylthiocarbonyl, $C_1$–$C_6$ alkylaminocarbonyl, and $C_1$–$C_6$ alkyloxy $C_1$–$C_6$ alkylcarbonyl, or $R_3$ together with $R_2$ forms a ring having 2–4 methylene groups, and $C_1$–$C_6$ alkenyloxycarbonyl; $R_4$ is selected from the group consisting of $C_1$–$C_6$ alkyl, aryl $C_2$–$C_6$ alkenyl, $C_1$–$C_6$ alkylamino, $C_1$–$C_6$ alkyl silyl $C_1$–$C_6$ alkyloxy, aryl, heterocyclic, aryl $C_1$–$C_6$ alkyl, phenylacetylenyl which may be further substituted with nitro, $C_1$–$C_6$ alkyl, hydroxy, halo, amino, carboxy, $C_1$–$C_6$ alkoxy, $C_1$–$C_6$ haloalkyl, or $C_1$–$C_6$ alkylamino, and styryl whose phenyl ring may be further substituted with one or more substituents selected from the group consisting of halo, nitro, amino, hydroxy, $C_1$–$C_6$ alkyl, cyano, $C_1$–$C_6$ alkyloxy, $C_1$–$C_6$ alkyloxycarbonyl, $C_1$–$C_6$ alkylcarbonyl, hydroxy $C_1$–$C_6$ alkyl, $C_1$–$C_6$ haloalkyl, carboxy, aminocarbonyl, $C_1$–$C_6$ alkylamino, amino $C_1$–$C_6$ alkyl, and $C_1$–$C_6$ dialkylamino; and $R_5$ is selected from the group consisting of $C_1$–$C_6$ alkyloxycarbonyl, aryl $C_1$–$C_6$ alkyloxycarbonyl, $C_1$–$C_6$ alkyloxy $C_1$–$C_6$ alkyloxycarbonyl, aryloxy $C_1$–$C_6$ alkyloxycarbonyl, $C_1$–$C_6$ alkyloxycarbonyl, aryl $C_1$–$C_6$ alkyloxy $C_1$–$C_6$ alkyloxycarbonyl, silyl $C_1$–$C_6$ alkyloxycarbonyl, $C_1$–$C_6$ alkylthio, hydroxy, and $C_1$–$C_6$ alkylamino, wherein said aryl may be further substituted with $C_1$–$C_6$ alkyl, $C_1$–$C_6$ halo alkyl, trifluoromethyl, halo, nitro, $C_1$–$C_6$ amino alkyl, $C_1$–$C_6$ aminoalkylamino, or $C_1$–$C_6$ amino alkylamino carbonyl; wherein said aryl is phenyl or naphthyl.

The present invention further provides a compound of the formula IV (IV)

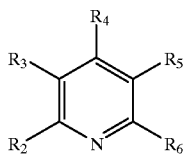

or pharmaceutically acceptable salts thereof, wherein $R_2$ is selected from the group consisting of hydrogen and $C_1$–$C_6$ alkyl; $R_3$ is selected from the group consisting of hydrogen and $C_1$–$C_6$ alkyloxycarbonyl; $R_4$ is selected from the group consisting of $C_1$–$C_6$ alkyl, phenyl $C_2$–$C_6$ alkenyl, phenyl $C_2$–$C_6$ alkynyl, aryl, and aryl substituted with one or more substituents selected from the group consisting of nitro and $C_1$–$C_6$ alkyloxy; $R_5$ is selected from the group consisting of hydrogen, $C_1$–$C_6$ alkyloxycarbonyl, and aryl $C_1$–$C_6$ alkyloxy carbonyl; $R_6$ is selected from the group consisting of hydrogen, aryl, and $C_1$–$C_6$ alkyl; with the proviso that when $R_2$=$R_3$=$R_5$=$R_6$=hydrogen, $R_4$ is not alkyl.

The present invention further provides a compound of the formula V (V)

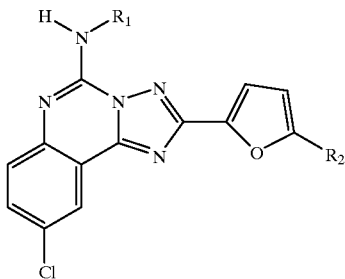

wherein $R_1$ is selected from the group consisting of $C_1$–$C_6$ alkylcarbonyl, $C_1$–$C_6$ alkyloxycarbonyl, amino $C_1$–$C_6$ alkylcarbonyl, and arylcarbonyl wherein the aryl may be further substituted with halo, nitro, hydroxy, amino or cyano; and $R_2$ is hydrogen or halogen.

The present invention further provides pharmaceutical compositions comprising any of the aforesaid compounds and a method of treating a mammal comprising selectively blocking one or more of the adenosine receptors of the mammal by administering to the mammal at least one compound of formulas I–V.

BRIEF DESCRIPTION OF THE DRAWINGS

In FIGS. 11A–D, for each set of curves, control (--), antagonist alone (Δ), or antagonist in the presence of 10 nM (°) or 1 μM (•) Cl-IB-MECA are shown.

FIG. 11B depicts the number of living HL-60 cells (vertical axis) as a function of the concentration (horizontal axis) of the A₃ adenosine receptor antagonist and low concentration of Cl-IB-MECA. The antagonist was compound L-249313(6-carboxymethyl-5,9-dihydro-9-methyl-2-phenyl-[1,2,4]triazolo[5,1-a][2,7]-naphthyridine).

FIG. 11C depicts the number of living U-937 cells (vertical axis) as a function of the concentration (horizontal axis) of the A₃ adenosine receptor antagonist and a low concentration of Cl-IB-MECA. The antagonist was compound 101.

FIG. 11D depicts the number of living U-937 cells (vertical axis) as a function of the concentration (horizontal axis) of the A₃ adenosine receptor antagonist and a low concentration of Cl-IB-MECA. The antagonist was compound L-249313.

DETAILED DESCRIPTION OF THE PREFERRED EMBODIMENTS

Figure 1:
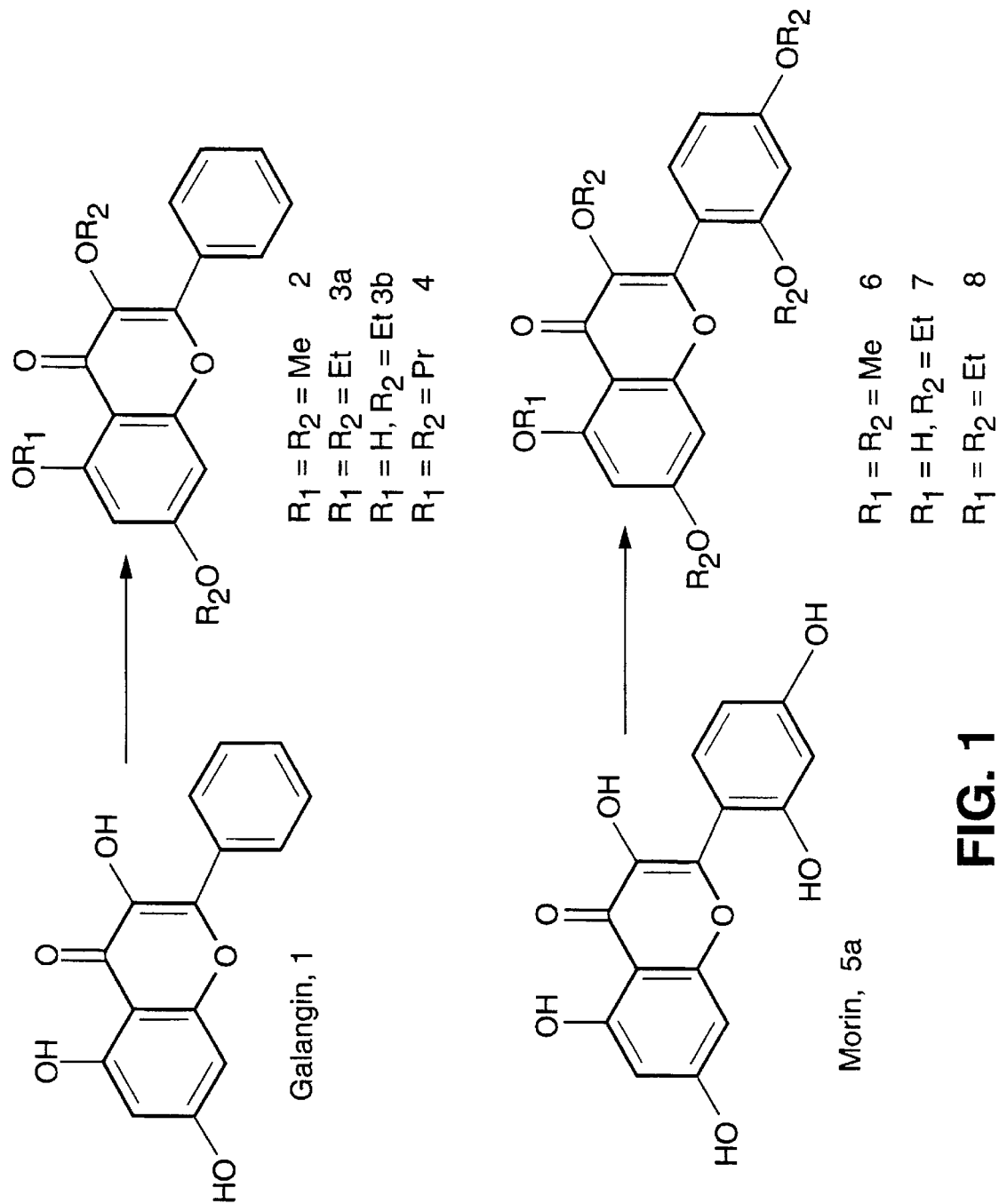
FIG. 1 depicts a method of synthesis of alkylated derivatives of galangin and morin. Alkyl iodide was used as the alkylating agent for the preparation of 2, 3a, 3b, 4, and 6. Ethyl bromide was used as the alkylating agent for the preparation of 7, and alkyl sulfate was used as the alkylating agent for the preparation of 8.

The present invention may be best understood with reference to the accompanying drawings and to the following detailed description of the preferred embodiments.

The present invention provides certain derivatives of flavonoids, dihydropyridines, pyridines, and triazoloquinazolines, suitable for blocking one or more of the adenosine receptors of a mammal such as human, as set forth herebelow in greater detail.

The present invention provides a compound of the formula I

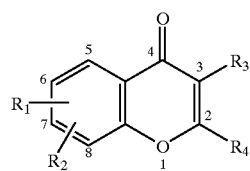

(I)

wherein $R_1$ and $R_3$ are selected from the group consisting of hydrogen, hydroxy, $C_1$–$C_6$ alkyloxy, and $C_1$–$C_6$ alkylcarbonyloxy; $R_2$ is selected from the group consisting of hydrogen, hydroxy, $C_1$–C, alkyloxy, and $C_2$–$C_6$ alkenyloxy, said alkenyloxy together with the carbon atom of the phenyl ring forming an oxygen heterocycle; and $R_4$ is selected from the group consisting of phenyl, styryl, phenylbutadienyl, phenylacetylenyl, and —CH=N-phenyl, and substituted phenyl, styryl, phenylacetylenyl, and phenylbutadienyl, wherein the phenyl ring is substituted with 1 to 5 $C_1$–$C_6$ alkyloxy groups; with the provisos that when $R_3$ is hydrogen, $R_1$ and $R_2$ are neither hydroxy nor alkoxy; when $R_1$, $R_2$, and $R_3$ are hydrogen, $R_4$ is neither phenyl nor alkyloxyphenyl; when R3 is hydrogen and $R_4$ is phenyl, neither $R_1$ nor $R_2$ is alkylcarbonyloxy; and when $R_3$ is hydroxy or alkyloxy, $R_1$ and $R_2$ are not dihydroxy.

Particular embodiments include a compound of formula I wherein (a) $R_4$ is phenyl, (b) $R_4$ is phenyl and $R_3$ is a $C_1$–$C_3$ alkyloxy, (c) $R_4$ is phenyl, $R_3$ is a $C_1$–$C_3$ alkyloxy, and $R_1$ and $R_2$ are 5,7-di ($C_1$–$C_3$ alkyloxy), (d) $R_4$ is a 2,4-di($C_1$–$C_3$ alkyloxy)phenyl, (e) $R_3$ is a $C_1$–$C_3$ alkyloxy and $R_4$ is a 2,4-di($C_1$–$C_3$ alkyloxy)phenyl, (f) $R_3$ is a $C_1$–$C_3$ alkyloxy, $R_4$ is a 2,4-di($C_1$–$C_3$ alkyloxy)phenyl, and $R_1$ and $R_2$ are the same and are selected from the group consisting of methoxy and ethoxy, (g) $R_1$ is 5-hydroxy and $R_2$ is one of methoxy and ethoxy, (h) $R_4$ is phenylacetylenyl, (i) $R_4$ is phenylacetylenyl and $R_3$ is hydroxy, and (j) $R_4$ is phenylacetylenyl, $R_3$ is hydroxy, and one of $R_1$ and $R_2$ is methoxy.

The present invention further provides a compound of formula I, wherein the compound is a 4-($C_1$–$C_6$ alkyloxy)-7-styrylvisnagin. Examples of such compounds include 4-methoxy-7-trans-styrylvisnagin, 4-ethoxy-7-trans-styrylvisnagin, and 4-propoxy-7-trans-styrylvisnagin.

Other particular embodiments include compounds of formula I, wherein the compound is a $C_1$–$C_6$ alkyloxy-7-phenylbutadienylvisnagin. Examples of such compounds include 4-methoxy-7-phenylbutadienylvisnagin and 4-ethoxy-7-phenylbutadienylvisnagin.

The present invention further provides a compound of formula I, wherein the compound is a $C_1$–$C_6$ alkyloxy-7-(CH=N-phenyl)visnagin. An example of such compound is 4-methoxy-7-(CH=N-phenyl)visnagin.

The present invention further provides a compound of formula I, wherein the compound is selected from the group consisting of 3,5,7-triacetoxyflavone, 3,5,7-trimethoxyflavone, 3,5,7-triethoxyflavone, 3,7-diethoxy-5-hydroxyflavone, 3,5,7-tripropoxyflavone, 3,4',5,7-tetramethoxyflavone, 2',3,4',7-tetraethoxy-5-hydroxyflavone, 2',3,4',5,7-pentamethoxyflavone, 2',3,4',5,7-pentaethoxyflavone, hexamethylmyricetin, and 3-hydroxy-4'-phenylacetylenyl-6-methoxyflavone.

The present invention further provides a compound of the formula II

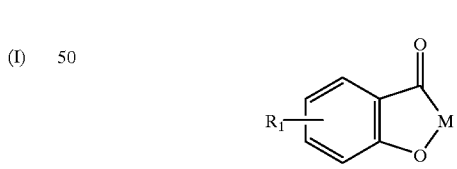

(II)

wherein $R_1$ is selected from the group consisting of hydroxyl and $C_1$–$C_6$ alkoxy, and M is a divalent radical selected from the group consisting of —CH(OH)—CH($R_2$)— and —C(OH)=C($R_2$)—, wherein $R_2$ is selected from the group consisting of styryl and phenylacetylenyl.

Examples of compounds of formula II include 2-phenylacetylenyl-3-hydroxy-6-methoxyflavone, trans-2-styryl-3-hydroxy-6-methoxyflavone, and trans-2-phenylacetylenyl-3-hydroxy-6-methoxyflavone.

The present invention further provides a compound of the formula III

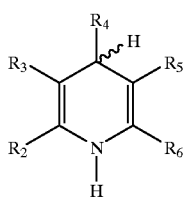

(III)

or a pharmaceutically acceptable salt thereof, wherein $R_2$ is a $C_1$–$C_6$ alkyl; $R_6$ is selected from the group consisting $C_1$–$C_6$ alkyl, $C_1$–$C_6$ haloalkyl, and phenyl which may be further substituted with $C_1$–$C_6$ alkyl, halo, nitro, furyl, or thienyl; $R_3$ is selected from the group consisting of $C_1$–$C_6$ alkyl, $C_1$–$C_6$ alkyloxycarbonyl, aryl $C_1$–$C_6$ alkyloxycarbonyl, $C_1$–$C_6$ alkylthiocarbonyl, $C_1$–$C_6$ alkylaminocarbonyl, and $C_1$–$C_6$ alkyloxy $C_1$–$C_6$ alkylcarbonyl, or $R_3$ together with $R_2$ forms a ring having 2–4 methylene groups, and $C_1$–$C_6$ alkenyloxycarbonyl; $R_4$ is selected from the group consisting of $C_1$–$C_6$ alkyl, aryl $C_2$–$C_6$ alkenyl, $C_1$–$C_6$ alkylamino, $C_1$–$C_6$ alkyl silyl $C_1$–$C_6$ alkyloxy, aryl, heterocyclic, aryl $C_1$–$C_6$ alkyl, phenylacetylenyl which may be further substituted with nitro, $C_1$–$C_6$ alkyl, hydroxy, halo, amino, carboxy, $C_1$–$C_6$ alkoxy, $C_1$–$C_6$ haloalkyl, or $C_1$–$C_6$ alkylamino, and styryl whose phenyl ring may be further substituted with one or more substituents selected from the group consisting of halo, nitro, amino, hydroxy, $C_1$–$C_6$ alkyl, cyano, $C_1$–$C_6$ alkyloxy, $C_1$–$C_6$ alkyloxycarbonyl, $C_1$–$C_6$ alkylcarbonyl, hydroxy $C_1$–$C_6$ alkyl, $C_1$–$C_6$ haloalkyl, carboxy, aminocarbonyl, $C_1$–$C_6$ alkylamino, amino $C_1$–$C_6$ alkyl, and $C_1$–$C_6$ dialkylamino; and $R_5$ is selected from the group consisting of $C_1$–$C_6$ alkyloxycarbonyl, aryl $C_1$–$C_6$ alkyloxycarbonyl, $C_1$–$C_6$ alkyloxy $C_1$–$C_6$ alkyloxycarbonyl, aryloxy $C_1$–$C_6$ alkyloxycarbonyl, $C_1$–$C_6$ alkyloxycarbonyl, aryl $C_1$–$C_6$ alkyloxy $C_1$–$C_6$ alkyloxycarbonyl, silyl $C_1$–$C_6$ alkyloxycarbonyl, $C_1$–$C_6$ alkylthio, hydroxy, and $C_1$–$C_6$ alkylamino, wherein the aryl moiety of said $R_5$ may be further substituted with $C_1$–$C_6$ alkyl, $C_1$–$C_6$ halo alkyl, trifluoromethyl, halo, nitro, $C_1$–$C_6$amino alkyl, $C_1$–$C_6$ aminoalkylamino, or $C_1$–$C_6$ amino alkylamino carbonyl; wherein the aryl moiety of said $R_3$, $R_4$, $R_5$, and $R_6$ is independently phenyl or naphthyl.

Particular embodiments include compounds of formula III, wherein (a) $R_2$ is methyl, (b) $R_2$ is methyl and $R_3$ is selected from the group consisting of methoxycarbonyl and ethoxycarbonyl, (c) $R_2$ is methyl, $R_3$ is selected from the group consisting of methoxycarbonyl and ethoxycarbonyl, and $R_6$ is selected from the group consisting of $C_1$–$C_4$ alkyl and phenyl, (d) $R_2$ is methyl, $R_3$ is selected from the group consisting of methoxycarbonyl and ethoxycarbonyl, $R_6$ is selected from the group consisting of $C_1$–$C_4$ alkyl and phenyl, and $R_4$ is selected from the group consisting of $C_1$–$C_3$ alkyl, (e) $R_2$ is methyl, $R_3$ is selected from the group consisting of methoxycarbonyl and ethoxycarbonyl, $R_6$ is selected from the group consisting of $C_1$–$C_4$ alkyl and phenyl, $R_4$ is selected from the group consisting of $C_1$–$C_3$ alkyl, and $R_5$ is selected from the group consisting of methyoxycarbonyl, ethoxycarbonyl, methoxyethoxycarbonyl, and benzyloxycarbonyl, (f) $R_2$ is methyl, $R_3$ is selected from the group consisting of methoxycarbonyl and ethoxycarbonyl, and $R_4$ is phenyl substituted with one or more substituents selected from the group consisting of nitro, trifluoromethyl, methoxy, hydroxy, and methylenedioxy, (g) $R_2$ is methyl, $R_3$ is selected from the group consisting of methoxycarbonyl and ethoxycarbonyl, $R_4$ is phenyl substituted with one or more substituents selected from the group consisting of nitro, trifluoromethyl, methoxy, hydroxy, and methylenedioxy, and $R_5$ is selected from the group consisting of methoxycarbonyl, ethoxycarbonyl, and methoxyethoxycarbonyl, (h) $R_2$ is methyl, $R_3$ is ethoxycarbonyl, $R_4$ is phenylacetylenyl, $R_5$ is benzyloxycarbonyl which may be further substituted with methyl, trifluoromethyl, halo, iodo, or nitro groups, and $R_6$ is phenyl, (i) $R_2$ is methyl, $R_3$ and $R_5$ are ethoxycarbonyl, $R_4$ is 2-thienyl, 2-pyridyl, 3-pyridyl, 4-pyridyl, 2-furyl, or 2-benzofuryl, and $R_6$ is phenyl, (j) $R_2$ is methyl, $R_3$ is ethoxycarbonyl, $R_4$ is phenylacetylenyl, $R_5$ is phenylethoxy or phenylpropoxy, and $R_6$ is phenyl, and (k) $R_2$ is methyl, $R_3$ is ethoxycarbonyl, $R_4$ is phenylacetylenyl, $R_5$ is thioethoxy, and $R_6$ is phenyl.

The present invention further provides a compound of the formula IV

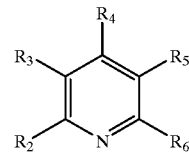

(IV)

or pharmaceutically acceptable salts thereof, wherein $R_2$ is selected from the group consisting of hydrogen and $C_1$–$C_6$ alkyl; $R_3$ is selected from the group consisting of hydrogen and $C_1$–$C_6$ alkyloxycarbonyl; $R_4$ is selected from the group consisting of $C_1$–$C_6$ alkyl, phenyl $C_2$–$C_6$ alkenyl, phenyl $C_2$–$C_6$ alkynyl, aryl, and aryl substituted with one or more substituents selected from the group consisting of nitro and $C_1$–$C_6$ alkyloxy; $R_5$ is selected from the group consisting of hydrogen, $C_1$–$C_6$ alkyloxycarbonyl, and aryl $C_1$–$C_6$ alkyloxy carbonyl; and $R_6$ is selected from the group consisting of hydrogen, aryl, and $C_1$–$C_6$ alkyl; with the proviso that when $R_2$=$R_3$=$R_5$=$R_6$=hydrogen, $R_4$ is not alkyl.

Particular embodiments include compounds of formula IV, wherein (a) $R_2$ is selected from the group consisting of hydrogen and methyl, (b) $R_2$ is selected from the group consisting of hydrogen and methyl, and $R_3$ and $R_5$ are same or different and selected from the group consisting of hydrogen, methoxycarbonyl, and ethoxycarbonyl, (c) $R_2$ is selected from the group consisting of hydrogen and methyl, $R_3$ and $R_5$ are same or different and selected from the group consisting of hydrogen, methoxycarbonyl, and ethoxycarbonyl, and $R_4$ is selected from the group consisting of methyl, o-nitrophenyl, and p-methoxyphenyl, and (d) $R_2$ is selected from the group consisting of hydrogen and methyl, $R_3$ and $R_5$ are same or different and selected from the group consisting of hydrogen, methoxycarbonyl, and ethoxycarbonyl, $R_4$ is selected from the group consisting of methyl, o-nitrophenyl, and p-methoxyphenyl, and $R_6$ is selected from the group consisting of hydrogen, methyl, and phenyl.

The present invention further provides a compound of the formula V

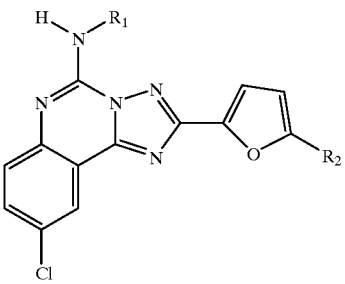

(V)

or a pharmaceutically acceptable salt thereof, wherein $R_1$ is selected from the group consisting of $C_1$–$C_6$ alkylcarbonyl, aryl $C_1$–$C_6$ alkylcarbonyl, aryl $C_2$–$C_6$ alkenylcarbonyl, $C_1$–$C_6$ alkyloxycarbonyl, amino $C_1$–$C_6$ alkylcarbonyl, and arylcarbonyl, wherein said aryl may be further substituted with halo, nitro, hydroxy, amino or cyano; and $R_2$ is hydrogen or halogen. Aryl includes phenyl, naphthyl, and aromatic moieties having 3 or 4 rings.

Particular embodiments include a compound of formula V wherein $R_2$ is hydrogen, and $R_1$ is ethylcarbonyl, benzoyl phenylethylcarbonyl, styrylcarbonyl, 4-nitrobenzylcarbonyl, 4-aminobenzylcarbonyl, or 3-iodo-4-aminobenzylcarbonyl.

"Aryl" in this application refers to phenyl, naphthyl, and aromatic groups with 3 or more rings, and preferably phenyl, unless otherwise described.

All of the aforesaid compounds of the present invention can be used as is or in the form of a pharmaceutical composition comprising a pharmaceutically acceptable carrier and a therapeutically effective amount of the compound.

The present invention further provides a method of treating a mammal comprising selectively blocking one or more of the adenosine receptors of the mammal by administering to the mammal at least one compound of formulas I–V.

The present invention provides a method of treating a mammal comprising selectively blocking the adenosine receptors of a mammal by administering to said mammal at least one compound of the formula I

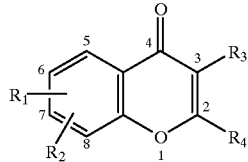

(I)

wherein $R_1$ and $R_3$ are selected from the group consisting of hydrogen, hydroxy, $C_1$–$C_6$ alkoxy, and $C_1$–$C_6$ alkylcarbonyloxy; $R_2$ is selected from the group consisting of hydroxy, $C_1$–$C_6$ alkoxy, and $C_2$–$C_6$ alkenoxy, said alkenoxy together with the carbon atom of the phenyl ring forming an oxygen heterocycle; $R_4$ is selected from the group consisting of phenyl, styryl, phenylbutadienyl, phenylacetylenyl, and —CH=N-phenyl, and substituted phenyl, styryl, phenylacetylenyl, and phenylbutadienyl, wherein the phenyl ring is substituted with 1 to 5 $C_1$–$C_6$ alkoxy groups; with the provisos that when $R_3$ is hydrogen, $R_1$ and $R_2$ are neither hydroxy nor alkoxy; when $R_1$, $R_2$, and $R_3$ are hydrogen, $R_4$ is neither phenyl nor alkyloxyphenyl; and when $R_3$ is hydrogen and $R_4$ is phenyl, neither $R_1$ nor $R_2$ is alkylcarbonyloxy.

Selected compounds of formula I are set forth in Tables 3–5. These compounds have affinity for adenosine receptors in general. Among these compounds, certain compounds have greater affinity for one type of adenosine receptors, e.g., $A_3$, than other types of adenosine receptors. Therefore these compounds can be used to selectively block that type of adenosine receptors for which they have greater affinity. Thus, for instance, compounds 3b, 4, 6, 7, 8, 10, 11b, 11c, 11d, 16, 20, 21 and 24 can be used to selectively block the $A_3$ adenosine receptors in a mammal.

The present invention further provides a method of treating a mammal comprising selectively blocking the adenosine receptors of a mammal by administering to said mammal at least one compound selected from the group consisting of genistein, (±)dihydrogenistein, sakuranetin, α-naphthoflavone, β-naphthoflavone, amaryllidaceae, oxogalanthine lactam, acetylhaemanthine methiodide, 2,3-methylenedioxy-fluorene-9-one, hematoxylin, and arborinine.

The present invention further provides a method of treating a mammal comprising selectively blocking one or more of the adenosine receptors of a mammal by administering to said mammal at least one compound of the formula II

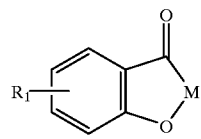

(II)

wherein $R_1$ is selected from the group consisting of hydroxyl and $C_1$–$C_6$ alkoxy, and M is a divalent radical selected from the group consisting of —CH(OH)—CH($R_2$)— and —C(OH)=C($R_2$)—, wherein $R_2$ is selected from the group consisting of styryl and phenylacetylenyl.

Selected compounds of formula II are set forth in Tables 6–7. These compounds have affinity for adenosine receptors in general. Among these compounds, certain compounds have greater affinity for one type of adenosine receptors, e.g., $A_3$, than other types adenosine of receptors. Therefore these compounds can be used to selectively block that type of adenosine receptors for which they have greater affinity. Thus, for instance, compound 38 can be used to selectively block the $A_3$ adenosine receptors in a mammal.

Selected compounds of formula III are set forth in Tables 10 and 18. These compounds have affinity for adenosine receptors in general. Among these compounds, certain compounds have greater affinity for one type of receptors, e.g., $A_1$, than other types adenosine of receptors. Therefore, these compounds can be used to selectively block that type of receptors for which they have greater affinity. Thus, for instance, compounds 52, 58, 60, 61, 62, 63, 64, 65, 68, 69, 70, 71, 75, 76, and 77, which have greater affinity to $A_1$ adenosine receptors than $A_{2a}$ receptors, can be used to selectively block $A_1$ adenosine receptors. Further, compounds 63, 64, 65, 74, 75, 76, 79, 87, 90, 93–95, 98–101, 105–107, 109, 115–126, 129–130b, 133, and 136, which have greater affinity for $A_3$ adenosine receptors than $A_1$ or $A_{2a}$ adenosine receptors, can be used to selectively block $A_3$ adenosine receptors.

The present invention further provides a method of treating a mammal comprising selectively blocking one or more of the adenosine receptors of a mammal by administering to said mammal at least one compound of the formula IV

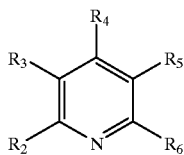

(IV)

or pharmaceutically acceptable salts thereof, wherein $R_2$ is selected from the group consisting of hydrogen and $C_1$–$C_6$ alkyl; $R_3$ is selected from the group consisting of hydrogen and $C_1$–$C_6$ alkyloxycarbonyl; $R_4$ is selected from the group consisting of $C_1$–$C_6$ alkyl, phenyl $C_2$–$C_6$ alkenyl, phenyl $C_2$–$C_6$ alkynyl, aryl, and aryl substituted with one or more substituents selected from the group consisting of nitro and $C_1$–$C_6$ alkyloxy; $R_5$ is selected from the group consisting of hydrogen, $C_1$–$C_6$ alkyloxy carbonyl, and aryl $C_1$–$C_6$ alkyloxycarbonyl; and $R_6$ is selected from the group consisting of hydrogen, aryl, and $C_1$–$C_6$ alkyl.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, interperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkylimidazoline quaternary ammonium salts, and (e) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The compounds of the present invention can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be treated in accordance with the present inventive method include inflammatory disorders, such as vascular inflammation and arthritis, allergies, Crohn's disease, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, severe neurological disorders related to excitotoxicity, Parkinson's disease, Huntington's chorea, and other diseases of the central nervous system (CNS), cardiac disease, kidney disease, and contraception.

These compounds can be significant cerebral protectants. As such, the above compounds can be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies. The above method is applicable, for example, where a mammal has or is at risk of having a condition, disorder, or disease state associated with the cellular release of inositol-1,4,5-triphosphate or diacylglycerol. The method is also applicable when said mammal has or is at risk for hyperactivity and said compound in binding to said $A_3$ adenosine receptors functions as a locomotor depressant.

The present inventive method is also applicable when said mammal has or is at risk for hypertension and said compound in binding to said $A_3$ adenosine receptors functions as a hypotensive agent. The method is also applicable when said mammal has or is at risk for anxiety and said compound in binding to said $A_3$ adenosine receptors functions as an anxiolytic agent. The method is furthermore applicable when said mammal has or is at risk for cerebral ischemia and said compound in binding to said $A_3$ adenosine receptors functions as a cerebroprotectant. The method is also applicable when said mammal has or is at risk for seizures and said compound in binding to said $A_3$ adenosine receptors functions as an antiseizure agent.

The present inventive method can be administered chronically as well as acutely.

The present inventive method includes the administration to an animal, such as a mammal, particularly a human, in need of the desired adenosine receptor-dependent response of an effective amount, e.g., a therapeutically effective amount, of one or more of the aforementioned present inventive compounds or pharmaceutically acceptable salts or derivatives thereof, alone or in combination with one or more other pharmaceutically active compounds.

Any suitable pharmaceutically acceptable salts can be used. Example of suitable salts include carbonate, bicarbonate, sulfate, bisulfate, nitrate, halides, phosphates, oxalate, acetate, formate, citrates, and amino acid salts.

Some of the compounds of the present invention can be utilized as functionalized congeners for coupling to other molecules, such as amines and peptides. The use of such congeners provide for increased potency, prolonged duration of action, specificity of action, and prodrugs. Water solubility is also enhanced, which allows for reduction, if not complete elimination, of undesirable binding to plasma proteins and partition into lipids. Accordingly, improved pharmacokinetics can be realized.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or other therapeutic response in the animal over a reasonable time frame. One skilled in the art will recognize that dosage will depend upon a variety of factors including the strength of the particular compound employed, the age, species, condition, and body weight of the animal, as well as the severity/stage of the disease or condition. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective adenosine receptor-dependent responses. Exemplary dosages range from about 0.01 to about 100 mg/kg body weight of the animal being treated/day. Preferred dosages range from about 0.1 to about 10 mg/kg body weight/day.

The abbreviations used in this application have the following meaning:

| | |
|---|---|
| [$^{125}$I]AB-MECA | [$^{125}$I]N6-(4-amino-3-iodobenzyl) adenosine-5'-N-methyluronamide |
| CHO | Chinese hamster ovary |
| DMF | N,N-dimethylformamide |
| DMSO | dimethylsulfoxide |
| $K_i$ | equilibrium inhibition constant |
| R-PIA | R-N6-phenylisopropyladenosine |

Bay K 8422: 1,4-dihydro-2,6-dimethyl-5-nitro-4-[2-(trifluoromethyl)-phenyl]-3-pyridine carboxylic acid methyl ester The following examples further illustrate the present invention but, of course, should not be construed as in any way limiting its scope.

EXAMPLE 1

This Example illustrates the various analytical methods employed in the characterization of the compounds of the present invention.

Proton nuclear magnetic resonance spectroscopy was performed on a Varian GEMINI-300 spectrometer and spectra were taken in d6-DMSO. Electron-impact mass spectrometry was performed with a VG7070F mass spectrometer at 6 kV. Elemental analysis was performed by Atlantic Microlabs, Inc. (Norcross, Ga.).

EXAMPLE 2

This Example illustrates the procedure for determining the affinity of the present inventive compounds for adenosine receptors.

$K_i$ values at $A_1$ and $A_{2a}$ receptors were determined in radioligand binding assays in brain membranes vs. [3H]PIA or [3H]CGS 21680, respectively. Schwabe et al., *Naunyn-Schmiedeberg's Arch. Pharmacol.*, 313, 179–187 (1980); Jarvis et al., *J. Pharmacol. Exp. Therap.*, 251, 888–893 (1989). Affinity at human brain $A_3$ receptors expressed in HEK-293 cells, Salvatore et al., *Proc. Natl. Acad. Sci.*, 90, pp. 10365–10369 (1993), was determined using [$^{125}$I]AB-MECA. Olah et al., *Mol. Pharmacol.*, 45, 978–982 (1994). Compounds were tested at human $A_3$ receptors, and selected compounds, which would be preferred for comparison with the $A_1$ and $A_{2a}$ data, were also tested at rat $A_3$ receptors stably expressed in Chinese hamster ovary (CHO) cells for inhibition of adenylyl cyclase. Kim, H. O., *J. Med. Chem.*, 37, 3614–3621 (1994).

The human $A_3$ receptor was chosen for several reasons including that the affinity of most known adenosine adenosine ligands is minimal at rat $A_3$ receptors. In addition, the human $A_3$ receptor, being more sensitive, allowed for a better comparison between compounds. Salvatore et al., *Proc. Natl. Acad. Sci.*, 90, 10365–10369 (1993).

EXAMPLE 3

This Example illustrates the general synthetic methodology of certain flavone derivatives of the present invention.

Figure 2:
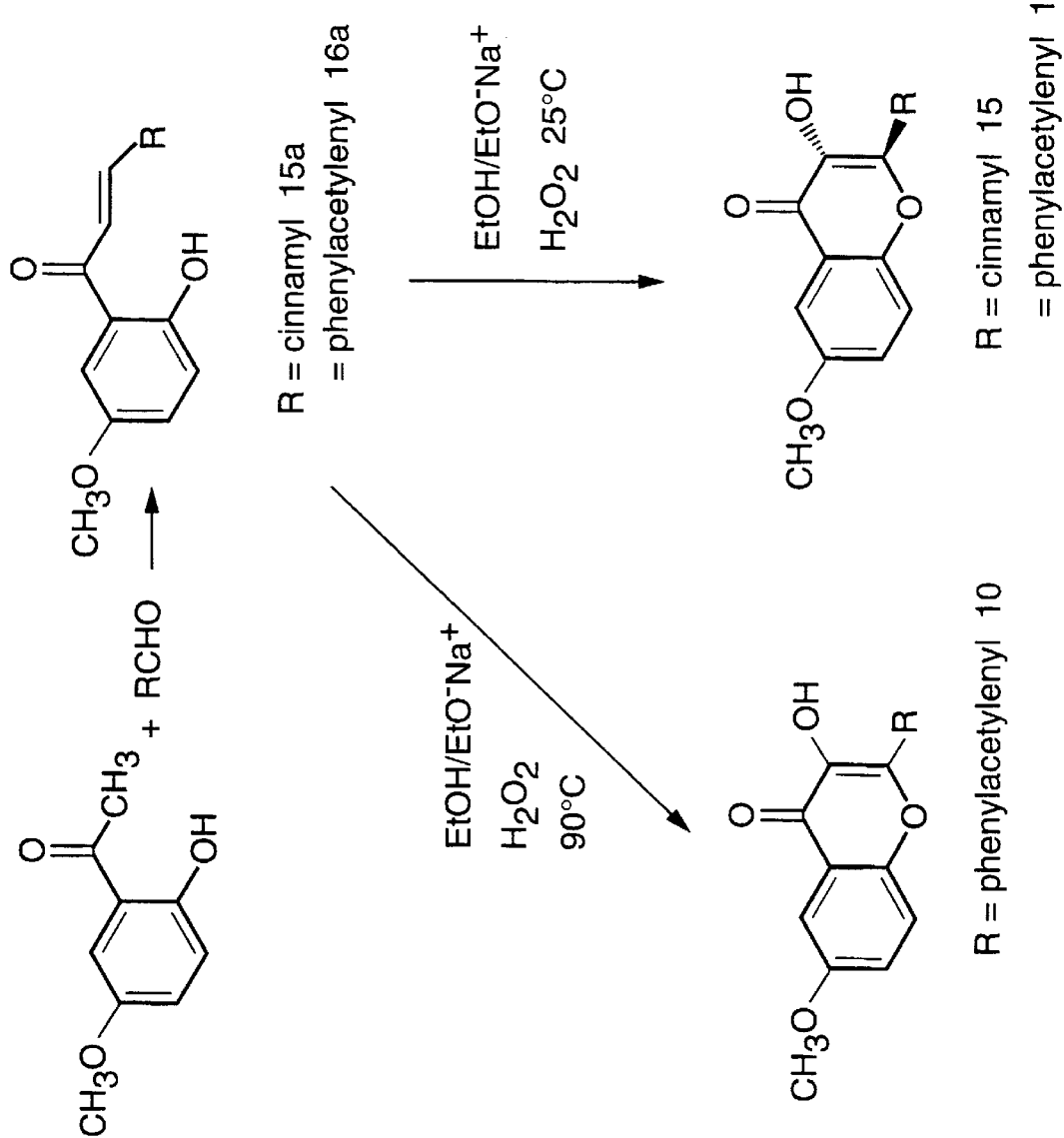
FIG. 2 depicts a method of synthesis of the 2-phenylacetylenyl and 2-cinnamyl derivatives, 10, 15, and 16, starting from 4-methoxyfuranochromone.
Figure 3:
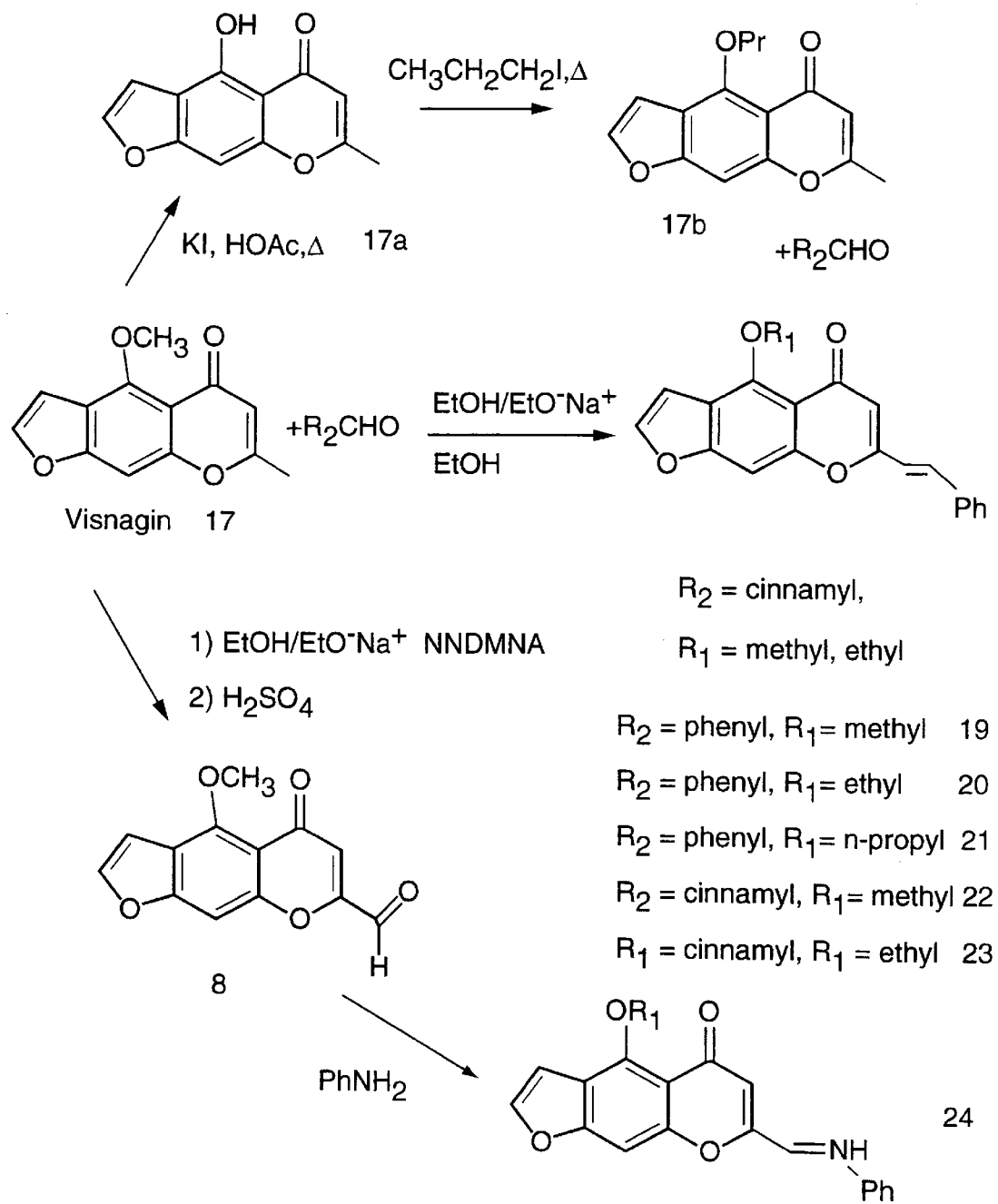
FIG. 3 depicts a method of synthesis of certain 2-substituted flavonoid derivatives, 19–24, starting from visnagin.
Figure 4:
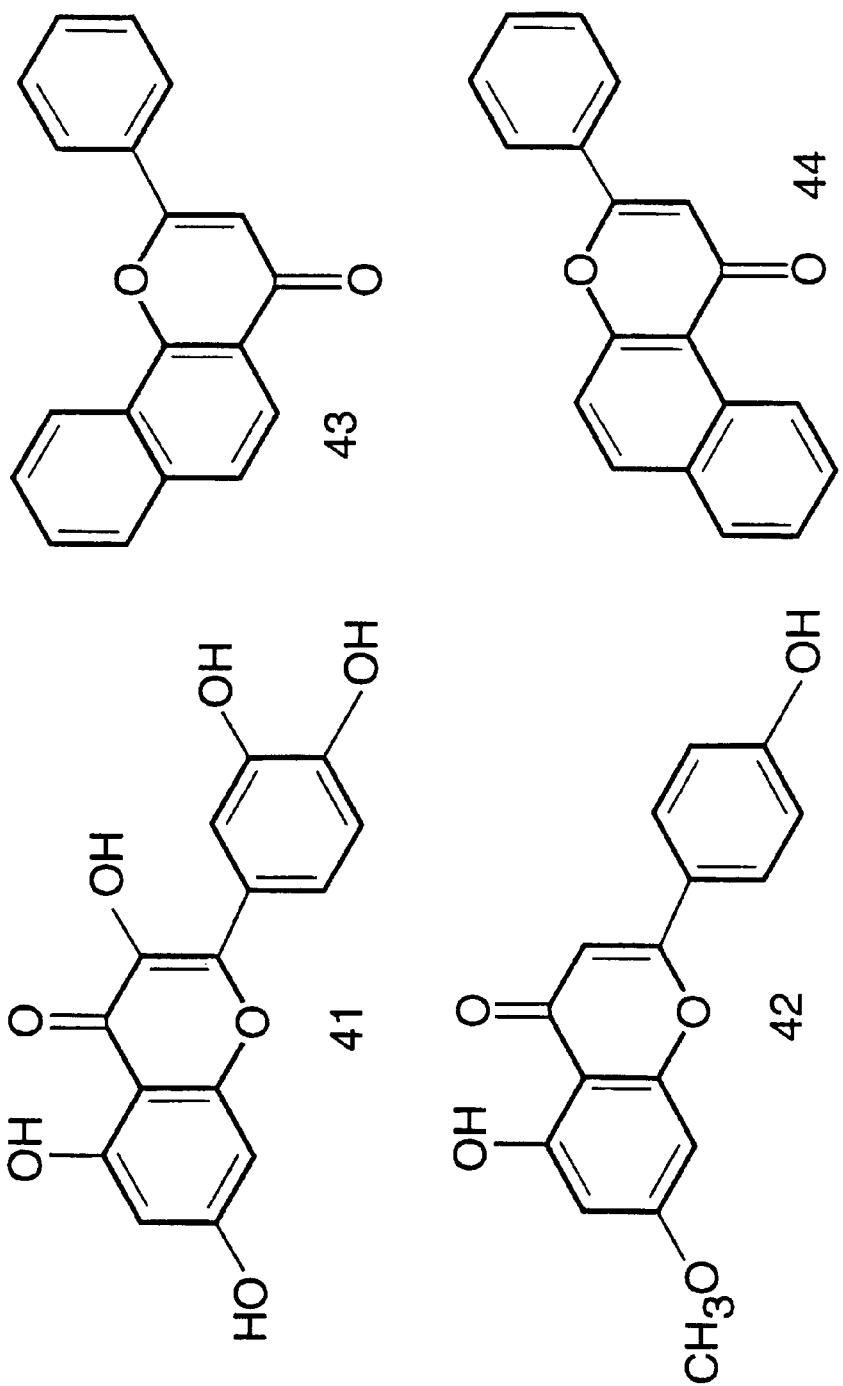
FIG. 4 depicts the structures of flavonoid derivatives 41–44.
Figure 5:
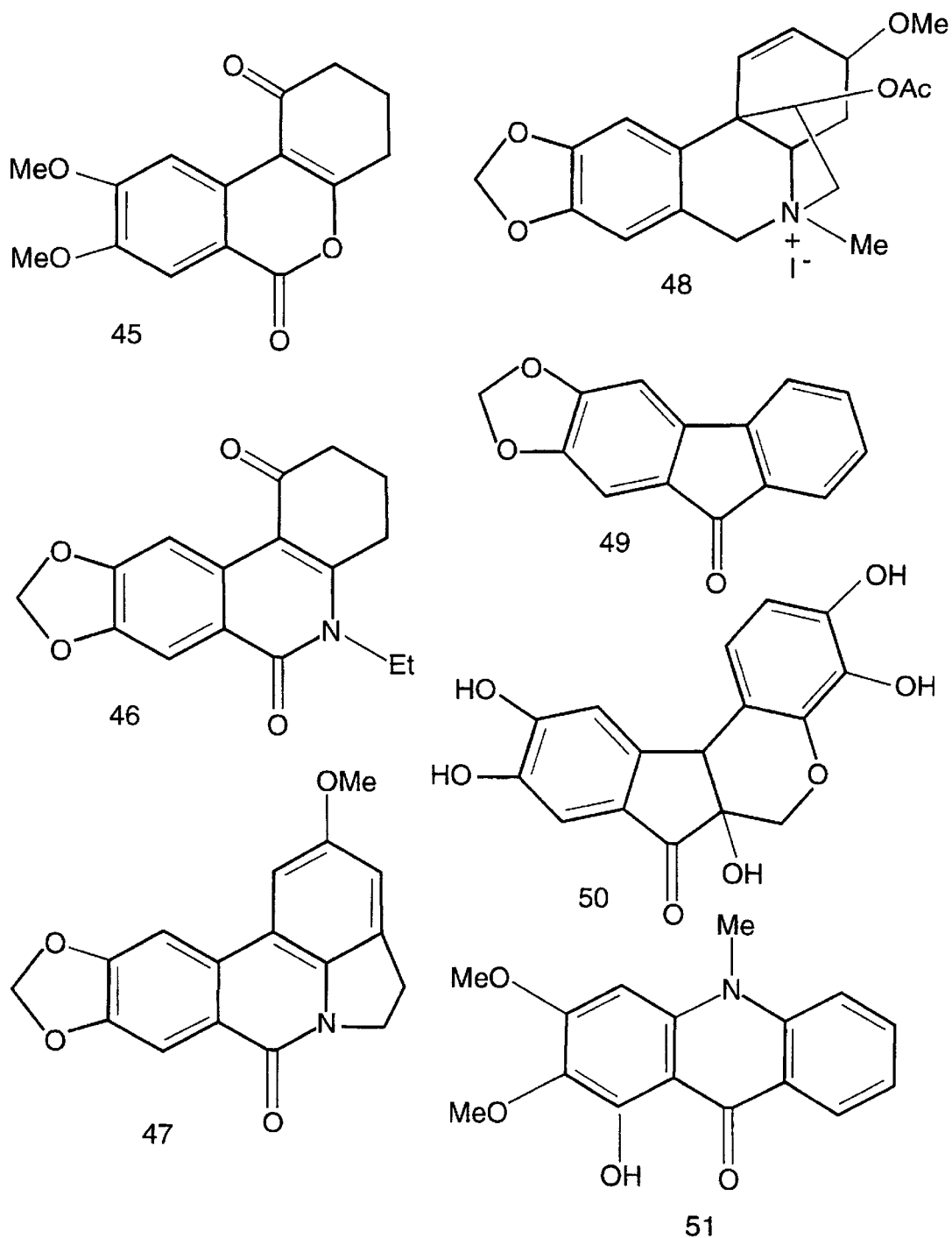
FIG. 5 depicts the structures of flavonoid derivatives 45–51.

The synthesis of the flavone derivatives can be accomplished following the teachings in literature and the procedures set forth herein. Wollenweber et al., J. B. Harborne, (Chapman and Hall, eds.), London, 259–335 (1993); Cushman et al., *J. Med. Chem.*, 37, 3373–3382 (1994); Cunningham et al., *Anti-Cancer Drug Design*, 7, 365–384 (1992); Lee et al., *Tetrahedron*, 51, 4909–4922 (1995). As shown in FIG. 2, the flavone ring system could be formed via a condensation of a 2-hydroxyacetophenone derivative, Lee et al., *Tetrahedron*, 51, 4909–4922 (1995), with the appropriate aldehyde, Williams, *Spectroscopic Methods in Organic Chemistry*, 4th ed., McGraw Hill, London, 1989, which gives rise to the 2-substituent. A cinnamaldehyde derivative was used as the second component thus leading to cinnamyl substitution at the 2-position. The condensation resulted first in a trans-olefin, Duarte et al., *Eur. J. Pharmacol.*, 286, 115–122 (1995), which could be cyclized under basic oxidizing conditions to give either the 2,3-saturated dihydroflavonol analogues, Kim et al., *J. Med. Chem.*, 37, 3373–3382 (1994), and Siddiqi et al., *Nucleosides Nucleotides* (1995, in press), or at higher temperature the corresponding dehydro derivative, Palmer et al., *J. Biol. Chem.*, 270, 16895–16902 (1995), a flavonol. Evidence that the 3-hydroxyflavanones obtained were of the trans configuration is from NMR. The coupling constant for the 2- and 3-position protons for compounds 15–16 is ~12 Hz, which is characteristic of trans vicinal coupling. Williams et al., *Spectroscopic Methods in Organic Chemistry*, 4th ed., McGraw Hill, London (1989).

An alternate approach to providing olefinic substitution at the 2-position (FIG. 2) was to condense a 2-methylchromone (such as the natural product visnagin, 17)27 with an aldehyde, Hafez, *Czech. Chem. Commun.*, 59, (1994), under basic conditions. This method was used to prepare the 2-cinnamyl derivative, Ji et al., *J. Med. Chem.* (1996, in press). Evidence for a trans-styryl group of Ji et al., *J. Med. Chem.* (1996, in press), was found in the NMR spectra with the olefinic coupling constant of 15 Hz. In the presence of ethoxide ions the 5-methoxy group readily exchanged for ethoxy, resulting in compound 20. The corresponding 5-propoxy derivative, 21, Markham et al., *J. B. Harborne*, (Chapman and Hall eds., London, 441–497 (1993), was obtained using an alternate approach in which visnagin was demethylated to give Schwabe et al., *Naunyn-Schmiedeberg's Arch. Pharmacol.*, 313, 179–187 (1980), followed by condensation with benzaldehyde. The 2-methyl group of visnagin could also be oxidized to an aldehyde group, as in 18. Hafez M. El-Shaaer, *Collect. Czech. Chem. Commun.*, 59 (1994).

EXAMPLE 4

This Example illustrates the alkylation of galangin, 1 and morin, 5a.

The alkylation of galangin was carried out using the appropriate alkyl iodide and potassium carbonate in refluxing acetone (FIG. 1), providing the completely alkylated product, 3a or 4. Partial alkylation leaving the 5-position hydroxyl group unreacted, to provide 3b, was accomplished under less forceful conditions, e.g. alkyl bromide at room temperature. The O-alkylation of morin, 5a, (2',3,4',5,7-pentahydroxyflavone) was complicated by an even lesser reactivity of the 5-hydroxy group than in galangin, leading to tetra- rather than penta-substitution (FIG. 1). Thus, when ethyl sulfate was used the fully alkylated morin derivative, 8, was obtained, while reaction with ethyl iodide provided only the tetraethyl derivative, 7. The position of the non-alkylated hydroxyl group of 3b and 7 was determined using NMR. The resonance for the 5-OH proton appears at roughly 12 ppm. Kim et al., *J. Med. Chem.*, 37, 3614–3621 (1994). The downfield shift is apparently caused by the adjacent carbonyl to which it may H-bonding, forming a six-membered ring. This proton signal is present in the spectra of 3b, 5a and 7 but not 8.

The physical characterization data of the flavonoid derivatives described in this Example as well as in the following Examples are set forth in Tables 1 and 2.

3,5,7-Trimethoxyflavone (2)

Galangin (27 mg, 0.1 mmol) was dissolved in dried acetone (20 mL), solid potassium carbonate (0.5 g) and dimethyl sulfate (1 mL) were added, and the mixture was refluxed for 4 hrs, then cooled to room temperature. The solution was filtered and evaporated, water (20 mL) and concentrated ammonium hydroxide (2 mL) were added and the solution was extracted with ethyl acetate (15 mL×2). The solvent was evaporated and the residue was recrystallized from methanol/water to give 21 mg product (67%). 1HNMR (DMSO-d6): d 3.73 (s, 3H, 3-OCH3), 3.86 (s, 3H, 7-OCH3), 3.86 (s, 3H, 5-OCH3), 6.48 (s, 1H, 8-H), 6.79 (s, 1H, 6-H), 7,99 (m, 3H), 8.02 (m, 2H). MS (CI/NH3): m/z 313 (MH+, base).

3,5,7-Triethoxyflavone (3a)

Galangin (30 mg, 0.11 mmole) was dissolved in dried acetone (45 mL), solid potassium carbonate (0.5 g) and iodoethane were added, and the mixture was refluxed for overnight. The solution was filtered and evaporated, water (20 mL) and concentrated ammonia (1 mL) were added, and the solution was extracted with ethyl acetate. The ethyl acetate was evaporated, and the crude mass was purified on a preparative silica TLC plate to give 12 mg 3,5,7 triethoxyflavone. mp 111–114° C. mass (FAB) m/z 355 (M++1, base) 1H NMR (CDCl3) 1.33 (t, 3H, CH3), 1.55 (t, 3H, CH3), 1.62 (t, 3H, CH3), 4.1–4.25 (m, 6H, CH2), 6.4 (s, 1H), 6.55 (s, 1H), 7.5–7.6 (m, 3H), 8.1–8.2.

3, 7-Diethoxy-5-hydroxyflavone (3b)

Galangin (27 mg, 0.1 mmol) was dissolved in dried acetone (20 mL), solid potassium carbonate (0.5 g) and bromoethane (1 mL) were added and the mixture was stirred overnight, at room temperature. The solution was filtered and evaporated, water (20 mL) and concentrated ammonium hydroxide (2 mL) were added and the solution was extracted with ethyl acetate (20 mL×2). The solution was dried and the solvent was evaporated. The residue was purified by preparative TLC plate (silica, ethyl acetate/petroleum ether 2:8) to give 21 mg product (64%). 1HNMR (CDCl3): d 1.34 (t, 3H, J=7.3 Hz, 3-CH3), 1.48 (t, 3H, J=7.1 Hz, 7-CH3), 4.14 (m, 4H, 2×OCH2), 6.38 (s, 1H, 6-H), 6.47 (s, 1H, 8-H), 12.64 (s, 1H, 5-OH). MS (CI/NH3): m/z 327 (MH+, base).

3,5,7-Tripropyloxyflavone (4)

Galangin (30 mg, 0.11 mmole) was dissolved in dried acetone (45 mL), solid potassium carbonate (0.5 g) and 1-iodopropane were added and the mixture was refluxed overnight. The solution was filtered and evaporated, water (20 mL) and concentrated ammonia (1 mL) were added, and the solution was extracted with ethyl acetate. The ethyl acetate was evaporated, and the crude mass was purified on a preparative TLC plate (silica) to give 25 mg (63%) of 3,5,7-tripropyloxyflavone, mp 90–93° C. Mass spectra (CI—NH3) m/z 397 (M++1), base) 1H NMR (CDCl3) 0.85–1.2 (m, 9H), 1.6–2.1(m, 6H), 3.9–4.1(m, 6H), 6.32 (s, 1H), 6.5 (s, 1H), 7.4–7.5 (m, 3H), 8.04–8.12 (m, 2H).

2',3,4',5,7-Pentamethyloxyflavone (6)

Morin (120 mg, 0.4 mmol) was dissolved in dried acetone (80 mL). Solid potassium carbonate (2 g) and iodomethane (2 mL) were added, and the mixture was refluxed overnight, then cooled to room temperature. The solution was filtered and evaporated, and the residue was separated by preparative TLC plates (silica, ethyl acetate) to give 80 mg product (55%). 1HNMR (CDCl3): d 3.86, 3.88, 3.91, 3.93, 4.02 (5s, 15H, 5×OCH3), 6.39, 6.49, 6.62 (s, 1H, 8-H), 6.79 (3m, 3H, phenyl), 6.65 (m, 1H, 8-H), 7.42 (m, 1H, 6-H)). MS (EI): m/z 372 (M+), 371 (M-H)+, 341 (M-OCH3)+.

2',4',3,7-Tetraethoxy-5-hydroxymorin (7)

Compound 7 was synthesized according to the above procedure for 6, except for using iodoethane instead of iodomethane. The product, 7, was separated on preparative TLC with petroleum ether/ethyl acetate and displayed a mass (FAB) m/z 415 (M++1, base). 1H NMR (CDCl3) 1.15 (t, 3H, CH3), 1.35 (t, 3H, CH3), 1.45 (dt, 6H, CH3), 3.9–4.2 (m, 8H, CH2), 6.33 (d, 1H), 6.6 (m, 3H), 7.4 (d, 1H).

2',3,4',5,7-Pentaethoxyflavone (8)

Morin (302 mg, 1 mmol) was dissolved in dried acetone (80 mL), solid potassium carbonate (5 g) and diethyl sulfate (5 mL) were added, and the mixture was refluxed overnight, then cooled to room temperature. The solution was filtered and evaporated, water (50 mL) and concentrated ammonium hydroxide (10 mL) were added and the solution was extracted with ethyl acetate (40 mL×2). The solution was dried, and the solvent was evaporated. The residue was crystallized from ethyl acetate and petroleum ether (1:9) to give 335 mg product (76%). 1HNMR (CDCl3): d 1.12 (t, 3H, J=7.1 Hz, CH3), 1.32 (t, 3H, J=7.1 Hz, CH3), 1.45 (2t, overlap, 6H, 2×CH3), 1.56 (t, 3H, J=7.1 Hz, CH3), 4.10 (m, 10 H, 5×OCH2), 6.32 (d, 1H, J=1.2 Hz, 2-phenyl), 6.39 (s, 1H, 2-phenyl), 6.53 (s, 1H, 2-phenyl), 6.58 (s, 1H, 6-H), 7.37 (d, 1H, 8-H). MS (CI/NH3): m/z 443 (MH+, base).

EXAMPLE 5

This Example illustrates the synthesis of 2-phenylacetylenyl-3-hydroxy-6-methoxyflavone (10).

1-(2-Hydroxy-5-methoxy)-5-phenylpenta-2-en-4-yne-1-one (Compound 15a, 60 mg, 0.2 mmole) was dissolved in ethanol (1.5 mL). Sodium hydroxide 1N (0.4 mL) and hydrogen peroxide (0.5 g) were added, and the mixture was heated at 90° C. for 35 min. The cooled mixture was diluted with water (5 mL) and acidified with hydrochloric acid, 1N. A precipitate was collected and recrystallized from methanol. Mass (CI NH3) m/z 293 (M++1, base), 1H NMR (CDCl3) 3.95 (s, 3H, CH3), 6.92 (s,1H), 7.25–8.0 (m, 7H).

EXAMPLE 6

This Example illustrates the synthesis of trans-2-Styryl-3-hydroxy-6-methoxyflavanone (15).

2'-Hydroxy-5'-methoxyacetophenone (4.1 g, 22 mmole) and cinnamaldehyde (3.35 g, 25 mmole) were dissolved in minimum methanol (2.5 mL). Concentrated sodium hydroxide (12.5 mL, 50%) was added, and the mixture was kept on ice for 8 hr. The resultant solid was suspended in water and acidified using HCl (4N). The oil that separated was dissolved in ethanol and crystallized from ethanol/water to give 1-(2-hydroxy-5-methylphenyl)-5-phenylpenta-2,4-dien-1-one (1.2 g) as red-brown powder. Mass (CI—NH3) m/z 281 (M++1, base). 1H NMR (CDCl3).3.9(s, 3H, CH3),6.95–7.8 (m, 12H). The above compound (170 mg, 0.6 mmole) was dissolved in a mixture of ethanol (3.5 mL) and acetone (4 mL). Sodium hydroxide 1N (1 mL) and hydrogen peroxide (1 mL, 35%) were added, and the solution was stirred 6 hr.

at room temperature. The mixture was precipitated by adding water and HCl and purified on preparative TLC (petroleum ether-ethyl acetate) to give compound 15, mp 160–163° C. mass (CI NH3) m/z 297(M++1,base). 1H NMR (CDCl3) 3.9(s,3H,CH3), 4.45(d,J=12 Hz,1H), 4.8(m,1H), 6.55(dd,1H), 6.9–7.6(m,9H).

EXAMPLE 7

This Example illustrates the synthesis of trans-2-phenylacetylenyl-3-hydroxy-6-methoxyflavanone (16).

2'-Hydroxy-5'-methoxyacetophenone and phenylphenylacetylenyl aldehyde were condensed according to the procedure for the preparation of compound 15 to give 1-(2-hydroxy-5-methylphenyl)-5-phenylpenta-2-en-4-yne-1-one. Mass (CI—NH3) m/z 279 (M++1, base). 1H NMR (CDCl3) .3.9 (s, 3H, CH3), 7.0 (d, 1H), 7.1–7.6 (m,9H). The above compound was allowed to react with hydrogen peroxide to give compound 16 as a white powder, mp 135–138° C. Mass (EI) m/z 295 (M+1) 150 (base). 1H NMR (CDCl3) d 3.85 (s, 3H, OCH3), 4.6 (d, J=12 Hz, 1H), 5.09 (d, J=12 Hz, 1H), 7.0–7.6 (m, 8H). 4-Methoxy-7-formyl-5H-furo [3,2-g][1]-benzopyrano-5-one (18) was synthesized from visnagin (4-methoxy-7-methyl-5H-furo[3,2-g][1]-benzopyrano-5-one) according to Duarte et al., *Eur. J. Pharmacol.*, 286, 115–122 (1995).

EXAMPLE 8

This Example illustrates the synthesis of 4-methyloxy-7-trans-styryl-visnagin (19) and 4-ethyloxy-7-trans-styryl-visnagin (20).

Visnagin (17, 160 mg, 0.7 mmole) and benzaldehyde (120 mg, 1.1 mmole) were dissolved in ethanol (4 mL). Sodium ethoxide (20% in ethanol, 0.5 ml) was added, and the mixture was stirred for 10 min at 80° C. Disappearance of the starting material was accompanied with formation of two products Rf 0.7 and 0.8 in ethyl acetate. Both products were separated on preparative TLC plates (ethyl acetate) to give compound 19, mp 175–178° C. Mass (CI NH3) m/z 319 (M++1, base) 1H NMR (CDCl3) d 4.2 (s, 3H, OCH3), 6.23 (s, 1H), 6.75 (d, J=15 Hz, 1H), 7.05 (s, 1H), 7.3–7.8 (m, 8H).

Compound 20, mp 148–151° C. Mass (CI NH3) m/z 333 (M++1, base). 1H NMR (CDCl3) 1.55 (t, 3H, CH3), 4.4 (q, 2H, OCH2), 6.23 (s, 1H), 6.78 (d, J=15 Hz, 1H), 7.0 (s, 1H), 7.35–7.7 (m, 8H).

EXAMPLE 9

This Example illustrates the synthesis of 4-propyloxy-7-trans-styryl-visnagin (21).

A mixture of visnagin (2 g, 8.7 mmol), potassium iodide (10 g) and acetic acid (50 mL) was refluxed for 7 hrs. After cooling, the precipitate was removed by filtration, and the filtrate was evaporated under reduced pressure, and coevaporated with toluene (10 mL×2). The residue was crystallized from ethanol to give 1.62 g (81%) of demethylated product of visnagin, 17a. 1HNMR (CDCl3): d 2.40 (s, 3H, 7-CH3), 6.12 (s, 1H, 6-H), 7.00 and 7.62 (2d, 2H, J=2.9 Hz 3-H and 2H), 7.05 (s, 1H, 9-H), 13.6 (s, 1H, 4-OH). The mixture of demethylated visnagin (430 mg, 2 mmol), iodopropane (3 mL) and potassium carbonate (5 g) in dry acetone (80 mL) was refluxed overnight. The solid was removed by filtration, and the solvent was evaporated, water (50 mL) and concentrated ammonium hydroxide (15 mL) were added, and the solution was extracted with ethyl acetate (40 mL×2). The organic layer was dried over sodium sulfate, and the solvent was evaporated. The residue was purified by preparative TLC plates (silica, ethyl acetate/petroleum ether, 4:6) to give 465 mg (90%) of 4-propyloxy-visnagin, 17b. 1HNMR (CDCl3): d 1.10 (t, 3H, J=7.5 Hz), 1.94 (m, 2H), 2.33 (s, 3H, 7-CH3), 4.23 (t, 2H, J=6.7 Hz, 4-OCH2), 6.03 (s, 1H, 6-H), 6.97 and 7.60 (2d, 2H, J=2.7 Hz, 3-H and 2H), 7.27 (s, 1H, 9-H).

4-propyloxy-visnagin (86 mg, 0.3 mmol) and benzaldehyde (50 mg, 0.5 mmol) were dissolved in ethanol (2 mL). While stirring, sodium ethoxide (20% in ethanol, 0.3 mL) was added, and the mixture was stirred for 15 min at 80° C. The solvent was evaporated, and the residue was partitioned between ice water (20 mL) and ethyl acetate (20 mL), the aqueous layer was extracted with ethyl acetate (20 mL), and the combined organic layer was dried over sodium sulfate. The solvent was evaporated, and the residue was separated by preparative TLC plate (silica, ethyl acetate/petroleum ether, 4:6) to give 26 mg of the desired product, 21 (25% yield). 1HNMR (CDCl3): d 1.07 (t, 3H, J=7.5 Hz), 1.97 (m, 2H), 4.25 (t, 2H, J=6.7 Hz, 4-OCH2), 6.21 (s, 1H, 6-H), 6.78 (d, 2H, J=14 Hz, 3-H), 7.00 (s, 1H, 9-H), 7.33 (m, 8H). MS (CI/NH3): m/z 347 (MH+, base).

EXAMPLE 10

This Example illustrates the synthesis of 4-methoxy-7-phenylbutadienyl visnagin (22) and 4-ethoxy-7-phenylbutadienyl visnagin (23).

Compound 22 was prepared by dissolving visnagin and cinnamaldehyde in ethanol in the presence of sodium ethoxide according to the above procedure for preparing compounds 19 and 20 to yield compound 22, mp 162–165° C. Mass (EI) m/z 344 (M+, base). 1H NMR (CDCl3) d 4.2 (s, 3H, OCH3), 6.15 (s, 1H), 6.33 (d, J=15 Hz, 1H), 6.95 (s, 1H), 7.0–7.6 (m, 10H).

Compound 23 was also isolated from the above reaction. Mass (EI) m/z 358 (M+), 343 (M-15, base). 1H NMR (CDCl3) 1.55 (t, 3H, CH3), 4.4 (q, 2H, OCH2), 6.15 (s, 1H), 6.35 (d, J=15 Hz, 1H), 7.4 (d, J=15 Hz, 1H), 6.9–7.6 (m, 10H).

EXAMPLE 11

This Example illustrates the synthesis of compound 24 (the Schiff base of compound 18).

Compound 18 (400 mg) and aniline (0.5 mL) were dissolved in toluene and stirred overnight at 25° C. The course of the reaction was followed using analytical TLC (silica, CHCl3/MeOH, 20:1). The solvent was evaporated, and excess aniline was removed under high vacuum. The product (Rf ~0.7) was purified using preparative TLC (silica, ethyl acetate). Mass (CI NH3) m/z 320 (M++1, base).

EXAMPLE 12

This Example illustrates the synthesis of 3,5,7-triacetoxyflavone (34).

Galangin (9.0 mg, 33 μmol) was dissolved in 1 mL DMF and treated with acetic anhydride (0.2 mL) and 4,4- dimethylaminopyridine (3 mg). After stirring for 10 min, 2 mL of 1 N NaH$_2$PO$_4$ was added. A white precipitate was removed by filtration, and recrystallized from methanol/water to yield 11.4 mg of a solid (87%), which was homogeneous by TLC (Rf 0.56, silica, chloroform:methanol:acetic acid, 95:4:1). Mass spec: 414 (m+1+NH3), 397 (m+1), 355 (m+1+NH3-OAc). Mp 128–129° C. NMR d 7.6 (3H, Ar), 7.9 (m, 2H, Ar), 7.65 and 7.17 (each, d, 1H, J=2 Hz, Ar, o- to AcO), 2.34 (s, 6H, Ac), 2.30 (s, 3H, Ac). CHN analysis.

EXAMPLE 13

This Example illustrates another method of synthesis of 2',3,4',5,7-pentamethyloxyflavone (38, also designated as compound 6 in Example 4).

Morin hydrate (25 mg, 82 μmol, Aldrich) was dissolved in dry acetone (20 mL), in which was suspended potassium carbonate (1.0 g). Dimethyl sulfate (1.0 mL, 11 mmol) was added, and the mixture was refluxed for four h under nitrogen. After cooling in an ice bath, 2 mL concentrated ammonium hydroxide were added in aliquots followed by 20 mL water. The solution was extracted with ethyl acetate. The organic layer was dried and evaporated, and the white solid residue was recrystallized from methanol/water to yield 11 mg (36%) of 20, which was homogeneous by thin layer chromatography (Rf 0.32, silica, chloroform:methanol:acetic acid, 95:4:1). Mass spec: 373 (m+1), 359 (m+1-CH2), 343. Mp. 153–156° C. NMR d 7.35 (d, 1H, J=8 Hz, Ar, 6-Ph), 6.66 (dd, 1H, J=2, 8 Hz, Ar, 5-Ph), 6.70 and 6.62 and 6.48 (each, d, 1H, J=2 Hz, Ar), 3.84 (s, 9H, Me), 3.80 (s, 3H, Me), 3.61 (s, 3H, Me). CHN analysis.

EXAMPLE 14

This Example illustrates the synthesis of compound 45.

Compound 45 was synthesized by a modification of a literature procedure. Fales et al. *J. Amer. Chem. Soc.*, 77, 5885–5890 (1955). 6-Bromo-3,4-dimethoxybenzoic acid (6-bromoveratric acid, 2.0 g, 7.7 mmol, Spectrum Chem. Corp., New Brunswick, N.J.) was dissolved in 50% EtOH/H2O (100 mL), and treated with resorcinol (0.85 g, 7.7 mmol), 50 mg copper powder, 50 mg cupric acetate, and sodium hydroxide (0.31 g, 7.7 mmol). The mixture was heated to reflux overnight. The reaction mixture was extracted once with ether, and insoluble solids were removed by filtration. The aqueous layer was acidified with 1 N HCl to form the lactone. The precipitate was removed by filtration and dried. In order to remove unreacted 6-bromoveratric-acid from this solid containing the product, it was suspended and partially dissolved in cold saturated aqueous NaHCO3. The remaining insoluble solids were collected by filtration and the washings discarded. The dried residue was recrystallized from EtOH to give 0.74 g of the pure product (35% yield). NMR: CDCl3 d ppm 8.68 and 7.65 (each s, 1H, Ar), 4.06 and 3.99 (each s, 3H, Me), 2.95 and 2.67 (each t, 2H, CH2), 2.18 (m, 2H, CH2). Mp. 236–237° C. CHN analysis.

EXAMPLE 15

This Example illustrates the synthesis of 2,3-methylenedioxy-fluorene-9-one (49).

Gaseous HF was condensed by collecting in a Teflon vial placed in a dry ice/acetone bath. 6-Phenylpiperonylic acid (100 mg, 0.41 mmol) was added to HF (2 mL) and the solution let stand overnight. The HF was evaporated leaving the pure fluorenone derivative in quantitative yield (92 mg), mp 156–157° C. CHN analysis was carried out.

TABLE 1

Physical characterization of flavone, flavanol, and flavanone derivatives.

| Compound | Formula | m.p. (° C.) | M.W. (anhyd) | M.W. (MS)$^a$ | Elemental Analysis Calculated | Found |
|---|---|---|---|---|---|---|
| 2 | C$_{19}$H$_{12}$O$_6$-0.75H$_2$O | 201 | 336.4 | 313 (CI) | C, 66.35; H, 5.41 | C, 66.39; H, 5.27 |
| 3a | C$_{21}$H$_{16}$O$_6$ | 111–114 | 364.4 | 355 (FAB) | C, 71.17; H, 6.26 | C, 70.94; H, 6.37 |
| 3b | C$_{19}$H$_{12}$O$_6$ | 100–101 | 336.4 | 337 (CI) | C, 69.92; H, 5.56 | C, 69.67; H, 5.66 |
| 4 | C$_{23}$H$_{20}$O$_6$ | 90–93 | 392.4 | 397 (CI) | C, 72.70; H, 7.12 | C, 72.61; H, 7.14 |
| 6 | C$_{20}$H$_{20}$O$_7$ | 153–156 | 372.4 | 373 (CI) | C, 64.51; H, 5.41 | C, 64.42; H, 5.44 |
| 7 | C$_{23}$H$_{26}$O$_7$ | 122–123 | | 415 (FAB) | | |
| 8 | C$_{25}$H$_{30}$O$_7$ | 115 | 442.5 | 443 (CI) | C, 67.85; H, 6.83 | C, 67.75; H, 6.84 |
| 10 | C$_{18}$H$_{12}$O$_7$ | oil | | 293 (CI) | | |
| 15 | C$_{18}$H$_{16}$O$_4$-0.25H$_2$O | 160–163 | 296.3 | 297 (CI) | C, 71.86 H, 5.53 | C, 71.93; H, 5.61 |
| 16 | C$_{18}$H$_{14}$O$_4$ | 135–138 | 294.3 | 294 (EI) | C, 73.46; H, 4.80 | C, 74.30; H, 5.27 |
| 19 | C$_{20}$H$_{14}$O$_4$-0.25H$_2$O | 175–178 | 318.3 | 319 (CI) | C, 74.41; H, 4.53 | C, 74.55; H, 4.47 |
| 20 | C$_{21}$H$_{16}$O$_4$ | 148–151 | 332.4 | 333 (CI) | C, 75.89; H, 4.85 | C, 75.83; H, 4.86 |
| 21 | C$_{22}$H$_{18}$O$_4$ | 132 | 346.4 | 347 (CI) | C, 76.30; H, 5.20 | C, 76.03; H, 5.28 |
| 22 | C$_{22}$H$_{16}$O$_4$-0.5H$_2$O | 162–165 | 344.4 | 344 (EI) | C, 74.77; H, 4.85 | C, 74.98; H, 4.77 |

TABLE 1-continued

Physical characterization of flavone, flavanol, and flavanone derivatives.

| Compound | Formula | m.p. (° C.) | M.W. (anhyd) | M.W. (MS)[a] | Elemental Analysis Calculated | Found |
|---|---|---|---|---|---|---|
| 23 | $C_{23}H_{18}O_4$ | 162–165 | 358.4 | 358 (EI) | C, 77.08; H, 5.06 | C, 76.91; H, 5.16 |
| 24 | $C_{19}H_{14}NO_4$ | 150–154 | 320.3 | 320 (CI) | C, 71.24; H, 4.41 | N, 4.37; C, 71.50; H, 4.31; N, 4.37 |

[a]High resolution mass in FAB + mode m/z determined to be within acceptable limits.

TABLE 2

Elemental Analysis of Flavonoid Derivatives 36, 37, 41, 47, and 51.

| Comp. No. | Formula | MW (anhydrous) | Calculated | Found |
|---|---|---|---|---|
| 36 | $C_{19}H_{12}O_6$-0.75$H_2O$ | 336.4 | C, 66.35; H, 5.41 | C, 66.39; H, 5.27 |
| 37 | $C_{21}H_{16}O8$-0.25$H_2O$ | 396.4 | C, 62.92; H, 4.15 | C, 62.76; H, 4.14 |
| 41 | $C_{20}H_{20}O7$-0.25$H_2O$ | 372.4 | C, 63.74; H, 5.48 | C, 63.87; H, 5.80 |
| 47 | $C_{15}H_{14}O_5$ | 274.3 | C, 65.68; H, 6.52 | C, 65.44; H, 5.20 |
| 51 | $C_{14}H_8O_3$—0.1$H_2O$ | 224.2 | C, 74.39; H, 3.66 | C, 74.33; H, 3.81 |

EXAMPLE 16

This Example illustrates the efficacy of some the flavonoid derivatives of the present invention in blocking adenosine receptors. The affinities of the flavonoid derivatives 1–11d were determined using radioligand binding assays, and the results thereof are set forth in Table 3.

TABLE 3

Affinities of flavonoid derivatives in radioligand binding assays at $A_1$, $A_{2a}$, $A_3$ receptors.[a–e]

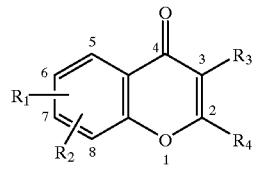

| Compound | $R_1$, $R_2$ | $R_3$ | $R_4$ | $rA^a_1$ | $rA^b_{2a}$ | $hA^c_3$ | $rA_1/hA_3$ |
|---|---|---|---|---|---|---|---|
| 1 (galangin) | 5,7-(OH)$_2$ | OH | Ph | 0.863 ± 0.092 | 0.966 ± 0.164 | 3.15 ± 0.85 | 0.27 |
| 2 | 5,7-(OMe)$_2$ | OMe | Ph | 0.509 ± 0.049 | 6.45 ± 1.48 | 1.21 ± 0.30 | 0.42 |
| 3a | 5,7-(OEt)$_2$ | OEt | Ph | 0.603 ± 0.022 | 3.31 ± 1.24 | 0.364 ± 0.067 | 1.7 |
| 3b | 5-OH, 7-OEt | OEt | Ph | 1.89 ± 0.56 | 63.8 ± 18.8 | 0.748 ± 0.402 | 2.5 |
| 4 | 5,7-(OP$_r$)$_2$ | OPr | Ph | 1.10 ± 0.20 | 3.22 ± 1.31 | 0.317 ± 0.089 | 3.5 |
| 5a morin | 5,7-(OH)$_2$ | OH | 2',4'-(OH)$_2$-Ph | 13.8 ± 3.1 | 17.3 ± 4.1 | 34 ± 4% (10$^{-4}$) | ~0.1 |
| 5b | 5-OH-6-CH=CH—CH(CH$_3$)$_2$—7OMe | CH$_2$CH=CH—CH(CH$_3$)$_2$ | 2',4'-(OH)$_2$-Ph | 9.09 ± 0.91 | d (10$^{-4}$) | 4.59 ± 1.69 | 2.0 |
| 6 | 5,7-(OMe)$_2$ | OMe | 2',4'-(OMe)$_2$-Ph | 27.6 ± 7.5 | 46.7 ± 2.7 | 2.65 ± 0.72 | 10 |
| 7 | 5OH-7-OEt | OEt | 2',4'-(OEt)$_2$-Ph | d (10$^{-4}$) | d (10$^{-4}$) | 4.83 ± 1.40 | >40 |
| 8 | 5,7-(OEt)$_2$ | OEt | 2',4'-(OEt)$_2$-Ph | 32.3 ± 9.1 | 26.8 | 7.27 ± 1.88 | 4.4 |
| 9 | H | OH | 2',4',6'-(OMe)$_3$-Ph | 7.32 ± 1.36 | d (10$^{-4}$) | 50.1 ± 7.8 | 0.15 |
| 10 | 6-OCH$_3$ | OH | C≡C-Ph | d (10$^{-4}$) | d (10$^{-4}$) | 24.0 ± 9.7 | >8 |
| 11a flavone | H | H | Ph | 3.28 ± 0.92 | 3.45 ± 1.16 | 16.9 ± 3.8 | 0.19 |
| 11b[f] | d | Cl | Ph | 15% (10$^{-4}$) | 54.5 ± 26.3 | 0.291 ± 0.042 | >300 |

TABLE 3-continued

Affinities of flavonoid derivatives in radioligand binding assays at $A_1$, $A_{2a}$, $A_3$ receptors.[a–e]

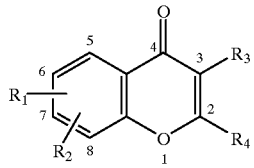

| Compound | $R_1$, $R_2$ | $R_3$ | $R_4$ | $rA^a_1$ | $rA^b_{2a}$ | $hA^c_3$ | $rA_1/hA_3$ |
|---|---|---|---|---|---|---|---|
| 11c[f] | d | Cl | 2'-i-PrO-4'-Me-Ph | 36 ± 12% ($10^{-4}$) | 19 ± 9% ($10^{-4}$) | 0.561 ± 0.129 | ~200 |
| 11d[f] | d | Cl | 2',4',6'-Me$_3$-Ph | 23% ($10^{-4}$) | d ($10^{-4}$) | 5.24 ± 0.52 | ~20 |

[a]Displacement of specific [$^3$H] PIA binding in rat brain membranes, expressed as $K_i$ ± S.E.M. in µM (n = 3–5), or as a percentage of specific binding displaced at 100 µM.
[b]Displacement of specific [$^3$H] CGS 21680 binding in rat striatal membranes, expressed as $K_i$ ± S.E.M. in µM (n = 3–6), or as a percentage of specific binding displaced at 100 µM.
[c]Displacement of specific [$^{125}$I] AB-MECA binding at human $A_3$ receptors expressed in HEK293 cells, in membranes, expressed as $K_i$ ± S.E.M. in µM (n = 2–5), or as a percentage of specific binding displaced at 100 µM.
[d]Displacement of ≤10% of specific binding at the indicated concentration in M.
[e]2,3-trans
[f]Chlorine was introduced in the 3-position using sulfonyl choride in chloroform. Chem. Ind. London, 937 (1980)

EXAMPLE 17

This Example further illustrates the efficacy of the compounds of the present invention in blocking adenosine receptors. The affinities of the flavonoid derivatives 12–16 were determined using radioligand binding assays, and the results thereof are set forth in Table 4.

EXAMPLE 18

This Example further illustrates the efficacy of the compounds of the present invention in blocking adenosine receptors. The affinities of the flavonoid derivatives 17–24 were determined using radioligand binding assays, and the results thereof are set forth in Table 5.

TABLE 4

Affinities of flavonoid derivatives in radioligand binding assays at $A_1$, $A_{2a}$, and $A_3$ receptors.[a–e] $R_2$ = H

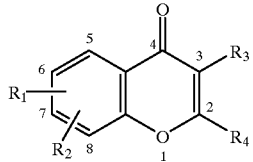

| Compound | $R_3$ | $R_1$ | $R_4$ | $rA^a_1$ | $rA^b_{2a}$ | $hA^c_3$ | $rA_1/hA_3$ |
|---|---|---|---|---|---|---|---|
| 12 flavanone | H | H | Ph | 32.0 ± 4.8 | — | 50.1 ± 27.1 | 0.64 |
| 13 | H | H | 2'-OH-Ph | 2.64 ± 0.56 | 17.6 ± 2.10 | 6.07 ± 1.43 | 0.43 |
| 14[e] | OH | H | 2'-OH-Ph | 91.6 | d ($10^{-4}$) | 27 ± 3% ($10^{-4}$) | <1 |
| 15[e] | OH | 6-OMe | CH=CH-Ph | d ($10^{-4}$) | d ($10^{-4}$) | 21.1 ± 9.9 | >8 |
| 16[e] | OH | 6-OMe | C≡C-Ph | 50.3 ± 17.0 | d ($10^{-4}$) | 8.17 ± 0.43 | 6.2 |

[a]Displacement of specific [$^3$H] PIA binding in rat brain membranes, expressed as $K_i$ ± S.E.M. in µM (n = 3–5), or as a percentage of specific binding displaced at 100 µM.
[b]Displacement of specific [$^3$H] CGS 21680 binding in rat striatal membranes, expressed as $K_i$ ± S.E.M. in µM (n = 3–6), or as a percentage of specific binding displaced at 100 µM.
[c]Displacement of specific [$^{125}$I] AB-MECA binding at human $A_3$ receptors expressed in HEK293 cells, in membranes, expressed as $K_i$ ± S.E.M. in µM (n = 2–5), or as a percentage of specific binding displaced at 100 µM.
[d]Displacement of ≤10% of specific binding at the indicated concentration in M.
[e]2,3-trans

TABLE 5

Affinities of flavonoid derivatives in radioligand binding assays at $A_1$, $A_{2A}$ and $A_3$ receptors.[a–d] $R_3$ = H

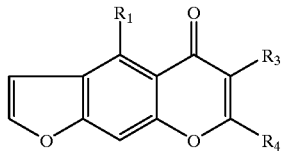

| Compound | $R_1$ | $R_4$ | $rA_1^a$ | $rA_{2a}^b$ | $hA_3^c$ | $rA_1/hA_3$ |
|---|---|---|---|---|---|---|
| 17 visnagin | $OCH_3$ | $CH_3$ | 36 ± 3% ($10^{-4}$) | 42.4 ± 11.9 | 60.0 ± 17.8 | ~2 |
| 18 | $OCH_3$ | CHO | d ($10^{-4}$) | 25 ± 8% ($10^{-4}$) | 88.9 ± 27.1 | >2 |
| 19 | $OCH_3$ | CH=CH-Ph | 32.6 ± 10.5 | 11.5 ± 1.3 | 8.28 ± 2.69 | 0.37 |
| 20 | $OC_2H_5$ | CH=CH-Ph | 35.6 ± 12.7 | 33.8 ± 14.8 | 1.16 ± 0.45 | 31 |
| 21 | $O(CH_2)_2CH_3$ | CH=CH-Ph | 40.0 ± 3.5 | 49.0 | 3.95 ± 1.98 | 10 |
| 22 | $OCH_3$ | CH=CH—CH=CH-Ph | d ($10^{-4}$) | d ($10^{-4}$) | d ($10^{-4}$) | — |
| 23 | $OC_2H_5$ | CH=CH—CH=CH-Ph | d ($10^{-4}$) | 167 | 45.5 ± 10.3 | >4 |
| 24 | $OCH_3$ | CH=NH-Ph | d ($10^{-4}$) | d ($10^{-4}$) | 9.18 ± 2.56 | >20 |

[a]Displacement of specific [$^3$H] PIA binding in rat brain membranes, expressed as $K_i$ ± S.E.M. in $\mu$M (n = 3–5), or as a percentage of specific binding displaced at 100 $\mu$M.
[b]Displacement of specific [$^3$H] CGS 21680 binding in rat striatal membranes, expressed as $K_i$ ± S.E.M. in $\mu$M (n = 3–6), or as a percentage of specific binding displaced at 100 $\mu$M.
[c]Displacement of specific [$^{125}$I] AB-MECA binding at human $A_3$ receptors expressed in HEK293 cells, in membranes, expressed as $K_i$ ± S.E.M. in $\mu$M (n = 2–5), or as a percentage of specific binding displaced at 100 $\mu$M.
[d]Displacement of ≦10% of specific binding at the indicated concentration in M.

EXAMPLE 19

This Example further illustrates the efficacy of the compounds of the present invention in blocking adenosine receptors. The affinities of the flavonoid derivatives 25–39 were determined using radioligand binding assays, and the results thereof are set forth in Table 6.

TABLE 6

Affinities of flavone analogues determined in radioligand binding assays at $A_1$, $A_{2a}$ and $A_3$ receptors.

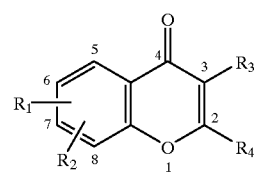

| | | | | $K_2$ ($\mu$M) or % inhibition at the indicated conc. (M) | | |
|---|---|---|---|---|---|---|
| Compound | $R_1$, $R_2$ | $R_3$ | $R_4$ | $(rA_1)^a$ | $(rA_{2a})^b$ | $(hA_3)^c$ |
| 25 | 5-OH | H | Ph | 2.17 ± 0.06 | 6.20 ± 1.24 | 47 ± 12% ($10^{-4}$) |
| 26 | 7-OH | H | Ph | 3.03 ± 0.49 | 2.68 ± 0.68 | 41 ± 7% ($10^{-4}$) |
| 27 | 7-OH | H | 3',4'-diMeO-Ph | 18.8 ± 3.6 | 35.4 ± 7.3 | 32 ± 4% ($10^{-4}$) |
| 28 apigenin | 5,7-diOH | H | 4'-OH-Ph | 3.00 ± 0.29 | 7.58 ± 1.23 | 63 ± 1% ($10^{-5}$) |
| 29 | 5-OH-7-Me | H | 4'-OMe-Ph | 3.40 ± 0.35 | 28.0 ± 7.35 | 6.70 ± 1.78 |
| 30 | 5-OH-7-MeO | H | 4'-OMe-Ph | d ($10^{-4}$) | d ($10^{-4}$) | 69 ± 7% ($10^{-5}$) |
| 31 tetramethyl-scutallarein | 5,6,7-triMe | H | 4'-Me-Ph | 1.29 ± 0.08 | — | 4.48 ± 0.14 |
| 32 hispidulin | 5,7-diOH-6-MeO | H | 4'-OH-Ph | 1.61 ± 0.29 | 6.48 ± 0.65 | 63 ± 2% ($10^{-5}$) |
| 33 cirsimaritin | 5-OH-6,7-diMeO | H | 4'-OH-Ph | 1.20 ± 0.36 | 3.00 ± 0.70 | 1.72 ± 0.19 |
| 34 | 5,7-diAcO | OAc | H-Ph | 11.6 ± 4.4 | 56.5 ± 9.5 | 17.5 ± 2.0 |
| 35 | 5,7-diMeO | OMe | 4'-OMe-Ph | 1.07 ± 0.56 | — | 3.37 ± 1.83 |

TABLE 6-continued

Affinities of flavone analogues determined in radioligand binding assays at $A_1$, $A_{2a}$ and $A_3$ receptors.

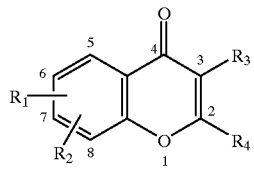

| Compound | $R_1$, $R_2$ | $R_3$ | $R_4$ | $(rA_1)^a$ | $(rA_{2a})^b$ | $(hA_3)^c$ |
|---|---|---|---|---|---|---|
| tetramethyl-kaempferol 36 | 7-OMe | OH | 3',4'-diOH-Ph | — | — | 1.38 ± 0.18 |
| rhamnetin 37 | 5,7-diOH | OH | 3',4'-diOH-Ph | 2.47 ± 0.64 | 6.99 ± 0.89 | — |
| quercetin 38[e] | 5,7-diMeO | OMe | 2',4'-diOMe | 27.6 ± 7.5 | 46.7 ± 2.7 | 2.65 ± 0.72 |
| pentamethyl morin 39 | 5,7-diMeO | OMe | 3',4',5'-triOMe-Ph | d ($10^{-6}$) | — | 16.2 ± 2.2 |
| hexamethyl myricetin | | | | | | |

[a]Displacement of specific [$^3$H] PIA binding in rat brain membranes, expressed as $K_i$ ± S.E.M. in μM (n = 3–5).
[b]Displacement of specific [$^3$H] CGS 21680 binding in rat striatal membranes, expressed as $K_i$ ± S.E.M. in μM (n = 3–6).
[c]Displacement of specific [$^{125}$I] AB-MECA binding at human $A_3$ receptors expressed in HEK-293 cells, in membranes, expressed as $K_i$ ± S.E.M. in μM (n = 2–3), or as a percentage of specific binding displaced at the specified conc. (M).
[d]Displacement of <10% of specific binding at the specified conc. (M).
[e]Also referred to as compound 6 in Table 3.

EXAMPLE 20

This Example further illustrates the efficacy of the compounds of the present invention in blocking adenosine receptors. The affinities of the flavonoid derivatives 40–51 were determined using radioligand binding assays, and the results thereof are set forth in Table 7.

TABLE 7

Figure 8:
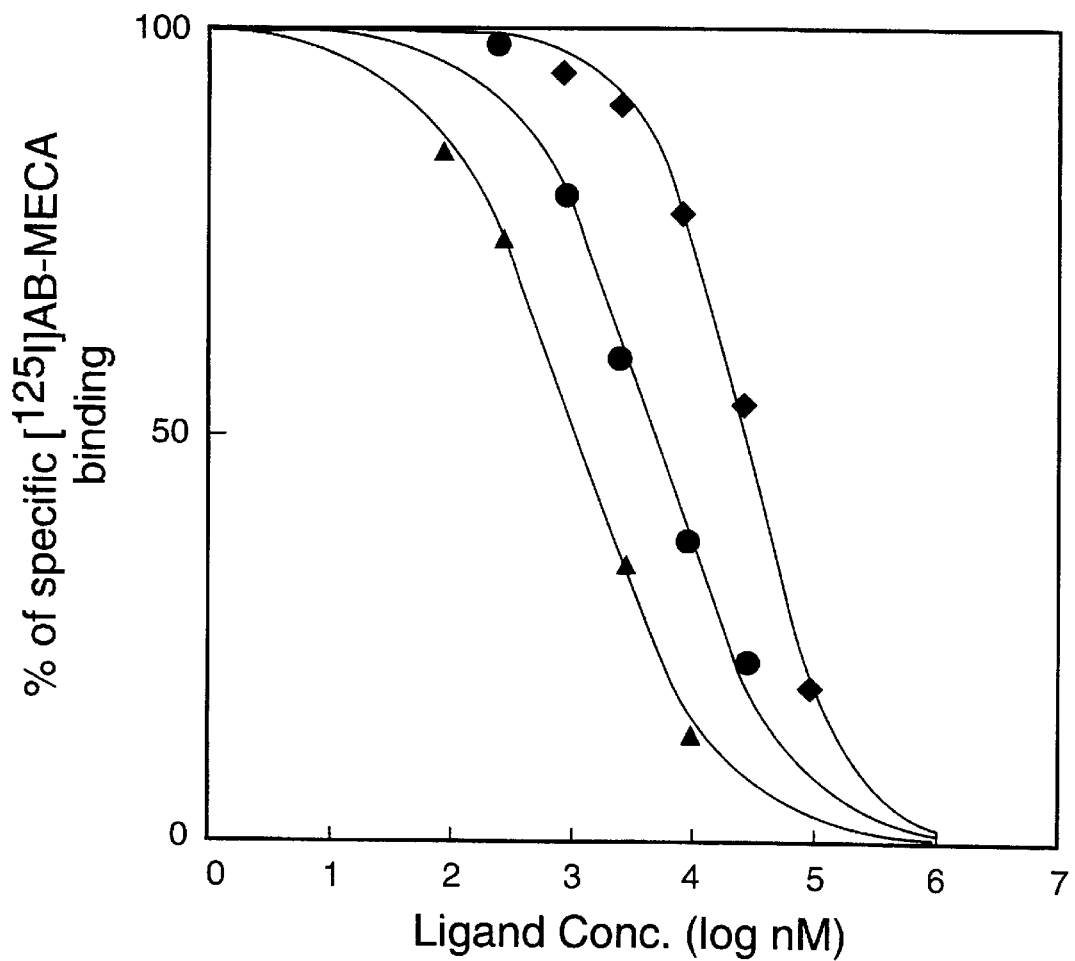
FIG. 8 depicts a representative set of competition curves for inhibition binding of [$^{125}$I]AB-MECA by compounds 12 (triangles), 14 (circles), and 18 (diamonds), at human brain $A_3$ receptors expressed in human HEK-293 cells at 25° C.

Affinities of compounds 40–51, determined in radioligand binding assays at $A_1$, $A_{2a}$ and $A_3$ receptors.[a–d] For structures of the compounds, refer to Figures 8 and 9.

| Compound | $(rA_1)^a$ | $(rA_{2A})^b$ | $(hA_3)^c$ |
|---|---|---|---|
| 40 genistein | 5.0[e] | 36[e] | 20 ± 2% ($10^{-4}$) |
| 41 (±) dihydroquercetin | d ($10^{-5}$) | — | 34.1 ± 10.1 |
| 42 sakuranetin | — | — | 3.40 ± 0.18 |
| 43 α-naphthoflavone | 0.786 ± 0.018 | 1.32 ± 0.43 | 71 ± 2% ($10^{-5}$) |
| 44 β-naphthoflavone | 8.8 ± 3.6 | d ($10^{-4}$) | 12 ± 1% ($10^{-5}$) |
| 45 | 7.10 ± 0.10 | 29.9 ± 10.1 | d ($10^{-4}$) |
| 46 | 7.59 ± 2.14 | 6.98 ± 2.21 | 19 ± 3% ($10^{-4}$) |
| 47 oxogalanthinelactam | 5.55 ± 0.83 | d ($10^{-4}$) | d ($10^{-4}$) |
| 48 | 52.5 ± 3.7 | d ($10^{-4}$) | d ($10^{-4}$) |
| acetylhaemanthamine methiodide 49 | 8.89 ± 2.15 | 84.0 ± 6.9 | 52 ± 6% ($10^{-4}$) |
| 50 hema-toxylin | 3.10 ± 0.60 | 28 ± 2% ($10^{-4}$) | d ($10^{-4}$) |
| 51 arborinine | 12.7 ± 1.2 | 6.47 ± 1.90 | 63 ± 7% ($10^{-4}$) |

[a]Displacement of specific [$^3$H] PIA binding in rat brain membranes, expressed as $K_i$ ± S.E.M. in μM (n = 3–5).
[b]Displacement of specific [$^3$H] CGS 21680 binding in rat striatal membranes, expressed as $K_i$ ± S.E.M. in μM (n = 3–6).
[c]Displacement of specific [$^{125}$I] AB-MECA binding at human $A_3$ receptors expressed in HEK-293 cells, in membranes, expressed as $K_i$ ± S.E.M. in μM (n = 2–3), or as a percentage of specific binding displaced at the specified conc. (M).
[d]Displacement of < 10% of specific binding at the specified conc. (M).
[e]Okajima et al., Biochem. Biophys. Res. Comm., 203, 1488–1495 (1994)

EXAMPLE 21

This Example further illustrates the efficacy of the compounds of the present invention in blocking adenosine receptors. The effects of flavonoid derivatives 3a, 15, and 20 on the $A_3$ agonist-elicited inhibition of adenylyl cyclase were determined, and the results thereof are set forth in Table 8.

TABLE 8

Effects of flavone derivatives 3a, 15, and 20 (50 $\mu$M) on the $A_3$-agonist-elicited inhibition of adenylyl cyclase[a]. Rat (n = 3)

| Compound | % Inhibition | |
|---|---|---|
| | IB-MECA ($10^{-7}$M) | IB-MECA ($10^{-6}$M) |
| galangin (control) | 23.7 ± 5.1 | 35.3 ± 7.2 |
| 3a | 2.2 ± 2.2 | 19.1 ± 7.4 |
| 15 | 25.9 ± 2.4 | 39.2 ± 3.0 |
| 20 | 21.2 ± 3.9 | 40.9 ± 3.7 |

[a]Assayed in membranes from CHO cells stably expressing the rat $A_3$ receptor in the presence of 1 $\mu$M forskolin.

EXAMPLE 22

This Example sets forth the sources for some of the flavonoids and dihydropyridines of the present invention.

Compounds 1, 11a, 12, and 17 were obtained from Fluka, Ronkonoma, N.Y. or from Aldrich, St. Louis, Mo. Compounds 13 and 14 were obtained from Apin Chemicals, Ltd., Oxon, UK. Compound 5a was obtained from K+K Laboratories, Jamaica, N.Y. Compounds 5b (NSC #241010-z), 9 (NSC #78634-f), 11b (NSC #74876-t), 11c (NSC #74899-t), and 11d (NSC #74931-f) were obtained from NCI (Bethesda, Md.).

Compounds 4, 27–34, 43, and 44 were obtained from Fluka, Ronkonoma, N.Y. or from Aldrich, St. Louis, Mo. Compound 36 was obtained from Apin Chemicals, Ltd., Oxon, UK. Compounds 25, 26, 27, and 42 were obtained from K+K Laboratories, Jamaica, N.Y. Compound 40 was obtained from Sigma, Milwaukee Wis. Compound 47 was from Fisher, New York, N.Y. Compounds 46, 48 and 51 (1-hydroxy-2,3-dimethoxy-10-methyl-9(10H)-acridinone) were synthesized as reported in LIterature. Fales et al. *J. Amer. Chem. Soc.*, 77, 5885–5890 (1955); Fales et al. *Chem. & Ind.*, (London), 561–562 (1958); Craig et al., *J. Org. Chem.*, 30, 1573–1576 (1965); Johne et al., *Pharmazie*, 25, 777–779 (1970); Banerjee et al., *Bull. Calcutta Sch. Trop. Med.*, 13, 60 (1965).

R(+)- and S(-)-BAY K 8644, R(-)- and S(+)-niguldipine, nicardipine, nifedipine, nimodipine, and oxidized nifedipine were purchased from Research Biochemicals International (Natick, Mass.).

EXAMPLE 23

Figure 7:
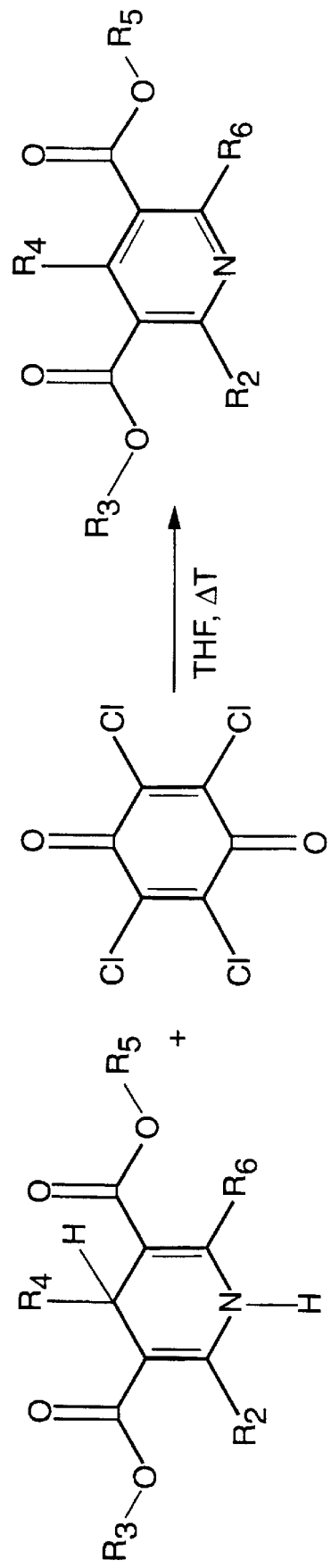
FIG. 7 depicts a method of oxidation of certain 1,4-dihydropyridine derivatives.

This Example illustrates a procedure for the oxidation (see FIG. 7) of 1,4-dihydropyridine-3,5-dicarboxylate esters.

Equimolar amounts (0.25 mmol) of the 1,4-dihydropyridine-3,5-dicarboxylate ester and tetrachloro-1,4-benzoquinone in tetrahydrofuran (2 mL) were mixed and stirred for up to 4 h. The solvent was then evaporated, and products were purified by preparative TLC (silica 60; 1000 mm; Analtech, Del.; 20% ethyl acetate-80% petroleum ether 35–60)

EXAMPLE 24

Figure 6:
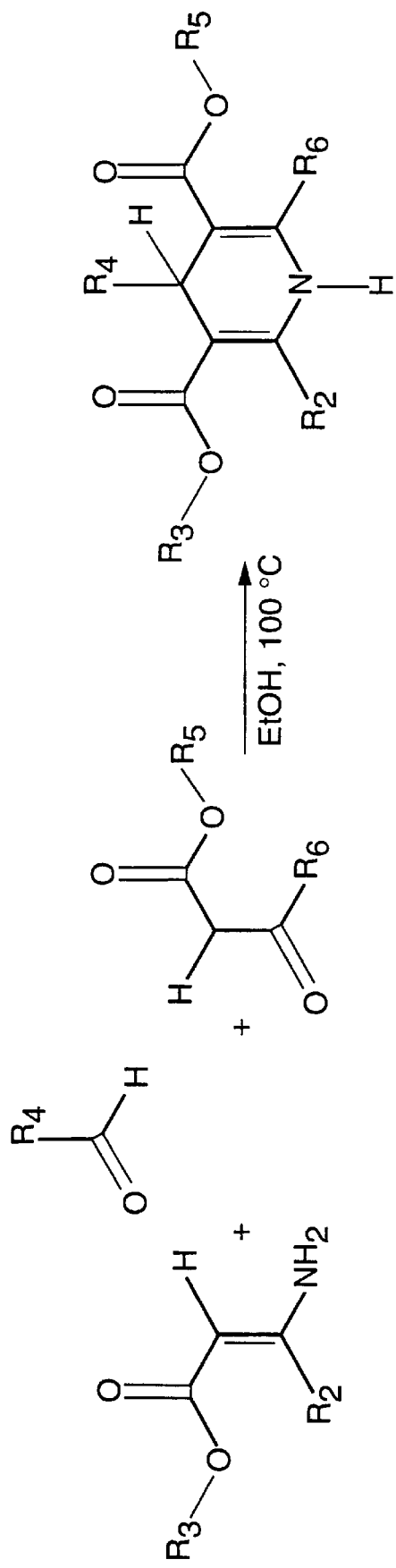
FIG. 6 depicts a method of synthesis of certain 1,4-dihydropyridine derivatives.

This Example illustrates a procedure for the preparation (see FIG. 6) of 1,4-dihydropyridine-3,5-dicarboxylate esters.

Equimolar amounts (0.5 mmol) of the appropriate 3-amino-2-butenoate ester, aldehyde, and 3-ketopropionate ester derivative were dissolved in 5 mL of absolute ethanol. The solution was sealed in a glass tube and heated to 100 C. for at least 24 h, and at most 72 h. The solvent was then evaporated, and products were purified either by crystallization or by preparative TLC (silica 60; 1000 mm; Analtech, Del.; 20% ethyl acetate-80% petroleum ether 35–60). From the moment the reactants were sealed into the glass tube, all procedures were performed under nitrogen and low-light conditions to prevent oxidation of the products. The products were shown to be pure by TLC.

Following the above procedure, several 1,4-dihydropyridine-3,5-dicarboxylate esters were prepared. The compounds thus prepared and their physical characterization data are set forth below. Additional characterization data are set forth in Table 9.

3-Methyl-5-ethyl 2,4,6-trimethyl-1,4(R,S)-dihydropyridine-3,5-dicarboxylate (52)

Yield: 98.2% (recrystallized from MeOH); 1H NMR (d-CHCl3) d 0.98 (d, 3H, 4-$CH_3$, J=6.7 Hz); 1.31 (t, 3H, 5-methyl, J=7.2 Hz); 2.28 (s, 6H, 2- & 6-$CH_3$); 3.73 (s, 3H, 3-methyl); 3.83 (q, 1H, H-4, J=6.4 Hz); 4.13–4.26 (m, 2H, 5-methylene); 5.51 (wide signal, 1H, H-1). Molecular mass calcd.: 253.131 found: m/z=271 (M+NH4+, base), 254 (M+H+), CI.

3-Methyl-5-ethyl-2,6-dimethyl-4-ethyl-1,4(R,S)-dihydropyridine-3,5-dicarboxylate (56)

Yield: 50.5%, recrystallized from MeOH. 1H NMR (d6-DMSO) d 0.63 (t, 3H, 4-methyl, J=7.4 Hz); 1.18 (t, 3H, 5-methyl, J=7.1 Hz); 2.19 (s, 6H, 2- & 6-$CH_3$); 3.58 (s, 3H, 3-methyl); 3.73 (t, 1H, H-4, J=5.4 Hz); 4.00–4.13 m, 4H, 4- & 5-methylene). Molecular mass calcd.: 267.147 found: m/z=285 (M+NH4+, base), 268 (M+H+), CI.

3-methyl,5-ethyl 2,6-dimethyl-4-propyl-1,4(R,S)-dihydropyridine-3,5-dicarboxylate (57)

Yield: 73.3%, recrystallized from MeOH. 1H NMR (d6-DMSO) d 0.77 (t, 3H, 4-methyl, J=6.7 Hz); 1.12 (wide signal, 4H, 4a- & 4b-methylene); 1.19 (t, 3H, 5-methyl, J=7.2 Hz); 2.19 (s, 6H, 2- & 6-$CH_3$); 3.59 (s, 3H, 3-methyl); 3.76 (t, 1H, H-4, J=5.2 Hz); 4.07 (q, 2H, 5-methylene, J=6.6 Hz). Molecular mass calcd.: 281.163 found: m/z=299 (M+NH4+, base), 282 (M+H+), CI. Elemental analysis: ($C_{15}H_{23}N_{104}$)C,H,N.

3-methyl-5-ethyl-2,6-dimethyl-4-(2(R,S),6-dimethyl-hexen-5-yl)-1,4(R,S)-dihydropyridine-3,5-dicarboxylate (58)

Yield: 33.4%, preparative TLC. 1H NMR (d-$CHCl_3$) d 0.91 (double d, 3H, 4-(2-$CH_3$), J1=5.8 Hz, J2=24.0 Hz); 1.30 (m, 7H); 1.63 (d, 6H, 4-(6- & 7-$CH_3$), J=25.4 Hz); 2.28 (d, 6H, 2- & 6-$CH_3$, J=7.8 Hz); 3.71 (s, 3H, 3-methyl); 3.97 (t, 1H, H-4, J=7.2 Hz); 4.11–4.24 (m, 2H, 5-methylene); 5.07 (t, 1H, 4-(2-methyne), J=6.5 Hz); 5.71 (wide signal, 1H, H-1). Molecular mass calcd.: 363.241 found: m/z=381 (M+NH4+, base), 364 (M+H+), CI.

3-methyl,5-ethyl-2,6-dimethyl-4-phenyl-1,4(R,S)-dihydropyridine-3,5-dicarboxylate (59)

Yield: 78.6%, recrystallized from MeOH. 1H NMR (d6-DMSO) d 1.11 (t, 3H, 5-methyl; J=6.4 Hz); 2.23 (s, 6H, 2- & 6-CH3); 3.51 (s, 3H, 3-methyl); 3.97 (m, 2H, 5-methylene); 4.84 (s, 1H, H-4); 7.08–7.20 (m, 5H, 4-phenyl). Molecular mass calcd.: 315.147 found: m/z=333 (M+NH4+, base), 316 (M+H+), CI.

3-methyl-5-ethyl-2,6-dimethyl-4-(3-nitrophenyl)-1,4 (R,S)-dihydropyridine-3,5-dicarboxylate (nitrendipine) (61)

Yield: 88.3%, preparative TLC. 1H NMR (d-CHCl$_3$) d 1.25 (t, 3H, 5-methyl, J=5.4 Hz); 2.39 (s, 6H, 2- & 6-CH3); 3.66 (s, 3H, 3-methyl); 4.13 (m, 2H, 5-methylene); 5.11 (s, 1H, H-4); 5.71 (wide signal, 1H, H-1); 7.39 (t, 1H, H-5', J=8.0 Hz); 7.65 (d, 1H, H-6', J=7.7 Hz); 8.02 (d, 1H, H-4', J=7.8 Hz); 8.13 (s, 1H, H-2'). Molecular mass calcd.: 360.132 found: m/z=378 (M+NH4+, base), 361 (M+H+), CI. Elemental analysis: (C$_{18}$H$_{20}$N$_2$O$_6$)C,H,N.

3-methyl-5-ethyl-2,6-dimethyl-4-(4-nitrophenyl)-1,4 (R,S)-dihydropyridine-3,5-dicarboxylate (67)

Yield: 68.1%, recrystallized from MeOH. 1H NMR (d6-DMSO) d 1.11 (t, 3H, 5-methyl, J=7.2 Hz); 2.26 (s, 6H, 2- & 6-CH3); 3.52 (s, 3H, 3-methyl), 4.00 (m, 2H, 5-methylene); 4.96 (s, 1H, H-1); 7.39 (d, 2H, H-2' & H-6', J=8.7 Hz); 8.09 (d, 2H, H-3' & H-5', J=8.7 Hz). Molecular mass calcd.: 360.132 found: m/z=378 (M+NH4+, base), 361 (M+H+), CI.

3-methyl-5-ethyl-2,6-dimethyl-4-(2-α,α,α-trifluoromethylphenyl)-1,4(R,S)-dihydropyridine-3,5-dicarboxylate (68)

Yield: 45.6%, preparative TLC. 1H NMR (d6-DMSO) d 1.05 (m, 3H, 5-methyl); 2.21 (s, 6H, 2- & 6-CH$_3$); 3.44 (s, 3H, 3-methyl); 3.84–4.10 (m, 2H, 5-methylene); 5.38 (s, 1H, H-4); 7.31 (t, 1H, J=7.3 Hz); 7.51 (m, 3H, 4-phenyl). Molecular mass calcd.: 383.134 found: m/z=401 (M+NH4+, base), 384 (M+H+), CI.

3-methyl-5-ethyl-2,6-dimethyl-4-(4-methoxyphenyl)-1,4(R,S)-dihydropyridine-3,5-dicarboxylate (71)

Yield: 61.8%, preparative TLC. 1H NMR (d-CHCl$_3$) d 1.23 (t, 3H, 5-methyl, J=7.8 Hz); 2.34 (s, 6H, 2- & 6-CH$_3$); 3.65 (s, 3H, 4'-OCH$_3$); 3.76 (s, 3H, 3-methyl); 4.07–4.14 (m, 2H, 5-methylene); 4.94 (s, 1H, H-4); 5.57 (wide signal, 1H, H-1); 6.76 (d, 2H, H-2' & H-6', J=8.5 Hz); 7.20 (d, 2H, H-3' & H-5', J=8.6 Hz). Molecular mass calcd.: 345.158 found: m/z=363 (M+NH4+, base), 346 (M+H+), CI.

3-methyl-5-ethyl-2,6-dimethyl-4-(4-hydroxy,3-methoxyphenyl)-1,4(R,S)-dihydropyridine-3,5-dicarboxylate (72)

Yield: 79.6%, recrystallized from MeOH. 1H NMR (d6-DMSO) d 1.13 (t, 3H, 5-methyl, J=7.4 Hz); 2.21 (s, 6H, 2- & 6-CH$_3$); 3.52 (s, 3H, 3'-OCH3), 3.66 (s, 3H, 3-methyl); 3.96–4.01 (m, 2H, 5-methylene); 4.74 (s, 1H, H-4); 6.49 (t, 1H, H-6', J=3.9 Hz); 6.58 (d, 1H, H-5', J=7.9 Hz); 6.66 (s, 1H, H-2'). Molecular mass calcd.: 361.153 found: m/z=379 (M+NH4+, base), 362 (M+H+), CI.

3-methyl-5-ethyl-2,6-dimethyl-4-[3,4-(methylenedioxy)phenyl]-1,4(R,S)-dihydropyridine-3,5-dicarboxylate (73)

Yield: 63.0%, preparative TLC. 1H NMR (d-CHCl$_3$) d 1.24 (t, 3H, 5-methyl, J=7.3 Hz); 2.33 (s, 6H, 2- & 6-CH3); 3.66 (s, 3H, 3-methyl); 3.73 (s, 1H, H-4); 4.09–4.22 (m, 2H, 5-methylene); 4.92 (s, 2H, 3',4'-methylenedioxy); 5.57 (wide signal, 1H, H-1); 5.89 (s, 1H, H-2'); 6.66 (d, 1H, H-5', J=8.1 Hz); 6.75 (d, 1H, H-6', J=7.9 Hz). Molecular mass calcd.: 359.137 found: m/z=377 (M+NH4+, base), 360 (M+H+), CI.

3-methyl-5-ethyl-2,6-dimethyl-4-[2-phenyl-(trans)-vinyl]-1,4(R,S)-dihydropyridine-3,5-dicarboxylate (75)

Yield: 87.9%, recrystallized from MeOH. 1H NMR (d-CHCl$_3$) d 1.31 (t, 3H, 5-methyl, J=7.1 Hz); 2.34 (s, 6H, 2- & 6-CH$_3$); 3.74 (s, 3H, 3-methyl); 4.14–4.28 (m, 2H, 5-methylene); 4.63 (d, 1H, H-4, J=5.4 Hz); 5.60 (wide signal, 1H, H-1); 6.19 (t, 1H, 4-(H-1 vinylidene), J=6.0 Hz); 7.18 (d, 1H, 4-(H-2 vinylidene), J=6.6 Hz); 7.24–7.34 (m, 5H, 4-phenyl)). Molecular mass calcd.: 341.163 found: m/z=359 (M+NH4+, base), 342 (M+H+), CI.

3,5-diethyl-2,4-dimethyl-6-phenyl-1,4(R,S)-dihydropyridine-3,5-dicarboxylate (78)

Yield: 53%, recrystallized from petroleum ether (35–60). 1H NMR (d-CHCl$_3$): d 0.89 (t, 3H, 3-methyl, J=7.4 Hz); 1.14 (d, 3H, 5-methyl, J=7.4 Hz); 1.31 (t, 3H, J=7.0 Hz); 2.3 (s, 3H, CH$_3$); 3.94 (m, 3H); 4.23 (m, 2H); 7.28–7.41 (m, 5H, C6H5). Molecular mass calcd.: 329.163 found: m/z=347 (M+NH4+, base), 330 (M+H+), CI.

3,5-diethyl-2,4-dimethyl-6-butyl-1,4(R,S)-dihydropyridine-3,5-dicarboxylate (77)

The structure was confirmed by HNMR and mass spectrometry.

3-methyl,5-(2-methoxy)ethyl 2,4,6-trimethyl-1,4(R,S)-dihydropyridine-3,5-dicarboxylate (53)

Yield: 53.0%; 1H NMR (d-CHCl$_3$) d 0.99 (d, 3H, 4-CH$_3$, J=6.7 Hz); 2.28 (s, 6H, 2- & 6-CH$_3$); 3.41 (s, 3H, 5-methoxy); 3.66 (t, 2H, 5-(2-methylene), J=4.9 Hz); 3.73 (s, 3H, 3-methyl); 3.85 (q, 1H, H-4, J=6.5 Hz); 4.22–4.38 (m, 2H, 5-(1-methylene)); 5.54 (wide signal, 1H, H-1). Molecular mass calcd.: 283.142 found: m/z=301 (M+NH4+, base), 284 (M+H+), CI.

3-methyl,5-benzyl 2,4,6-trimethyl-1,4(R,S)-dihydropyridine-3,5-dicarboxylate (54)

Yield: 70.5%; 1H NMR (d-CHCl$_3$) d 0.98 (d, 3H, 4-CH$_3$, J=5.0 Hz); 2.28 (s, 6H, 2- & 6-CH$_3$); 3.72 (s, 3H, 3-methyl); 3.89 (q, 1H, H-4, J=6.5 Hz); 5.21 (q, 2H, 5-methylene, J=14.8 Hz); 5.54 (wide signal, 1H, H-1); 7.30–7.41 (m, 5H, 5-phenyl). Molecular mass calcd.: 315.147 found: m/z=333 (M+NH4+, base), 316 (M+H+), CI.

3,5-Diethyl 2,6-dimethyl-4-(2-thienyl)-1,4-(±)-dihydropyridine-3,5-dicarboxylate (114)

$^1$H NMR (CDCl$_3$): α 1.27(t, 6H, J=7.75 Hz, 3 and 5-CH$_2$CH$_3$), 2.3 (S, 6H, 2 and 6-CH$_3$), 4.17 (m, 4H, 3 and 5-OCH$_2$) 5.35 (s, 1H, 4-H), 5.92 (br, 1H, NH), 6.8 (d, 1H, J=3.9 Hz, 3'-H), 6.85 (m, 1H, 4'-H), 7.06 (d, 1H, j+4.89 Hz, 5'-H).

3,5-Diethyl 2-methyl-4-phenylethynyl-6-trifluoromethyl-1,4-(±)-dihydropyridine-3,5-dicarboxylate $^1$H NMR (CDCl$_3$): δ 1.32 (m, 6H, 3 & 5-CH$_2$CH$_3$); 2.35 (S, 3H, 7-CH$_3$), 4.20–4.38 (m, 4H, 3 & 5-OCH$_2$) 4.84(s, 1H, 4-H); 6.29 (br, 1H, NH); 7.25–7.35 (m, 5H, C$_6$H$_5$). MS (EI: m/z 415 (M)$^+$; 386(M-C$_2$H$_5$)$^+$; 342(M-CO$_2$C$_2$H$_5$)$^+$, base.

3,5-Diethyl 2-methyl-4,6-diphenyl-1,4-(±)-dihydropyridine-3,5-dicarboxylate (110)

$^1$H NMR (CDCl$_3$): α 0.84 (t, 3H, J=6.83 Hz, 5-CH$_2$CH$_3$), 1.24 (t, 3H, J=6.84 Hz, 3-CH$_2$CH$_3$), 2.36 (s, 3H, 2-CH$_3$), 3.84 (m, 2H, 5-OCH$_2$), 4.12 (q. 2H, J=6.83 Hz, 3-OCH$_2$), 5.12 (s, 1H, 4-H), 5.76 (br, 1H, NH), 7.18–7.44 (m, 10H, 4 and 6C$_6$H$_5$).

3,5-Diethyl 2-methyl-4-(2-pyridyl)-6-phenyl-1,4-(±)-dihydropridine-3,5-dicarboxylate (111)

$^1$H NMR (CDCl$_3$): α 0.81 (t, 3H, J=6.84 Hz, 5-CH$_2$CH$_3$), 1.22 (t, 3H, J=6.83 HZ, 3-CH$_2$CH$_3$), 3.82 (m, 2H,-5-OCH$_2$), 4.11 (q, 2H, J=6.84 Hz, 3-OCH$_2$), 5.25 (s, 1H, 4-H), 5.88(br, 1H, NH), 7.08–7.56 (m, 3H, pyridyl 3',4', and 5'-H), 7.37 (m, 5H, 6-C$_6$H$_5$), 8.55 (d, 1H, J=4.89, pyridyl 6'-H).

3,5-Diethyl 2-methyl-4-(3-pyridyl)-6-phenyl-1,4-(±)-dihydropridine-3,5-dicarboxylate (112)

$^1$H NMR (CDCl$_3$): α 0.84 (t, 3H, J=6.83 Hz, 5-CH$_2$CH$_3$), 1.24 (t, 3H, J=6.84 Hz, 3-CH$_2$CH$_3$), 2.38 (s, 3H, 2-CH$_3$), .3.83 (m, 2H, 5-OCH$_2$), 4.11 (q, 2H, J=6.84 Hz, 3-OCH$_2$), 5.09(S, 1H, 4-H), 6.43 (BR, 1H, NH), 7.2–7.7 (m, 2H, pyridyl 4' and 5'-H), 7.3–7.4 (m, 5H, 6-C$_6$H$_5$), 8.33 (d, 1H, pyridyl 6'-H), 8.64 (s, 1H, pyridyl 2"-H).

3.5-Diethyl 2-methyl-4-(4-pyridyl)-6-phenyl-1,4(±)-dihydropyridine-3.5-dicarboxylate (113)

$^1$H NMR (CDCl$_3$): α 0.83 (t, 3H, J=6.84 Hz, 5-CH$_2$CH$_3$), 1.24 (t, 3H, J=6.84 HZ, 3-CH$_2$CH$_3$), 2.4. (s, 3H,-2-CH$_3$), 3.84 (m, 2H, 5-OCH$_2$), 4.12 (q, 2H, J=7.81 Hz, 3-OCH$_2$), 5.12 (s, 1H, 4-H), 6.35 (br, 1H, NH), 7.3–7.4 (m, 7H, 6-C$_6$H$_5$ and pyridyl 3' and 5'-H), 8.42 (d, 2H, J=5.86 Hz, pyridyl 2' and 6'-H).

3,5-Diethyl 2-methyl-4-(2-benzofuryl)-6-phenyl-1,4-(±)-dihydropridine-3,5-dicarboxylate (116)

$^1$H NMR (CDCl$_3$): α 0.89 (t, 3H, J=6.84 Hz, 5-CH$_2$CH$_3$), 1.31 (t, 3H, J=6.84 HZ, 3-CH$_2$CH$_3$), 2.39 (s, 3H,, 2-CH$_3$), 4.21 (m, 2H, 3-OCH$_2$), 5.48 (s, 1H, 4-H), 5.96(br, 1H, NH), 648 (s, 1H, benzofuryl 3'-H), 7.1–7.5 (m, 9H, 6-C$_6$H$_5$ and benzofuryl 4', 5', 6' and 7'-H).

3,5-Diethyl 2-methyl-4-(3-methyl phenylethynyl)-6-phenyl-1,4-(±)-dihydropyridine-3,5-dicarboxylate (120)

$^1$H NMR (CDCl$_3$): α 0.95 (t, 3H, J=6.84 Hz, 5-CH$_2$CH$_3$), 1.35 (t, 3H, J=6.84 Hz, 3-CH$_2$CH$_3$), 2.29 (s, 3H,-3'CH$_3$), 2.36 (s, 3H, 2-CH$_3$), 4.0 (m 2H, 5-OCH$_2$), 4.3 (m, 2H, 3-OCH$_2$), 5.11 (s, 1H, 4-H), 5.92 (br, 1H, NH), 7.0–7.43 (m, 9H, 4-C$_6$H$_4$ and 6-C$_6$H$_5$).

3-Ethyl 5-benzyl 2-ethyl-4-phenylethynyl-6-phenyl-1,4-(±)-dihydropridine-3,5-dicarboxylate $^1$H NMR (CDCl$_3$): δ 1.22 (t, J=6.9 Hz, 3H, 2-CH$_2$CH$_3$); 1.34 (t, J=6.9 Hz, 3H, 3-CH$_3$CH$_2$); 2.55, 3.01 (2m2H, 2-CH$_2$CH$_3$); 4.25 (m, 2H, 3-OCH$_2$); 5.06 (AB, J=12.7 Hz, 2H, 5-OCH$_2$); 5.18 (s, 1H, 4-H); 5.95 (br, 1H, NH); 7.05–7.39 (m, 15H, 3×C$_6$H$_5$) MS (EI): m/z 491 (M)$^+$; 462 (M-C2H5)$^+$; 418 (M-CO$_2$C$_2$H$_5$)+;356 (M-CO$_2$CH$_2$C$_6$H$_5$)$^+$, base.

General Procedure for the Preparation of Compounds 122a–g, 125 and 126

Compound 139 (0.2 mmol) was dissolved in dry acetone (10 mL), anydrous potassium carbonate (0.5 g) and phenylethyl bromide or phenylpropyl bromide (5 eq.) were added, and the mixture was refuxed for 2 h. The solution were filtered and evaporated, and the residue were separated with preparative TLC plates to give products which were carried out for deprotection to afford 125 and 126 respectively.

3-Ethyl 5-(2-methylbenzyl)-4-phenylethynyl-6-phenyl-1,4(±)-dihydropyridine-3,5-dicarboxylate (122a)

$^1$H NMR (CDCl$_3$): α 1.34 (t, 3H, J=6.84 Hz, 3-CH$_2$CH$_3$), 2.16 (s, 3H, 2'-CH$_3$), 2.37 (s, 3H, 2-CH$_3$), 4.26 (m, 2H, 3-OCH$_2$), 5.04 (AB, 2H, J=12.7 Hz, 5-OCH$_2$), 5.17 (s, 1H, 4-H), 5.92 (br, 1H, NH), 7.06–7.36 (m, 14H, 4-C$_6$H$_5$, 5-C$_6$H$_4$, and 6-C$_6$H$_5$).

3-Ethyl 5-(3-methylbenzyl)-4-phenylethynyl-6-phenyl-1,4(±)-dihydropyridine-3,5-dicarboxylate (122b)

$^1$H NMR (CDCl$_3$): α 1.34 (t, 3H, J=6.84 Hz, 3-CH$_2$CH$_3$), 2.25(s, 3H, 2'-CH$_3$), 2.36 (s, 3H, 2-CH$_3$), 4.3 (m, 2H, 3-OCH$_2$), 4.99 (AB, 2H, J=12.7 Hz, 5-OCH$_2$), 5.18 (s, 1H, 4-H), 5.91 (br, 1H, NH), 6.88–7.39 (m, 14H, 4-C$_6$H$_5$, 5-C$_6$H$_4$, and 6-C$_6$H$_5$).

3-Ethyl 5-(4-methylbenzyl)-4-phenylethynyl-6-phenyl-1,4(±)-dihydropyridine-3.5-dicarboxylate (122c)

$^1$H NMR (CDCl$_3$): α 1.34 (t, 3H, J=6.84 Hz, 3-CH$_2$CH$_3$), 2.37 (s, 3H, 2-CH$_3$), 4.3 (m, 2H, 3-OCH$_2$), 4.99 (AB, 2H, J=12.7 Hz, 5-OCH2), 5.17 (s, 1H, 4-H), 5.86 (br, 1H, NH), 7.0–7.4 (m, 14H, 4-C$_6$H$_5$, 5-C$_6$H$_4$, and 6-C$_6$H$_5$).

3-Ethyl 5-(4-trifluoromethylbenzyl)-4-phenylethynyl-6-phenyl-1,4(±)-dihydropyridine-3,5-dicarboxylate (122d)

$^1$H NMR (CDCl$_3$): α 1.35 (t, 3H, J=6.84 Hz, 3-CH$_2$CH$_3$), 2.37 (s, 3H, 2-CH$_3$), 4.3 (m, 2H, 3-OCH$_2$), 5.15 (AB, 2H, J=13.7 Hz, 5-OCH$_2$), 5.18 (s, 1H, 4-H), 5.94 (br, 1H, NH), 7.13–7.45 (m, 14H, 4-C$_6$H$_5$, 5-C$_6$H$_4$, and 6-C$_6$H$_5$).

3-Ethyl 5-(3-nitrobenzyl)-4-phenylethynyl-6-phenyl-1,4(±)-dihydropyridine-3,5-dicarboxylate (122f)

$^1$H NMR (CDCl$_3$): α 1.35 (t, 3H, J=6.84 Hz, 3-CH2CH3), 2.38 (s, 3H, 2-CH$_3$), 4.3 (m, 2H, 3-OCH2), 5.15 (AB, 2H, J=13.7 Hz, 5-OCH$_2$), 5.17 (s, 1H, 4-H), 5.94 (br, 1H, NH), 7.3–8.1 (m, 14H, 4-C$_6$H$_5$, 5-C$_6$H$_4$, and 6-C$_6$H$_5$).

3-Ethyl 5-(4-nitrobenzyl)-4-phenylethynyl-6-phenyl-1,4(±)-dihydropyridine-3.5-dicarboxylate (122 g)

$^1$H NMR (CDCl$_3$): α 1.36 (t, 3H, J=6.84 Hz, 3-CH$_2$CH$_3$), 2.38 (s, 3H, 2-CH$_3$), 4.3 (M, 2H, 3-OCH$_2$), 5.12 (AB, 2H, J=12.7 Hz, 5-OCH$_2$), 5.20 (s, 1H, 4-H), 5.94 (br, 1H, NH), 7.1–8.0 (m, 14H, 4-C$_6$H$_5$, 5-C$_6$H$_4$, and 6-C$_6$H$_5$).

3-Propyl 5-benzyl 2-methyl-4-phenylethynyl-6-phenyl-1,4-(±)-dihydropyridine-3,5-dicarboxylate (124)

$^1$H NMR (CDCl$_3$): δ 1.01 (t, J=6.9 Hz, 3H, 3-CH$_2$CH$_3$), 1.73 (M, 2H, 3-CH$_3$CH$_2$); 2.37 (s, 3H, 2-CH$_3$); 4.15 (m, 2H, 3-OCH$_2$); 5.06 (AB, J=12.7 Hz, 2H, 5-OCH$_2$); 5.20(s, 1H, 4-H); 5.88(br, 1H, NH); 7.07–7.37 (m, 15H, 3×C$_6$H$_5$) MS (EI: m/z 491 (M)+'448 (M-C$_3$H$_7$)$^+$; 404(M-CO$_2$C$_2$H$_7$)$^+$; 356(M-CO$_2$CH$_2$C$_6$H$_5$)$^+$, base.

3-Ethyl 5-phenylethyl 2-methyl-4-phenylethynyl-6-phenyl-1,4-(±)-dihydropyridine-3,5-dicarboxylate (125)

$^1$H NMR (CDCl$_3$): δ 1.36(t, J=6.8 Hz, 3H, 3-CH$_2$CH$_3$); 2.37 (s, 3H, 2-CH$_3$); 2.69 (t, J=6.8 Hz, 2H, 5-CH$_2$C$_6$H$_5$);

4.15 (m, 2H, 3-OCH$_2$); 4:30 (m, 2H, 5-OCH$_2$); 5.11 (s, 1H, 4-H); 5.87 (br, 1H, NH); 7.10–7.41 (m, 15H, 3×C$_6$H$_5$) MS (EI): m/z 491 (M)$^+$; 462 (M-C$_2$H$_5$)$^+$; 418(M-CO$_2$C$_2$H$_5$)$^+$; 342 (M-CO$_2$ (CH$_2$)$_2$(C$_6$H$_5$)$^+$.

3-Ethyl 5-phenylpropyl 2-methyl-4-phenylethynyl-6-phenyl-1,4-(±)-dihydropyridine-3,5-dicarboxylate (126)

$^1$H NMR (CDCl$_3$): δ 1.30(t,J=6.8 Hz, 3H, 3-CH$_2$CH$_3$); 1.65 (m, 2H, 5-CH$_2$CH$_2$CH$_2$); 2.35 (S, 3H, 2-CH$_3$); 2.40 (m, 2H, 5-CH$_2$C$_6$H$_5$); 398 (m, 2H, 3-OCH$_2$); 4.26 (m, 2H, 5-OCH$_2$); 5.14 (S, 1H, 4-H); 5.85 (BR, 1Hh NH); 7.20–7.41 (M, 15H, 3×C$_6$H$_5$). MS (EI): m/z 505(M)$^+$; 476 (M-C$_2$H$_5$)+; 432(M-CO$_2$C$_2$H$_5$)$^+$; 342(M-CO$_2$(CH$_2$)$_3$C$_6$H$_5$)$^+$.

3-Ethyl 5-t-butyl 2-methyl-4-phenylethynyl-6-phenyl-1,4-(±)-dihydropyridine-3,5-dicarboxylate (127)

$^1$H NMR (CDCl$_3$): δ 1.25(t,J=7.1 Hz, 3H, 3-CH$_2$CH$_3$); 1.31 (s,9H, C(CH$_3$)$_3$); 2.31 (s, 3H, 2-CH$_3$); 4.22 (m, 2H, 3-OCH$_2$); 4.94 (s, 1H, 4-H ); 5.56 (br, 1H, NH); 7.21–7.34 (m, 10H, 2×C$_6$H$_5$). MS (EI: m/z 505 (M)$^+$; 476 (M-C$_2$H$_5$)$^+$; 432 (M-CO$_2$C$_2$H$_5$)+; 342 (M-CO$_2$(CH$_2$)$_3$C$_6$H$_5$)$^+$.

3-(2-Methoxy-2-phenyl)-ethyl 5-Ethyl 2-methyl-4-phenylethynyl-6-phenyl-1.4-(±)-dihydropyridine-3,5-dicarboxylate (128)

$^1$H NMR (CDCl$_3$): δ 0.91&1.00((2t,J=6.8 Hz, 3H, 5-CH$_2$CH$_3$); 2.35 (s, 3H, 2-CH$_3$); 4.00 (m, 2H, 5-OCH$_2$); 4.35 (m, 1H, 3-CH); 4.50 (m, 2H, 3-OCH$_2$); 5.05 (s, 1H, 4-H) 5.82 (br, 1H, NH); 7.21–7.41 (m, 10H, 2×C$_6$H$_5$). MS (CI/NH$_3$): m/z 539 (M=NH$_4$)$^+$.

3-Ethyl 5-(2-trimethylsilyl)-ethyl 2-methyl-4-phenylethynyl-6-phenyl-1,4-(±)-dihydropyridine-3,5-dicarboxylate (129)

$^1$H NMR (CDCl$_3$): δ 0.03(s,9H, Si(CH$_3$)$_3$); 0.79(t, J=8.8 Hz, 2H, CH$_2$Si)); 1.41 (t, J=6.8 Hz, 3H, 3-CH$_2$CH$_3$); 240 (s, 3H, 2-CH$_3$); 4.10(t, J=8.8 Hz, 2H, 5-OCH$_2$); 4.31(m, 2H, 3-OCH$_2$); 5.15 (s 1H, 4-H); 5.87 (br, 1H, NH); 7.28–7.46 (m, 10H, 2×C$_6$H$_5$). MS (CI/NH$_3$): m/z

3-Ethyl 5-thioethyl 2-methyl-4-phenylethynyl-6-phenyl-1,4(±)-dihydropyridine-3,5-dicarboxylate (130a)

Triethylamine (20 mg) was added to a mixture of compound 135 (90 mg, 0.2 mmol), diphenyl phosphoryl azide (56 mg, 0.2 mmol), and ethanethiol (20 mg, 0.3 mmol) in DMF (1 mL) with stirring and ice cooling. The mixture was stirred at room temperature for 3 hr, diluted with dichloromethane (20 mL), washed with water (10 mL×2), dried with sodium sulfate. The solvent was evaporated and the residue was carried out for deprotection with 1NHCl to give 15 mg of product.

$^1$HMR (CDCl$_3$): 1.15(t, J=6.9 Hz, 3H, 5-CH$_2$CH$_3$); 1.28 (t, J=6.8 Hz, 3H, 3-CH$_2$CH$_3$): 2.37 (s, 3H, 2-CH$_3$); 2.82(m, 2H, 5-SCH$_2$); 4.31 (m, 2H, 3-OCH$_2$): 5.23 (s, 1H, 4-H): 5.95 (br, 1H, NH); 7.24–746(m, 10H, 2×C$_6$H$_5$). MS (CI/NH$_3$); m/z

3-Ethoxycarbonyl-2-methyl-4-phenylethynyl-6-phenyl-1,4(±)-dihydropyridine-5-carboxylic acid (135)

$^1$H NMR (CDCl$_3$): 1.32(t, J=6.8 Hz, 3H, 3-CH$_2$CH$_3$); 2.38(s, 3H, 2-CH$_3$); 4.29(m, 2H, 3-OCH$_2$); 5.08(s, 1H, 4-H); 5.95(br, 1H, NH); 7.24–7.44(m, 10H, 2×C$_6$H$_5$). MS(CI/NH$_3$): m/z 405 (M+NH$_4$); 388(MH)$^+$.

3-Ethoxycarbonyl-2-methyl-4-phenylethynyl-6-phenyl-1,4(±)-dihydropyridine-5-carboxylic ethyl amide (132)

A mixture of compound 139 (75 mg, 0.17 mmol), N-hydroxysuccinimide (22 mg, 0.17 mmol) and DAEC (34 mg, 0.17 mmol) in DMF (1 mL) was stirred at room temperature for 4 h. Ethylamine (2.0 M in THF, 0.4 mL) was added, and the reaction was stirred overnight. The solvent was removed and the residue was diluted with dichloromethane (10 mL), washed with water (5 mL×2) and brine (5 mL×2), dried with sodium sulfate. The solvent was evaporated and the residue was purified with preparative TLC plate to give 38 mg of compound 140 which was carried out for deprotection with 1N HCl to give 18 mg of product 132.

140: $^1$H NMR (CDCl3): 0.72(t, J=6.8 Hz, 3H, 1-CH$_2$CH$_3$); 0.96(t, J=6.8 Hz, 3H, 5-CH$_2$CH$_3$); 1.33 (t, J=6.8 Hz, 3H, 3-CH$_2$CH$_3$); 2.60(s, 3H, 2-CH$_3$); 3.08(m, 2H, 5-NCH$_2$); 3.62(m, 2H, 1-OCH$_2$); 4.23(m, 2H, 3-OCH$_2$); 4.45, 4.85 (AV, J=11.7 Hz, N—CH$_2$—O); 4.92(s, 1H, 4-H); 4.97(br, 1H, CONH); 7.22–7.44(m, 10H, 2×C$_6$H$_5$). MS(CI/NH$_3$): m/z 473 (MH)$^+$.

132: $^1$HNMR (CDCl$_3$): 0.85(t, J=6.8 Hz, 3H 5-CH$_2$CH$_3$); 1.31 (t, J=6.8 Hz, 3H, 3-CH$_2$CH$_3$); 2.37(s, 3H, 2-CH$_3$); 3.16(m, 2H, 5-NCH$_2$); 4.25(m, 2H, 3-OCH$_2$); 5.09 (s, 1H, 4-H); 5.37(br, 1H, CONH); 5.64 (br, 1H, NH); 7.25–7.44(m, 10H, 2×C$_6$H$_5$). MS(CI/NH$_3$): m/z

3-t-Butyl 5-ethyl 2-methyl-4-phenylethynyl-6-phenyl-1,4-(±)-dihydropyridine-3,5-dicarboxylate (133)

$^1$HNMR (CDCl$_3$): δ0.91(t, J=6.9 Hz, 3H, 5-CH$_2$CH$_3$); 1.52 (s, 9H, C(CH$_3$)$_3$); 2.29(s, 3H, 2-CH$_3$); 3.98(m, 2H, 5-OCH$_2$); 5.05(s, 1H, 4-H); 5.71(br, 1H, NH); 7.21–7.40(m, 10H, 2×C$_6$H$_5$). MS(CI/NH$_3$): m/z 461 (M+HN$_4$)$^+$; 443 (MH)$^+$.

5-Ethoxycarbonyl-2-methyl-4-phenylethynyl-6-phenyl-1,4-(±)-dihydropyridine-3-carboxylic ethyl amide (134)

$^1$H NMR (CDCl$_3$): 0.85 (t, J=6.8 Hz, 3H, 3-CH$_2$CH$_3$); 1.18 (t, J=6.8 Hz, 3H, 5-CH$_2$CH$_3$); 2.24 (s, 3H, 2-CH$_3$); 3.38(m, 2H, 3-NCH$_2$); 3.94(m, 2H, 5-OCH$_2$); 4.80 (s, 1H, 4-H); 5.65(br, 1H, NH); 6.32(br, 1H, CONH); 7.23–7.38(m, 10H, 2×C$_6$H$_5$). MS(EI): m/z 414(M)$^+$; 385(M-C$_2$H$_5$)$^+$, base; 342(M-CONHC$_2$H$_5$)$^+$.

3-Ethylcarbonyl 5-ethoxycarbonyl 2-methyl-4-phenylethynyl-6-phenyl-1,4-±-dihydropyridine (135)

$^1$H NMR (CDCl$_3$); δ 0.93 (t, J=7.0 Hz, 3H, 5-CH$_2$CH$_3$); 2.33(s, 3H, 2-CH$_3$); 2.48(s, 3H, 3-COCH$_3$); 4.00(q, 2H, J=7.0 Hz, 5-OCH$_2$); 5.04(s, 1H, 4-H); 5.88(br, 1H, NH); 7.26–7.43(m, 10H, 2×C$_6$H$_5$). MS(EI: m/z 385(M)$^+$; 443 (M-CH$_3$CO)$^+$, base.

Ethyl 3-oxo-1,4,5,6,7,8-hexahydroquinoline-2-methyl-4-phenylethynyl-6-phenyl-1,4-±-dihydropyridin-5-carboxylate (136)

$^1$H NMR (CDCl$_3$); δ 1.02 (t, J=6.8 Hz, 3H, 5-CH$_2$CH$_3$); 2.04(t, J=4.9 Hz, 2H, 7-CH$_2$); 2.46(m, 4H, 8&9-CH$_2$); 4.00(m, 2H, 5-OCH$_2$); 5.13(s, 1H, 4-H); 6.14(br, 1H, NH);

7.20–7.41 (m, 10H, 2×C$_6$H$_5$). Ms(EI: m/z 397 (M)$^+$; 368 (M-C$_2$H$_5$)$^+$, base.

General Procedure of N—H Group Protection in Compound (129)

Sodium hydride (60%) in mineral oil, 1.5 eq.) was added to compound 129 in solution of DMF (1.5 mL). The mixture was stirred for 5 min, chloromethyl methyl (ethyl) ether (1.5 eq.) was added slowly to the solution under argon at room temperature and stirred for 2 h. The reaction was quenched by adding cold water (10 mL), extracted with ethyl acetate (10 mL×2), the organic layer was washed with water (10 mL×2), brine (10 mL×2), dried with sodium sulfate. The solvent was evaporated and residue was purified with preparative TLC plates to give corresponding N-protected products 137 and 138.

1-Methoxymethyl 3-ethyl 5-(2-trimethylsilyl)-ethyl 2-methyl-4-phenylethynyl-6-phenyl-1,4-(±)-dihydropyridine-3,5-dicarboxylate (137)

$^1$H NMR (CDCl3): δ–0.04(s,9H, Si(CH$_3$)$_3$); 0.63(m, 2H, CH$_2$Si); 1.33 (t, J=7.0 Hz, 3H, 3-CH$_2$CH$_3$); 2.54(s, 3H, 2-CH$_3$); 3.18 (s, 3H, OCH$_3$); 3.97(t, J=7.8 Hz, 2H, 5-OCH$_2$); 4.27 (m, 2H, 3-OCH$_2$); 4.37, 4.85 (AB, J=11.7 Hz, N—CH$_2$—O); 5.07 (s, 1H, 4-H); 7.21–7.40 (M, 10H, 2×C$_6$H$_5$). MS (CI/NH$_3$): m/z 549 (M+NH$_4$)$^+$; 532 (MH)$^+$.

1-Ethoxymethyl 3-ethyl 5-(2-trimethylsilyl)-ethyl 2-methyl-4-phenylethynyl-6-phenyl-1,4-(±)-dihydropyridine-3,5-dicarboxylate (138)

$^1$H NMR (CDCl$_3$); δ–0.08(s, 9H, Si(CH$_3$)3); 0.61(m, 2H, CH$_2$Si); 0.91 (t, J=6.9 Hz, 3H, OCH$_2$CH$_3$); 1.41(t, J=6.9 Hz, 3H, 3-CH$_2$CH$_3$); 2.57(s, 3H, 2-CH$_3$); 3.13(m, 2H, OCH$_2$CH$_3$); 3.95(t, J=7.9 Hz, 2H, 5-OCH$_2$); 4.12(m, 2H, 3-OCH$_2$); 4.41, 4.81 (AB, J=10.8 Hz, 2H, N—CH$_2$—O); 5.02(s, 1H, 4-H); 7.20–7.39 (m, 10H, 2×C$_6$H$_5$). MS(CI/NH$_3$): m/z 563 (M+NH$_4$)$^+$; 546(MH)$^+$.

1-Ethoxymethyl-3-ethoxycarbonyl-2-methyl-4-phenylethynyl-6-phenyl-1,4-(±)-dihydropyridine-5-carboxylic acid (139)

TBAF (hydrate, 208 mg, 0.8 mmol) was added to a solution of 138 (115 mg, 0.21 mmol) in DMF (1 mL). The mixture was stirred under argon at room temperature for 2 h, diluted with ethyl acetate (20 mL), washed with 1N HCl (5 mL), H$_2$O (20 m mL×2) and brine (20 mL×2), dried with magnesium sulfate. The solvent was evaporated and residue was separated with preparative TLC plates to give 80 mg of product.

$^1$H NMR (CDCl$_3$); δ0.93 (t, J=6.8 Hz, 3H OCH$_2$CH$_3$); 1.31 (t, J=6.9 Hz, 3H, 3-CH$_2$CH$_3$); 2.59 (s, 3H, 2-CH$_3$); 3.09, 3.65 (2m, 2H, OCH$_2$CH$_3$); 4.27 (m, J=7.9 Hz, 2H, 3-OCH$_2$); 4.39, 4.85 (2d, J=10.7 Hz, 2H, 3-OCH$_2$); 4.41, 4.81 (AB, J=10.8 Hz, 2H, N—CH$_2$—O); 5.02(s, 1H, 4-H); 7.12 (br, 1H, COOH); 7.20–7.39 (m, 10H, 2×C$_6$H$_5$). MS (CI/NH$_3$): m/z 463 (M+NH$_4$)$^+$; 446(MH)$^+$.

3,5-diethyl 2-methyl-4-(2-[4-nitro-phenyl]ethynyl)-1,4(±)-dihydropyridine-3,5-dicarboxylate (119)

$^1$H NMR (d-CHCl$_3$) δ: 1.25–1.34 (m, 6H, 3-&5-CH$_3$); 2.49 (s, 3H, 2-CH$_3$); 3.47–3.59 (m, 2H, 3-CH$_2$); 4.23 (q, 2H, 5-CH$_2$, J=7.8 Hz); 5.42 (s, 1H, H-4); 56.29 (d, 1H, H-1, J=2.9 Hz); 7.55 (d, 2H, H-2' & H-6", J=8.8 Hz); 8.21 (d, 2H, H-3' & H-5', J=8.8 Hz); 8.26 (wide, 1H, H-6).

3,5-diethyl 2-methyl-4-(2-[3-toluyl]ethynyl)-1,4(±)-dihydropyridine-3,5-dicarboxylate (120)

$^1$H NMR (d-CHCl$_3$) δ: 1.25–1.34 (m, 6H, 3-&5-CH$_3$); 2.49 (s, 3H, 2-CH$_3$); 3.47–3.59 (m, 2H, 3-CH$_2$); 4.23 (q, 2H, 5-CH$_2$, J=7.8 Hz); 5.42 (s, 1H, H-4); 56.29 (d, 1H, H-1, J=2.9 Hz); 7.55 (d, 2H, H-2' & H-6", J=8.8 Hz); 8.21 (d, 2H, H-3' & H-5', J=8.8 Hz); 8.26 (wide, 1H, H-6).

TABLE 8

Characterization data of dihydropyridine and derivatives.

| Compound | T$_m$(° C.) | formula | MS | elemental analysis | yield (%) | purification$^d$ |
|---|---|---|---|---|---|---|
| 52 | 125–126 | C$_{13}$H$_{19}$NO$_4$ | 253 (CI) | C,H,N | 98.2 | 1;MeOH |
| 53 | 88–89 | C$_{14}$H$_{21}$NO$_5$—0.25H$_2$O | 283 (CI) | C,H,N | 53.0 | 2;TLC |
| 54 | oil | C$_{18}$H$_{21}$NO$_4$—0.50H$_2$O | 315 (CI) | C,H,N | 70.5 | 2;TLC |
| 56 | 83–84 | C$_{14}$H$_{21}$NO$_4$ | 267 (CI) | C,H,N | 50.5 | 1;MeOH |
| 57 | 95–96 | C$_{15}$H$_{23}$NO$_4$ | 281 (CI) | H,N$^a$ | 73.3 | 1;MeOH |
| 58 | glass | C$_{21}$H$_{33}$NO$_4$ | 363 $^b$ (CI) |  | 33.4 | 2;TLC |
| 59 | 121–122 | C$_{18}$H$_{21}$NO$_4$ | 315 (CI) | C,H,N | 78.6 | 1;MeOH |
| 61 | 78–79 | C$_{18}$H$_{20}$N$_2$O$_6$ | 360 (CI) | C,H,N | 88.3 | 2;TLC |
| 62 | 165–166 | C$_{19}$H$_{22}$N$_2$O$_6$ | 374 (EI) | C,H,N | 35.5 | 1;EtOAc |
| 67 | 151–152 | C$_{18}$H$_{20}$N$_2$O$_6$ | 360 (CI) | C,H,N | 68.1 | 1;MeOH |
| 68 | 114–115 | C$_{19}$H$_{20}$F$_3$NO$_4$ | 383 (CI) | C,H$^c$ | 45.6 | 2;TLC |
| 71 | 112–113 | C$_{19}$H$_{23}$NO$_5$—0.21 EtOAc | 345 (CI) | C,H,N | 61.8 | 2;TLC |

TABLE 8-continued

Characterization data of dihydropyridine and derivatives.

| Compound | $T_m$(° C.) | formula | MS | elemental analysis | yield (%) | purification[d] |
|---|---|---|---|---|---|---|
| 72 | 190 | $C_{19}H_{23}NO_6$ | 361 (CI) | C,H,N | 79.6 | 1;MeOH |
| 73 | oil | $C_{19}H_{21}NO_6$—0.32 EtOAc | 359 (CI) | C,H,N | 63.0 | 2;TLC |
| 74 | 87–88 | $C_{20}H_{25}NO_4$ | 343 (CI) | C,H,N | 71.9 | 2;TLC |
| 75 | 135–136 | $C_{20}H_{23}NO_4$ | 341 (CI) | C,H,N | 87.9 | 1;MeOH |
| 76 | 176–177 | $C_{20}H_{21}NO_4$ | 339 (EI) | C,H,N | 43.3 | 2;EtOH |
| 77 | oil | $C_{17}H_{27}NO_4$ | 309 (CI) | C,H,N | 58.8 | 2;TLC |
| 78 | 123–124 | $C_{19}H_{23}NO_4$ | 329 (CI) | C,H,N | 53.0 | 1;pe 35–60 |
| 79 | oil | $C_{26}H_{27}NO_4$ | 417 (CI) | C,H,N | 34.7 | 2;column |
| 80 | oil | $C_{13}H_{17}NO_4$ | 251 (EI) | C,H,N | 57.9 | 2;TLC |
| 81 | oil | $C_{19}H_{21}NO_4$—0.20 EtOH | 327 (EI) | C,H,N | 48.9 | 2:TLC |

[a]57($C_{15}H_{23}NO_4$) H,N;C: calcd, 64.03; found, 64.75;EI: calcd, 281.1627; found 281.1630
[b]58($C_{21}H_{33}NO_4$) C,H,N: calcd, 69.39,9.15,3.85; found, 61.65,7.27,4.70; EI: calcd, 363.2410; found
[c]68($C_{19}H_{20}F_3NO_4$) C,H;N: calcd, 3.65; found,4.17;EI: calcd,383.1344;found,383.1346
[d]Purification was achieved either by:
1. recrystallization from the solvent specified, or
2. chromatography by the specified method, using EtOAc:pe 35–60 20:80((v/v) eluent.
MeOH methanol
EtOH ethanol
EtOAc ethyl acetate
pe 35–60 petroleum ether 35–60 ° C. fraction
TLC preparative thin layer chromatography, silica 60, 1000 mm layer thickness
column preparative column chromatography, silica 60, 220–440 mesh.

EXAMPLE 25

This Example illustrates the affinities of certain dihydropyridine derivatives. The affinities were determined in radioligand binding assays, and the results thereof are set forth in Table 9.

TABLE 9

Affinities of dihydropyridine derivatives in radioligand binding assays at $A_1$, $A_{2A}$, and $A_3$ receptors.

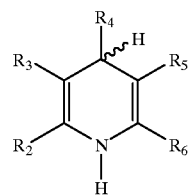

| Compound | $R_2$ | $R_3$ | $R_4$ | $R_5$ | $R_6$ | $rA^a_1$ | $rA^b_{2A}$ | $hA^c_3$ |
|---|---|---|---|---|---|---|---|---|
| 52 | $CH_3$ | $CO_2CH_3$ | $CH_3$ | $CO_2CH_2CH_3$ | $CH_3$ | 32.6 ± 6.3 | >100 | 32.3 ± 5.1 |
| 53 | $CH_3$ | $CO_2CH_3$ | $CH_3$ | $CO_2(CH_2)_2$—$OCH_3$ | $CH_3$ | 49.2 ± 0.7 | 19% ($10^{-4}$) | 62.3 ± 16.7 |
| 54 | $CH_3$ | $CO_2CH_3$ | $CH_3$ | $CO_2CH_2Ph$ | $CH_3$ | 6.45 ± 1.47 | 9.72 ± 0.63 | 2.78 ± 0.89 |
| 55 | $CH_3$ | $CO_2CH_2CH_3$ | $CH_3$ | $CO_2(CH_2)_3$—SPh | $CH_3$ | 6.50 ± 0.47 | 7.10 ± 2.46 | 5.56 ± 1.36 |
| 56 | $CH_3$ | $CO_2CH_3$ | $CH_2CH_3$ | $CO_2CH_2CH_3$ | $CH_3$ | 7.52 ± 2.79 | 9.56 ± 2.69 | 13.6 ± 2.0 |
| 57 | $CH_3$ | $CO_2CH_3$ | $(CH_2)_2CH_3$ | $CO_2CH_2CH_2$ | $CH_3$ | 8.17 ± 1.58 | 11.5 ± 3.8 | 6.51 ± 0.74 |
| 58 | $CH_3$ | $CO_2CH_3$ | $CH_2CHCH_3(CH_2)_2$—CH=$C(CH_3)_2$ (R, S) | $CO_2CH_2CH_3$ | $CH_3$ | 9.10 ± 2.90 | 23.1 ± 8.6 | 7.90 ± 0.88 |

TABLE 9-continued

Affinities of dihydropyridine derivatives in radioligand binding assays at $A_1$, $A_{2A}$, and $A_3$ receptors.

| Compound | $R_2$ | $R_3$ | $R_4$ | $R_5$ | $R_6$ | $rA^a_1$ | $rA^b_{2A}$ | $hA^c_3$ |
|---|---|---|---|---|---|---|---|---|
| 59 | $CH_3$ | $CO_2CH_3$ | Ph | $CO_2CH_2CH_3$ | $CH_3$ | 11.0 ± 1.6 | 2.74 ± 0.85 | 12.0 ± 3.3 |
| 60 nifedipine | $CH_3$ | $CO_2CH_3$ | 2-$NO_2$-Ph | $CO_2CH_3$ | $CH_3$ | 2.89 ± 0.23 | 18.2 ± 2.51 | 8.29 ± 2.41 |
| 61 | $CH_3$ | $CO_2CH_3$ | 3-$NO_2$-Ph | $CO_2CH_2CH_3$ | $CH_3$ | 8.96 ± 2.06 | 23.0 ± 3.7 | 8.30 ± 1.41 |
| 62 | $CH_3$ | $CO_2CH_2CH_3$ | 3-$NO_2$-Ph | $CO_2CH_2CH_3$ | $CH_3$ | 3.34 ± 2.17 | 18.2 ± 79 | 2.51 ± 0.15 |
| 63 | $CH_3$ | $CO_2CH_3$ | 3-$NO_2$-Ph | $CO_2CH_2CH_2N$-(Bz)$CH_3$ | $CH_3$ | 19.6 ± 1.9 | 63.8 ± 4.2 | 3.25 ± 0.26 |
| 64 | $CH_3$ | $CO_2CH(CH_3)_2$ | 3-$NO_2$-Ph | $CO_2CH_2CH_2O$—$CH_3$ | $CH_3$ | 20.1 ± 1.7 | 44.3 ± 14.4 | 8.47 ± 2.75 |
| 65 | $CH_3$ | $CO_2CH_3$ | 3-$NO_2$-Ph | $CO_2(CH_2)_3$—N(piperidine-4,4-diPh) | $CH_3$ | 41.3 ± 3.5 | ~300 | 1.90 ± 0.40 |
| 66 | $CH_3$ | $CO_2CH_3$ | 3-$NO_2$-Ph | $CO_2(CH_2)_3$—N(piperidine-4,4-diPh) | $CH_3$ | d ($10^{-4}$) | d ($10^{-4}$) | 2.80 ± 0.35 |
| 67 | $CH_3$ | $CO_2CH_3$ | 4-$NO_2$-Ph | $CO_2CH_2CH_3$ | $CH_3$ | 37 ± 14% ($10^{-4}$) | 35.6 ± 1.9 | 5.90 ± 1.65 |
| 68 | $CH_3$ | $CO_2CH_3$ | 2-$CF_3$-Ph | $CO_2CH_2CH_3$ | $CH_3$ | 6.68 ± 2.37 | 20.7 ± 2.8 | 11.6 ± 1.7 |
| 69 | $CH_3$ | $CO_2CH_3$ | 2-$CF_3$-Ph | $NO_2$ | $CH_3$ | 0.785 ± 0.113 | 35.1 ± 10.1 | 2.77 ± 0.34 |
| 70 | $CH_3$ | $CO_2CH_3$ | 2-$CF_3$-Ph | $NO_2$ | $CH_3$ | 6.66 ± 1.89 | 86.3 ± 28.4 | 23.5 ± 0.6 |
| 71 | $CH_3$ | $CO_2CH_3$ | 4-$CH_3O$-Ph | $CO_2CH_2CH_3$ | $CH_3$ | 2.75 ± 0.35 | 12.7 ± 3.8 | 4.10 ± 0.14 |
| 72 | $CH_3$ | $CO_2CH_3$ | 3-$CH_3O$-4-OH-Ph | $CO_2CH_2CH_3$ | $CH_3$ | 51.0 ± 3.7 | 56.8 ± 1.9 | 32.1 ± 9.2 |
| 73 | $CH_3$ | $CO_2CH_3$ | 3,4-$OCH_2O$-Ph | $CO_2CH_2CH_3$ | $CH_3$ | 3.66 ± 0.61 | 5.27 ± 1.97 | 4.58 ± 1.11 |
| 74 | $CH_3$ | $CO_2CH_3$ | Ph-$CH_2$—$CH_2$ | $CO_2CH_2CH_3$ | $CH_3$ | 8.81 ± 0.92 | 6.71 ± 2.06 | 2.30 ± 0.70 |
| 75 | $CH_3$ | $CO_2CH_3$ | Ph-CH=CH— (trans) | $CO_2CH_2CH_3$ | $CH_3$ | 16.1 ± 0.5 | 49.3 ± 12.5 | 0.670 ± 0.195 |
| 76 | $CH_3$ | $CO_2CH_3$ | Ph-C≡C— | $CO_2CH_2CH_3$ | $CH_3$ | 5.39 ± 0.33 | 38.3 ± 7.9 | 0.940 ± 0.70 |
| 77 | $CH_3$ | $CO_2CH_2CH_3$ | $CH_3$ | $CO_2CH_2CH_3$ | $(CH_2)_3CH_3$ | 10.8 ± 3.52 | 38.0 ± 10.6 | 47.1 ± 10.8 |
| 78 | $CH_3$ | $CO_2CH_2CH_3$ | $CH_3$ | $CO_2CH_2CH_3$ | Ph | 25.9 ± 7.3 | 35.9 ± 15.3 | 7.24 ± 2.13 |
| 79 | $CH_3$ | $CO_2CH_2CH_3$ | Ph-CH=CH— (trans) | $CO_2CH_2CH_3$ | Ph | 5.93 ± 0.27 | 4.77 ± 0.29 | 0.108 ± 0.012 |

[a]Displacement of specific [$^3$H] PIA binding in rat brain membranes, expressed as $K_i$ ± S.E.M. in μM (n = 3–5).
[b]Displacement of specific [$^3$H] CGS 21680 binding in rat striatal membranes, expressed as $K_i$ ± S.E.M. in μM (n = 3–6).
[c]Displacement of specific [$^{125}$I] AB-MECA binding at human $A_3$ receptors expressed in HEK cells, in membranes, expressed as $K_i$ ± S.E.M. in μM (n = 2–3), or as a percentage of specific binding displaced at 10 μM.
[d]Displacement of ≦10% of specific binding at the indicated concentration in M.

EXAMPLE 26

This Example illustrates the affinities of certain pyridine derivatives. The affinities were determined in radioligand binding assays, and the results thereof are set forth in Table 10.

TABLE 10

Affinities of pyridine derivatives in radioligand binding assays at $A_1$, $A_{2a}$, and $A_3$ receptors.

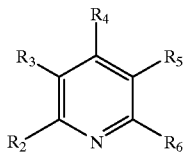

| Compound | $R_2$ | $R_3$ | $R_4$ | $R_5$ | $R_6$ | $rA^a_1$ | $rA^b_{2a}$ | $hA^c_3$ |
|---|---|---|---|---|---|---|---|---|
| 80 | $CH_3$ | $CO_2CH_3$ | $CH_3$ | $CO_2CH_2CH_3$ | $CH_3$ | 6.95 ± 2.66 | 8.96 ± 0.93 | 29.5 ± 2.1 |
| 81 | $CH_3$ | $CO_2CH_2CH_3$ | $CH_3$ | $CO_2CH_2CH_3$ | Ph | 7.41 ± 1.29 | 28.4 ± 9.1 | 4.47 ± 0.46 |
| 82 | $CH_3$ | $CO_2CH_3$ | o-$NO_2$-Ph | $CO_2CH_3$ | $CH_3$ | d ($10^{-4}$) | d ($10^{-4}$) | d ($10^{-4}$) |
| 83 | H | H | 4-$CH_3$O-Ph | H | H | 44.5 ± 1.0 | 71 ± 29 | d ($10^{-4}$) |

[a]Displacement of specific [$^3$H] PIA binding in rat brain membranes, expressed as $K_i$ ± S.E.M. in $\mu$M (n = 3–5).
[b]Displacement of specific [$^3$H] CGS 21680 binding in rat striatal membranes, expressed as $K_i$ ± S.E.M. in $\mu$M (n = 3–6).
[c]Displacement of specific [$^{125}$I] AB-MECA binding at human $A_3$ receptors expressed in HEK cells, in membranes, expressed as $K_i$ ± S.E.M. in $\mu$M (n = 2–3), or as a percentage of specific binding displaced at 10 $\mu$M.
[d]Displacement of ≦10% of specific binding at the indicated concentration in M.

EXAMPLE 27

This Example illustrates the affinities of certain dihydropyridine and pyridine derivatives. The affinities were determined in radioligand binding assays, and the results thereof are set forth in Tables 11–12.

TABLE 11

Affinities of certain dihydropyridine and pyridine derivatives in radioligand binding assays at $A_1$, $A_{2a}$, and $A_3$ receptors.[a–e]

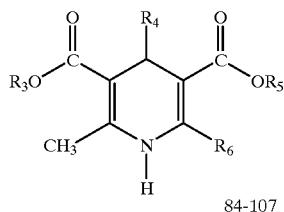 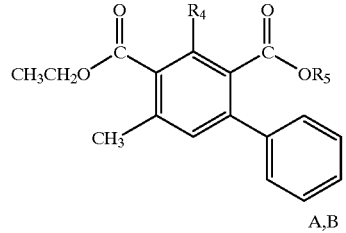

84-107                                                                 A,B

| | | | | | $K_i$ ($\mu$M) or % inhibition[c] | | | |
|---|---|---|---|---|---|---|---|---|
| Compound | $R_3$ | $R_4$ | $R_5$ | $R_6$ | $rA_1$ | $rA_{2A}$ | $hA_3$ | $rA_1/hA_3$ |
| 84 | $CH_2CH_3$ | Ph-CH=CH— (trans) | $CH_2CH_3$ | $CH_3$ | 4.65 ± 1.21 | 9.23 ± 3.60 | 0.887 ± 0.138 | 5.2 |
| 85 | $CH_2CH_3$ | Ph-CH=CH— (trans) | $CH_2$Ph | $CH_3$ | 13.7 ± 2.6 | 14.4 ± 4% ($10^{-4}$) | 3.13 ± 0.51 | 4.4 |
| 86 | $CH_2CH_3$ | $CH_2CH_3$ | $CH_2CH_3$ | Ph | 21.5 ± 2.7 | 14.5 ± 3.5 | 8.49 ± 1.74 | 2.5 |
| 87 | $CH_2CH_3$ | $CH_3$ | $CH_2$Ph | Ph | 26.0 ± 8.7 | 3.15 ± 0.96 | 1.75 ± 0.47 | 15 |
| 88 | $CH_2CH_3$ | Ph-CH=CH— (trans) | $CH_2CH_3$ | 4-$CH_3$-Ph | 14.9 ± 4.9 | 37 ± 2% ($10^{-4}$) | 9.13 ± 2.43 | 1.6 |
| 89 | $CH_2CH_3$ | Ph-CH=CH— (trans) | $CH_2CH_3$ | 4-$OCH_3$-Ph | 9.49 ± 1.99 | d ($10^{-4}$) | 1.43 ± 0.37 | 6.6 |
| 90 | $CH_2CH_3$ | Ph-CH=CH— (trans) | $CH_2CH_3$ | 4-Cl-Ph | 33.0 ± 7.5 | 12 ± 7% ($10^{-4}$) | 0.785 ± 0.272 | 42 |
| 91 | $CH_2CH_3$ | Ph-CH=CH— (trans) | $CH_2CH_3$ | 4-$NO_2$-Ph | 13.1 ± 1.6 | | 4.14 ± 0.51 | 3.2 |
| 92 | $CH_2CH_3$ | Ph-CH=CH— | $CH_2CH_3$ | 3-furyl | 5.49 ± 0.25 | 35 ± 6% | 0.907 ± 0.307 | 6.1 |

TABLE 11-continued

Affinities of certain dihydropyridine and pyridine derivatives in radioligand binding assays at $A_1$, $A_{2a}$, and $A_3$ receptors.[a–e]

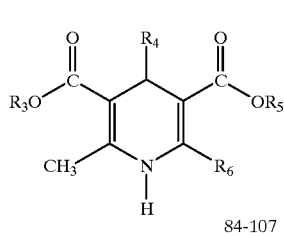

84-107

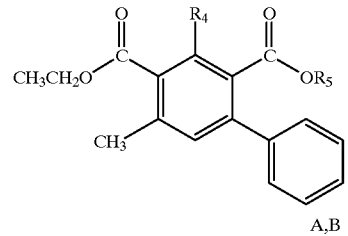

A,B

| Compound | $R_3$ | $R_4$ | $R_5$ | $R_6$ | $K_i$ (μM) or % inhibition[c] | | | |
|---|---|---|---|---|---|---|---|---|
| | | | | | $rA_1$ | $rA_{2A}$ | $hA_3$ | $rA_1/hA_3$ |
| 93 | $CH_2CH_3$ | Ph-CH=CH— (trans) | $CH_2CH_3$ | 3-thienyl | 7.52 ± 1.38 | d ($10^{-4}$) | 0.407 ± 0.066 | 18 |
| 94 | $CH_2CH_3$ | 2-OCH$_3$-Ph-(CH=CH— (trans) | $CH_2CH_3$ | Ph | 25.3 ± 2.4 | 17 ± 12% ($10^{-4}$) | 0.334 ± 0.059 | 76 |
| 95 | $CH_2CH_3$ | 2-NO$_2$-Ph-CH=CH— (trans) | $CH_2CH_3$ | Ph | 6.03 ± 1.39 | d ($10^{-4}$) | 0.109 ± 0.017 | 55 |
| 96 | $CH_2CH_3$ | 4-NO$_2$-Ph-CH=CH— (trans) | $CH_2CH_3$ | Ph | | | 0.07 | |
| 97 | $CH_2CH_3$ | (Ph)$_2$C=CH— | $CH_2CH_3$ | Ph | 1.20 ± 0.14 | 8 | 1.42 ± 0.23 | 0.84 |
| 98 | $CH_2CH_3$ | Ph-C≡C— | $CH_2CH_3$ | Ph | 11.0 ± 0.1 | | 0.0766 ± 0.0151 | 140 |
| 99 | $CH_2CH_3$ | Ph-CH=CH— (trans) | $CH_2Ph$ | Ph | 35 ± 3% ($10^{-4}$) | 15 ± 3% ($10^{-4}$) | 0.0583 ± 0.0124 | >1700 |
| 100 | $CH_2CH_3$ | 4-NO$_2$-Ph-CH=CH— (trans) | $CH_2Ph$ | Ph | 33 ± 1% ($10^{-4}$) | d ($10^{-4}$) | 0.0724 ± 0.0377 | >1300 |
| 101 | $CH_2CH_3$ | Ph-C≡C— | $CH_2Ph$ | Ph | 40.1 ± 7.5 | d ($10^{-4}$) | 0.0314 ± 0.0028 | 1300 |
| 102 | $CH_2CH_3$ | 4-NO$_2$-Ph-C≡C | $CH_2Ph$ | Ph | | | <0.1 | |
| 103 | $CH_2CH_3$ | 4-NH$_2$-Ph-C≡C— | $CH_2Ph$ | Ph | | | <0.1 | |
| 104 | $CH_2CH_3$ | 4-NH$_2$-3-I-Ph-C≡C— | $CH_2Ph$ | Ph | | | <0.1 | |
| 105 | $CH_2Ph$ | Ph-CH=CH— (trans) | $CH_2CH_3$ | Ph | d ($10^{-4}$) | 16 ± 11% ($10^{-4}$) | 0.142 ± 0.047 | >700 |
| 106 | $CH_2Ph$ | 4-NO$_2$-Ph-CH=CH— (trans) | $CH_2CH_3$ | Ph | d ($10^{-4}$) | d ($10^{-4}$) | 0.286 ± 0.038 | >400 |
| 107 | $CH_2Ph$ | Ph-C≡C— | $CH_2CH_3$ | Ph | 24 ± 4% ($10^{-4}$) | d ($10^{-4}$) | 0.169 ± 0.026 | >600 |
| A | | Ph-CH=CH— (trans) | $CH_2CH_3$ | | 2.52 | 2.6 | 6.3 | 0.4 |
| B | | Ph-C≡C— | $CH_2Ph$ | | 7.01 ± 1.98 | 43 ± 2% ($10^{-4}$) | 2.75 ± 0.78 | 2.6 |

[a]Displacement of specific [$^3$H] PIA binding in rat brain membranes, expressed as $K_i$ ± S.E.M. in μM (n = 3–5), or as a percentage of specific binding displaced at the indicated concentration (M).
[b]Displacement of specific [$^3$H] CGS 21680 binding in rat striatal membranes, expressed as $K_i$ ± S.E.M. in μM (n = 3–5), or as a percentage of specific binding displaced at the indicated concentration (M).
[c]Displacement of specific [$^{125}$I] AB-MECA binding at human $A_3$ receptors expressed in HEK cells, in membranes, expressed as $K_i$ ± S.E.M. in μM (n = 3–4), or as a percentage of specific binding displaced at the indicated concentration (M).
[d]Displacement of ≤10% of specific binding at the indicated concentration (M).
[e]values from van Rhee et al.

TABLE 12

Affinities of dihydropyridine derivatives in radioligand binding assays at $A_1$, $A_{2a}$, and $A_3$ receptors.[a–e]

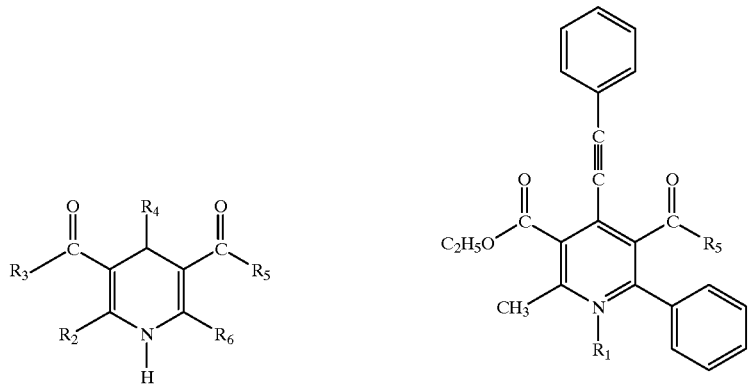

108-136
$R_2$ = Methyl  $R_6$ = Phenyl 137-140

| Compound | $R_3$ | $R_4$ | $R_5$ | $rA^a_1$ | $rA_{2A}^b$ | $hA_3^c$ | $rA_1/hA_3$ |
|---|---|---|---|---|---|---|---|
| | | | | \multicolumn{3}{c}{$K_i$ ($\mu$M) or % inhibition[c]} | |
| 108 | $OCH_2CH_3$ | 2-thienyl- | $OCH_2CH_3$ | 4.48 ± 0.90 | 25 ± 5% ($10^{-4}$) | 8.56 ± 1.22 | 0.52 |
| 109 | $OCH_2CH_3$ | Ph-C≡C— | $OCH_2CH_3$ | 23.6 ± 2.9 | 25 ± 3% ($10^{-4}$) | 1.58 ± 0.56 | 15.0 |
| 110 | $OCH_2CH_3$ | Ph | $OCH_2CH_3$ | 8.03 ± 2.05 | d ($10^{-4}$) | 1.71 ± 0.36 | 4.7 |
| 111 | $OCH_2CH_3$ | 2-pyridyl- | $OCH_2CH_3$ | 17.4 ± 16.0 | 25 ± 3% ($10^{-4}$) | 12.2 ± 0.3 | 1.4 |
| 112 | $OCH_2CH_3$ | 3-pyridyl- | $OCH_2CH_3$ | 26.6 ± 1.2 | 40 ± 2% ($10^{-4}$) | 19.2 ± 2.6 | 1.8 |
| 113 | $OCH_2CH_3$ | 4-pyridyl- | $OCH_2CH_3$ | 14.9 ± 0.2 | 44.7 ± 3.7 | 8.31 ± 1.84 | 1.8 |
| 114 | $OCH_2CH_3$ | 2-thienyl- | $OCH_2CH_3$ | 8.59 ± 1.90 | 36 ± 4% ($10^{-4}$) | 1.04 ± 0.26 | 8.3 |
| 115 | $OCH_2CH_3$ | 2-furyl- | $OCH_2CH_3$ | 3.65 ± 0.45 | d ($10^{-4}$) | 0.314 ± 0.056 | 12 |
| 116 | $OCH_2CH_3$ | 2-benzofuryl- | $OCH_2CH_3$ | 3.65 ± 0.45 | d ($10^{-4}$) | 0.314 ± 0.056 | 12 |
| 117 | $OCH_2CH=CH_2$ | 4-$NO_2$-Ph-CH=CH (trans) | $OCH_2CH_3$ | d ($10^{-4}$) | 15 ± 2% ($10^{-4}$) | 0.296 ± 0.063 | >300 |
| 118 | $OCH_2CH_3$ | 4-$NO_2$-Ph-CH=CH (trans) | $OCH_2CH_3$ | 31 ± 3% ($10^{-4}$) | 26 ± 6% ($10^{-4}$) | 0.198 ± 0.047 | >500 |
| 119 | $OCH_2CH_3$ | 4-$NO_2$-Ph-C≡C— | $OCH_2CH_3$ | 34.5 ± 6.8 | 24 ± 4% ($10^{-4}$) | 2.58 ± 0.66 | 13 |
| 120 | $OCH_2CH_3$ | 3-$CH_3$-Ph-C≡C— | $OCH_2CH_3$ | 41 ± 5% ($10^{-4}$) | d ($10^{-4}$) | 0.220 ± .108 | >400 |
| 121 | $OCH_2CH_3$ | Ph-C≡C— | $OCH_2Ph$ | 25 ± 4% ($10^{-4}$) | d ($10^{-4}$) | 0.695 ± 0.0131 | 1400 |
| 122a | $OCH_2CH_3$ | Ph-C≡C— | $OCH(2-CH_3)Ph$ | 16 ± 1% ($10^{-4}$) | 13 ± 1% ($10^{-4}$) | 0.112 ± 0.015 | 1000 |
| 122b | $OCH_2CH_3$ | Ph-C≡C— | $OCH(3-CH_3)Ph$ | d ($10^{-4}$) | 16 ± 2% ($10^{-4}$) | 0.0524 ± 0.017 | >2000 |
| 122c | $OCH_2CH_3$ | Ph-C≡C— | $OCH(4-CH_3)Ph$ | d ($10^{-4}$) | 17 ± 3% ($10^{-4}$) | 0.110 ± 0.033 | >1000 |
| 122d | $OCH_2CH_3$ | Ph-C≡C— | $OCH(4-CF_3)Ph$ | 32 ± 3% ($10^{-4}$) | 15 ± 1% ($10^{-4}$) | 0.0177 ± 0.0015 | >5000 |
| 122e | $OCH_2CH_3$ | Ph-C≡C— | $OCH_2(3-I)Ph$ | 14 ± 1% ($10^{-4}$) | 19 ± 7% ($10^{-4}$) | 0.0937 ± 0.0333 | >1000 |
| 122f | $OCH_2CH_3$ | Ph-C≡C— | $OCH(3-NO_2)Ph$ | 28 ± 2% ($10^{-4}$) | d ($10^{-4}$) | 0.00858 ± 0.00426 | >11,000 |
| 122g | $OCH_2CH_3$ | Ph-C≡C— | $OCH(4-NO_2)Ph$ | 29 ± 2% ($10^{-4}$) | d ($10^{-4}$) | 0.00269 ± 0.00096 | >37,000 |
| 123 | $OCH_2CH_3$ | Ph-C≡C— | $OCH_2Ph$-4-CO—$NH(CH_2)_2NH_2$ | | | 0.01 | |
| 124 | $OCH_2CH_2CH_3$ | Ph-C≡C— | $OCH_2Ph$ | 27 ± 7% ($10^{-4}$) | 16 ± 2% ($10^{-4}$) | 0.0682 ± 0.0149 | >1400 |
| 125 | $OCH_2CH_3$ | Ph-C≡C— | $O(CH_2)_2Ph$ | d ($10^{-4}$) | d ($10^{-4}$) | 0.146 ± 0.012 | >1000 |
| 126 | $OCH_2CH_3$ | Ph-C≡C— | $O(CH_2)_3Ph$ | d ($10^{-4}$) | d ($10^{-4}$) | 0.0757 ± 0.0258 | >1300 |
| 127 | $OCH_2CH_3$ | Ph-C≡C— | $OC(CH_3)_3$ | 25.3 ± 2.7 | 27 ± 5% ($10^{-4}$) | 3.10 ± 0.64 | 8.2 |
| 128 | $OCH_2CH_3$ | Ph-C≡C— | $OCH_2CH(OCH_3)Ph(R)$ | 8.58 ± 1.34 | 33 ± 6% ($10^{-4}$) | 1.72 ± 0.45 | 5.0 |
| 129 | $OCH_2CH_3$ | Ph-C≡C— | $O(CH_2)_2Si(CH_3)_3$ | 18.8 ± 5.4 | 18 ± 5% ($10^{-4}$) | 0.0596 ± 0.0199 | 310 |
| 130a | $OCH_2CH_3$ | Ph-C≡C— | $SCH_2CH_3$ | 53.0 ± 13.6 | 17 ± 3% ($10^{-4}$) | 0.567 ± 0.185 | 93 |
| 130b | $SCH_2CH_3$ | Ph-C≡C— | $OCH_2CH_3$ | 30 | 5.15 ± 1.83 | 0.290 ± 0.082 | ~100 |
| 131 | $OCH_2CH_3$ | Ph-C≡C— | OH | 8.20 ± 0.40 | 16 ± 6% ($10^{-4}$) | d ($10^{-5}$) | <1 |
| 132 | $OCH_2CH_3$ | Ph-C≡C— | $NHCH_2CH_3$ | 16.2 ± 5.6 | 47 ± 2% ($10^{-4}$) | 5.56 ± 1.69 | 2.9 |
| 133 | $OC(CH_3)_3$ | Ph-C≡C— | $OCH_2CH_3$ | 23.1 ± 1.6 | 20 ± 2% ($10^{-4}$) | 1.04 ± 0.22 | 22 |
| 134 | $NHCH_2CH_3$ | Ph-C≡C— | $OCH_2CH_3$ | 65.6 ± 15.1 | 19 ± 6% ($10^{-4}$) | 2.44 ± 0.13 | 27 |
| 135 | $CH_3$ | Ph-C≡C— | $OCH_2CH_3$ | 12.6 ± 1.9 | 17 ± 7% ($10^{-4}$) | 2.27 ± 0.81 | 5.6 |
| 136 | $R_2$–$R_3$ = $(CH_2)_3$ | Ph-C≡C— | $OCH_2CH_3$ | 12.5 ± 1.5 | 22 ± 4% ($10^{-4}$) | 0.443 ± 0.086 | 28 |
| | $R_1$ | | | | | | |
| 137 | $CH_2OCH_3$ | | $O(CH_2)_2Si(CH_3)_3$ | d ($10^{-4}$) | 27 ± 4% ($10^{-4}$) | 170 ± 80 | >1 |
| 138 | $CH_2OCH_2CH_3$ | | $O(CH_2)_2Si(CH_3)_3$ | 13 ± 3% ($10^{-4}$) | 19 ± 5% ($10^{-4}$) | n.d. | |

TABLE 12-continued

Affinities of dihydropyridine derivatives in radioligand binding assays at $A_1$, $A_{2a}$, and $A_3$ receptors.[a-e]

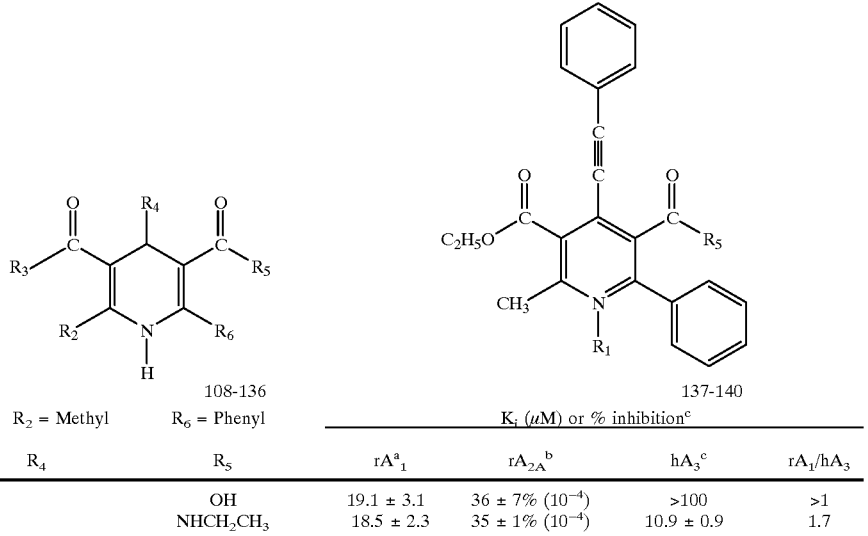

| | | | | 108-136 | | 137-140 | |
| | | $R_2$ = Methyl | $R_6$ = Phenyl | | $K_i$ ($\mu$M) or % inhibition[c] | | |
| Compound | $R_3$ | $R_4$ | $R_5$ | $rA^a_1$ | $rA_{2A}{}^b$ | $hA_3{}^c$ | $rA_1/hA_3$ |
|---|---|---|---|---|---|---|---|
| 139 | $CH_2OCH_2CH_3$ | | OH | 19.1 ± 3.1 | 36 ± 7% ($10^{-4}$) | >100 | >1 |
| 140 | $CH_2OCH_2CH_3$ | | $NHCH_2CH_3$ | 18.5 ± 2.3 | 35 ± 1% ($10^{-4}$) | 10.9 ± 0.9 | 1.7 |

[a]Displacement of specific [$^3$H] R-PIA binding in rat brain membranes, expressed as $K_i$ ± S.E.M. in $\mu$M (n = 3–5), or as a percentage of specific binding displaced at the indicated concentration (M).
[b]Displacement of specific [$^3$H] CGS 21680 binding in rat striatal membranes, expressed as $K_i$ ± S.E.M. in $\mu$M (n = 3–6), or as a percentage of specific binding displaced at the indicated concentration (M).
[c]Displacement of specific [$^{125}$I] AB-MECA binding at human $A_3$ receptors expressed in HEK cells, in membranes, expressed as $K_i$ ± S.E.M. in $\mu$M (n = 3–4).
[d]Displacement of ≦10% of specific binding at the indicated concentration (M).

EXAMPLE 28

This Example illustrates a method of synthesis and resolution of diastereomers of certain 1,4-dihydropyridines. The chemical synthesis and resolution are outlined in FIGS. 9A–9B. Characterization of the 1,4-dihydropyridines derivatives is set forth in Table 13.

Figure 9A:
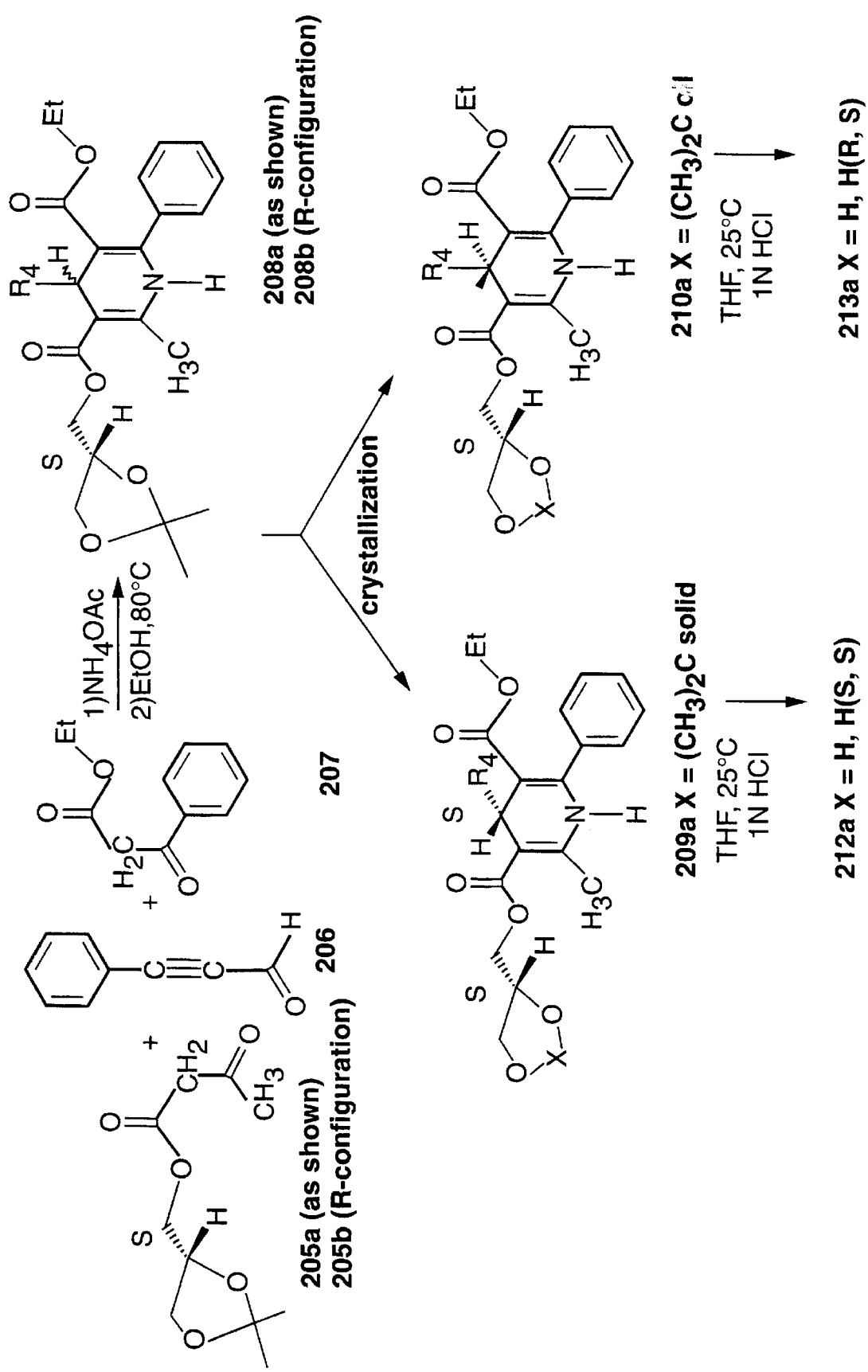
FIG. 9A depicts a part of the reaction scheme for the synthesis of a diastereomeric pair of a 5-ester substituted 1,4-dihydropyridine.

In order to synthesize a diastereomeric pair for resolution, the Hantzsch reaction was carried out using a chiral β-ketoester derived from a protected glycerol moiety (205, FIG. 9A). This intermediate consisted of an acetoacetate ester of (S)-(+)-2,2-dimethyl-1,3-dioxolane-4-methanol), of which the S-enantiomer, 205a, is shown in FIG. 9A. This β-ketoester and the other components of the reaction to form the 4-phenylethynyl-6-phenyl-1,4-dihydropyridine derivative. Thus, 205a, propiolaldehyde, 206, and a benzoylacetoacetate ester, 207, were dissolved in ethanol and refluxed overnight. Proton NMR in deuterated chloroform showed the isolated, gummy product, 208a, to be a 1:1 mixture of S, S and R, S-diastereomers. The signals from each of the two ester α-methylene groups were well resolved in the spectrum and separated by 0.1 ppm. The signals from the 4-H of the diastereomers were separated by 0.03 ppm. Subsequent resolution of the enantiomers (below) and addition of a chiral shift reagent verified that these peaks corresponded to pure diastereomers.

Crystallization of the racemic mixture 208a from methanol provided a pure diastereoisomer of this 4-phenylethynyl-6-phenyl-1,4-dihydropyridine derivative. This isomer was shown by X-ray crystallography to be of the S, S configuration. The remaining isomer was obtained from the mother liquor as an oil and was shown by $^1$H-NMR to be pure. The $^1$H-NMR resonances of the two separate isomers with and without the lanthanide shift reagent Eu(FOD) [see JACS, 1980, 102, 5903] were catalogued and are shown in Table 13. Each of the isolated isomers was shown to be a pure diastereomer and with the peaks of the other isomer not visible in the spectrum. Without EuFOD the 4-H and a methylene resonances were downfield in the R,S vs the S,S isomer. EuFOD (4 mg/mL) caused a downfield shift of all of the resonances. In each case the resonances of the S,S isomer were shifted downfield to a greater degree in the presence of the NMR shift reagent. For example, the signals from the 4-H were shifted by EuFOD by >0.7 ppm in the S,S isomer and by only 0.3 ppm in the R,S isomer. Thus, in the presence of EuFOD this important resonance was separated by 0.4 ppm between the two diastereomers. The reasonances of the two ester α-methylene groups, which were the best resolved in the spectrum measured in the absence of EuFOD, in the presence of EuFOD were separated by ~0.3 ppm.

To establish the absolute configuration at the C4 position of compound 210a an x-ray crystallographic structure was determined. Small needles of 210a were grown by vapor diffusion from methanol/water solution. X-Ray diffraction studies were performed with a Siemens P4 diffractometer (MoKα radiation). Crystals of 210a are monoclinic (P2$_1$) with lattice parameters a=11.059(2) Å, b=8.212(2)Å, c=15.629(3) Å, β=104.46(1)°; and Z=2.

The carbonyl groups were in the cis/cis oreintation, which is consistent with findings for other 1,4-dihydropyridines, in which the 4-position substituent is not highly hindered.

Figure 9B:
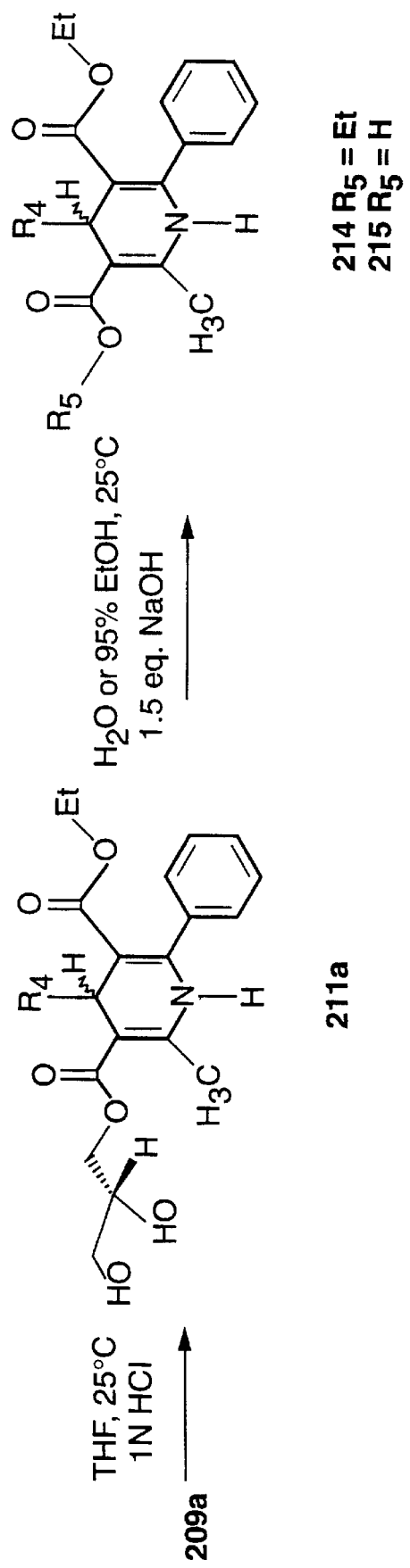
FIG. 9B depicts another part of the reaction scheme for the synthesis of a diastereomeric pair of a 5-ester substituted 1,4-dihydropyridine.

The 2,2-dimethyl-1,3-dioxolane moiety also served as a protected form of a diol, 211a obtained following deprotection in HCl/THF (FIG. 9B). This diol showed a selective reactivity vs the 5-ethyl ester in basic transesterfication reactions. The 3-ethyl ester, 214, was obtained in this manner using sodium hydroxide in 95% ethanol. The resolved diastereomers 209a and 210a were also deprotected separately, to give 212a and 213a. These diols were then tested for biological activity. The results obtained are set forth in Table 14.

TABLE 13

Chemical shifts of diastereomeric 1,4-dihydropyridine derivatives in proton NMR.[a]

| Resonance | Chemical shift (ppm from TMS)[a] | | | |
|---|---|---|---|---|
| | 209a | 209a + EU(fod)$_3$ | 210a | 210a + Eu(fod)$_3$ |
| 2-CH$_3$ | 2.37 | 2.59 | 2.37 | 2.49 |
| 4-H | 5.10 | 5.83 | 5.13 | 5.43 |
| 3-OCH$_2$ | 4.26 | 4.79 | 4.36 | 4.46 |
| 5-OCH$_2$ | 3.99 | 4.47 | 4.09 | 4.19 |
| N—H | 5.90 | 6.03 | 5.88 | 5.94 |

[a]in CDcl$_3$, in the presence or absence of 4 mg/mL Eu(fod)$_3$ (europium tris(6,6,7,7,8,8,8,-heptafluoro2,2-dimethyl-3,5-octanedionate)). The dihydropryidines were dissolved at a concentration of 5 mg/mL.

TABLE 14

Affinities of 1,4 dihydropyridine derivatives in radioligand binding assays at $A_1$, $A_{2a}$, and $A_3$ receptors.[a–e]

| Compound | R$_3$ | chirality at 4-position | R$_5$ | K$_i$ ($\mu$M) or % inhibition[a] | | | |
|---|---|---|---|---|---|---|---|
| | | | | rA$_1$[a] | rA$_{2A}$[b] | hA$_3$[c] | rA$_1$/hA$_3$ |
| 101 | OCH$_2$CH$_3$ | racemic | OCH$_2$Ph | 40.1 ± 7.5 | d (10$^{-4}$) | 0.0314 ± 0.0028 | 1300 |
| 209a | (S-dioxolane-CH$_2$O-) | S | OCH$_2$CH$_3$ | 32 ± 4% (10$^{-4}$) | d (10$^{-4}$) | 1.31 ± 0.57 | >70 |
| 210a | (S-dioxolane-CH$_2$O-) | R | OCH$_2$CH$_3$ | 16.4 ± 3.1 | d (10$^{-4}$) | 0.426 ± 0.133 | 38 |
| 212a | (S-diol-CH$_2$O-) | S | OCH$_2$CH$_3$ | 6.83 ± 0.20 | d (10$^{-4}$) | 0.65 | 11 |
| 213a | (S-diol-CH$_2$O-) | R | OCH$_2$CH$_3$ | 14.8 ± 1.0 | 39 ± 8% (10$^{-4}$) | 0.52 | 28 |
| | OCH$_2$CH$_3$ | racemic | OCH$_2$CH$_3$ | 11.0 ± 0.1 | 26 ± 12% (10$^{-4}$) | 0.0766 ± 0.0151 | 140 |

TABLE 14-continued

Affinities of 1,4 dihydropyridine derivatives in radioligand binding assays at $A_1$, $A_{2a}$, and $A_3$ receptors.[a-e]

| Compound | $R_3$ | chirality at 4-position | $R_5$ | $rA^a_1$ | $rA_{2A}{}^b$ | $hA_3{}^c$ | $rA_1/hA_3$ |
|---|---|---|---|---|---|---|---|
| | (dioxolane-CH₂- structure, R) | racemic | $OCH_2Ph$ | | | | |
| | $OCH_2CH_3$ | racemic | $OCH_2(4-CF_3)Ph$ | | | | |
| | $OCH_2CH_3$ | racemic | $OCH_2CH(OCH_3)$-Ph (R) | 8.58 ± 1.34 | 33 ± 6% ($10^{-4}$) | 1.72 ± 0.45 | 5.0 |

[a]Displacement of specific [$^3$H] R-PIA binding in rat brain membranes, expressed as $K_i$ ± S.E.M. in $\mu$M (n = 3–5), or as a percentage of specific binding displaced at the indicated concentration (M).
[b]Displacement of specific [$^3$H] CGS 21680 binding in rat striatal membranes, expressed as $K_i$ ± S.E.M. in $\mu$M (n = 3–6), or as a percentage of specific binding displaced at the indicated concentration (M).
[c]Displacement of specific [$^{125}$I] AB-MECA binding at human $A_3$ receptors expressed in HEK cells, in membranes, expressed as $K_i$ ± S.E.M. in $\mu$M (n = 3–4).
[d]Displacement of ≤10% of specific binding at the indicated concentration (M).
[e]values taken from van Rhee et al.[16] or from Jiang et al.[16]

EXAMPLE 29

This Example illustrates the synthetic methodology adapted to prepare the 5-N-acyl derivatives of triazoloquinazolines. CGS15943 refers to compound 144 wherein $R_1$ and $R_2$ are hydrogen.

General Procedure for Preparation of 5-N-acyl Derivatices of CGS15943

Method A (Symmetrical Anhydride)

To a stirred solution of CGS15943 (10 mg, 0.035 mmole), anhydride (0.105 mmole) and dimethylaminopyridine (0.5 mg, 0.004 mmole) in 1.5 ml of anhydrous DMF was added triethylamine (73 $\mu$l, 0.525 mmole) at room temperature. The mixture was stirred for 48 h and then evaporated to dryness under reduced pressure. The residue was purified by preparative silica gel TLC ($CH_2Cl_2$-MeOH, 50:1~75:1) to afford the desired compounds, 145–148, and 150, 151.

Method B (Acid Chloride)

To a stirred solution of CGS15943 (10 mg, 0.035 mmole), anhydrous pyridine (40 $\mu$l, 0.5 mmole) in 1.5 ml of anhydrous $CH_2Cl_2$ was added acylchloride (0.105 mmole) at 0° C. The mixture was stirred at room temperature for 24–48 h., then treated with same procedure as Method A for purification of desired compounds, (149, 153, and 160–162)

Method C (Carbodiimide)

A solution of CGS15943 (10 mg, 0.035 mmole), acid (0.210 mmole), 1-(3-dimethylaminopropyl)-3-ethylcarbodiimide (41 mg, 0.201 mmole), 1-hydroxybenzotriazole (28 mg, 0.210 mmole), dimethylaminopyridine (0.5 mg, 0.004 mmole) and triethylamine (74 $\mu$l, 0.530 mmole) in 2 ml of anhydrous DMF/$CH_2Cl_2$ (1:1 v/v) was stirred at room temperature for 48 h. The mixture was treated with same procedure as Method A for purification of desired compounds (152,154)

5-Acetylamino-9-chloro-2-(2-furyl)[1,2,4]triazolo[1,5-c]quinazoline (145)

2.78(3H,s), 6.63–6.65(1H,m), 7.30(1H, d, J=2.9), 7.68 (1H, broad s), 7.73(1H, dd, J=1.9, 8.8), 7.86(1H, d, J=8.8), 8.48(1H, d, J=2.9), 8.99(NH, broads)

9-Chloro-2-(2-furyl)-5-propionylamino[1,2,4]triazolo[1,5-c]quinazoline (146)

1.34(3H,t, J=7.81,7.82), 3.10(2H,q, J=7.81, 6.8, 7.82), 6.63–6.65(1H, m), 7.31(1H, d, J=3.91), 7.68(1H, d, J=1.96), 7.73(1H, dd, J=1.96, 8.79), 7.88(1H, d, J=8.79), 8.48(1H, d, J=1.96), 9.01(NH, broad s)

5-Butyrylamino-9-chloro-2-(2-furyl)[1,2,4]triazolo[1,5-c]quinazoline (147)

1.10(3H, t, J=7.42, 7.28), 1.84–1.91 (2H, m), 3.03(2H, t, J=7.42, 7.27), 6.63–6.65(1H,m), 7.31(1H, d, J=3.43), 7.68 (1H, d, J=1.78), 7.73(1H, dd, J=2.34, 8.8), 7.88(1H, d, J=8.8), 8.48(1H, d, J=2.33), 8.97(NH, broad s)

9-Chloro-2-(2-furyl)-5-pentanoylamino[1,2,4]triazolo[1,5-c]quinazoline (148)

1.01(3H,t, J=6.84, 7.82), 1.48–155(2H, m), 1.77–1.85 (2H, m), 3.05(2H, t, J=7.82, 6.83), 6.63–6.65(1H, m), 7.31

(1H, d, J=2.93), 7.68(1H, broad s), 7.73(1H, dd, J=1.95, 8.79), 7.88(1H, d, J=8.80), 8.48(1H, d, J=2.93), 8.98(NH, broad s)

9-Chloro-2-(2-furyl)-5-trimethylacetylamino[1,2,4]triazolo [1,5-c]quinazoline (149)

1.47(9H, s), 6.63–6.65(1H, m), 7.31(1H, d, J=3.44), 7.68–7.69(1H, m), 7.74(1H, dd, J=2.47, 8.93), 8.01(1H, d, J=8.93), 8.49(1H, d, J=2.48), 9,39(NH, broad s)

5-[(tert.-Butoxycarbonyl)amino]-9-chloro-2-(2-furyl)[1,2,4]triazolo[1,5-c]quinazoline (150)

1.63(9H, s), 6.65–6.66(1H, m), 7.35(1H, d, J=3.47), 7.69 (1H, broad s), 7.74(1H, dd, J=2.60, 8.90), 8.01(1H, d, J=8.90), 8.49(1H, d, J=2.59), 8.56(NH, broad s)

5-Benzoylamino-9-chloro-2-(2-furyl)[1,2,4]triazolo [1,5-c]quinazoline (151)

6.64–6.66(1H, m), 7.35(1H, d, J=2.93), 7.61–7.68(3H, m), 7.68–7.70(1H, m), 7.77(1H, dd, J=1.96, 8.79), 8.04–8.10 (3H,m), 8.52(1H, d, J=1.95), 9.75(NH, broad s)

9-Chloro-2-(2-furyl)-5-(4'-iodobenzoyl)amino[1,2,4] triazolo [1,5-c]quinazoline (152)

6.64–6.66(1H, m), 7.30–7.36(3H, m), 7.70(1H, broad s), 7.77(1H, dd, J=1.95, 10.74), 7.92–8.10(2H, broad m), 8.39 (1H, m), 8.52(1H, d, J=1.96), 9.62(NH, broad s)

9-Chloro-2-(2-furyl)-5-phenylacetylamino[1,2,4]triazolo [1,5-c]quinazoline (153)

4.38(2H, s), 6.62–6.65(1H, m), 7.24–7.26(1H, m), 7.35–7.44(5H, m), 7.67–7.68(1H,m), 7.74(1H, dd, J=2.20, 9.04), 7.93(1H, d, J=8.79), 8.49(1H, m), 9.10(NH, broad s)

5-[[4-tert.-Butoxycarbonyl)amino]butyryl]amino-9-chloro-2-(2-furyl)[1,2,4]triazolo[1,5-c]quinazoline (154)

1.44(9H, s), 2.03(2H, pen, J=6.83), 3.13(2H, t, J=6.83, 7.33), 3.32((2H, q, J=6.35), 4.81(NH, broad s), 6.63–6.65 (1H, m), 7.27–7.32(1H, m), 7.67–7.68(1H, m), 7.71–7.75 (1H, m), 7.91(1H, d, J=8.79), 8.48(1H, d, J=1.96), 9.15(NH, broad s)

5-Amino-2-[2-5-bromofuryl)]-9-chloro[1,2,4]triazolo[1,5-c]quinazoline (157)

A solution of 266(0.01 g, 0.026 mmole) and N-bromosuccinimide (0.005 g. 0.028 mmole) in 2 ml of AcOH/CHCl₃ (1:1) was stirred for 1 h at room temperature. The mixture was poured into 10 ml of sat. NaHCO₃ solution and the product was extracted with 10 ml of CHCl₃ three times. The combined CHCl₃ solution was washed with brine, dried over anhydrous Na₂SO₄ and evaporated to driness under reduced pressure. The residue was purified by preparative silical gel TLC (CHCl₃-MeOH, 80:1) to afford 2-[2-5-Bromofuryl)]-5-[(tert.-butoxycarbonyl)amino]-9-chloro[1,2,4]triazolo[1,5-c]quinazoline (0.012 g, 99%) as a white solid: MS (CI, NH₃) 466(M⁺+1); ¹H-NMR (CDCl₃) 6.58 (1H, d, J=3.58), 7.29(1H, d, J=3.59), 7.73(1H, dd, J=2.28, 8.79), 7.98(1H, d, J=9.01), 8.46(1H, d, J=2.28), 8.53(NH, broad s). To a solution of this compound in 2 ml of CH₂Cl₂ was added TFA (0.05 ml, 0.67 mmole) and stirred for 2 h at room temperature. The reaction mixture was treated with same work-up procedure above. A preparative silical gel TLC (n-Hex.-ChCl₃-MeOH, 1:1:0.1) of the crude product gave 273(4.5 mg, 48%) as a white solid: MS (CI, NH₃) 366(M⁺+1), 383(M⁺+18); 'H-NMR (CDCl₃) 5.94 (NH₂, broad s), 6.56(1H, d, J=3.80), 7.25(1H, d, J=3.80), 7.63–7.65(2H, m), 8.41(1H, d, J=2.07).

9-Chloro-2-(2-furyl)[1,2,4]triazolo[1,5-c]quinazolin-5-(6H)-one (158)

A solution of CGS15943 (0.075 g, 0.263 mmole) in 8.0 ml of AcOH and 2.0 ml of H₂O in a sealed tube was heated for 72 h at 100° C. The solution was coevaporated with toluene under reduced pressure and the residue was purified by preparative silical gel TLC (CHCl₃-MeOH, 15:1) to afford 274 (0.065 g, 86%) as a white solid: mp>310° C.; MS (CI NH₃) 287(M⁺+1), 304(M⁺+18); 'H-NMR (DMSO-d₆) 6.73–6.74(1H, m), 7.26(1H, d, J=3.47), 7.46(1H, d, J=8.79), 7.77(1H, dd, J=2.49, 8.90), 7.97(1H, S), 8.16(1H, d, J=2.48), 12.47(NH, S).

9-Chloro-2-(2-furyl)[1,2,4]triazolo[1,5-c]quinazolin-6-propyl-5-one (159)

To a suspension of 158 (0.021 g, 0.073 mmole) in 2 ml of anhydrous THF was added a suspension of NaH (6 mg, 60% in mineral oil, prewashed with n-hexane, 0.15 mmole) in 2 ml of anhydrous THF followed by HMPA (0.32 ml, 12 mmole under N₂ atmosphere at room temperature. The mixture was stirred vigorously for 30 min. H₂ gas evolved. 1-Bromopropane (28 μl, 0.3 mmole) was added and the reaction mixture was refluxed for 6 h. After cooling, the precipitate was removed by filtration through a small volume of silical gel bed and the filtrate was evaporated. The residue was purified by preparative silical gel TLC (n-Hex.-EtOAc, 2:1) to afford 159 (0.012 g. 50%) as a white solid: 1H-NMR (CDCl₃) 1.11(3H, t, J=7.49, 7.48), 1.85–1.93(2H, m), 4.35(2H, t, J=8.03, 7.49), 6.60–6.61(1H, m), 7.32(1H, d, J-3.36), 7.37(1H, d, J=9.34), 7.66(1H, broad s), 7.68(1H, dd, J=2.39, 9.01), 8.52(1H, d, J=2.50)

EXAMPLE 30

This Example illustrates the affinities of certain triazoloquinazolines. The affinities were determined in radioligand binding assays, and the results are set forth in Tables 15–16.

TABLE 15

Affinities of 2-(2-furyl) [1,2,4]triazolo[1,5-c]quinazoline derivatives in radioligand binding assays at $A_1$, $A_{2a}$, and $A_3$ receptors[a–e]

(144-157)  (158-159)

| Compound | $R_1$ | $R_2$ | $R_3$ | $rA_1$ | $rA_{2A}$ | $hA_3$ | $rA_1/hA_3$ | $rA_{2A}/hA_1$ |
|---|---|---|---|---|---|---|---|---|
| 144 CGS15943 | H | H | | 21 ± 3[d] | 3.3 ± 1.7[d] | 13.8 ± 2.4 | | |
| 145 | COCH$_3$ | H | | 52.2 ± 2.6 | | 13.9 ± 2.5 | 3.8 | |
| 146 | COCH$_2$CH$_3$ | H | | 283 ± 42 | 106 ± 30 | 7.66 ± 3.03 | 40 | 14 |
| 147 | CO(CH$_2$)$_2$CH$_3$ | H | | 32.5 ± 9.4 | 4 | 14.6 ± 2.8 | 2.2 | |
| 148 | CO(CH$_2$)$_3$CH$_3$ | H | | 28.9 ± 3.7 | 16 | 21.5 ± 6.2 | 1.3 | |
| 149 | COC(CH$_3$)$_3$ | H | | 205 ± 20 | 60 | 244 ± 6 | 0.84 | |
| 150 | CO—OC(CH$_3$)$_3$ | H | | 190 ± 16 | 92.0 ± 8.0 | 82.5 ± 23.3 | 2.3 | 1.1 |
| 151 | CO-Ph | H | | 665 ± 82 | 349 ± 42 | 4.05 ± 1.39 | 164 | 86 |
| 152 | CO-(3-I-Ph) | H | | 200 | 200 | 23.8 ± 5.2 | | |
| 153 | COCH$_2$-Ph | H | | 305 ± 51 | 52.0 ± 8.8 | 0.63 ± 0.25 | | |
| 154 | CO(CH$_2$)$_3$NH-Boc | H | | 91.3 ± 13.2 | 173 | 32 | | |
| 155 | CO(CH$_2$)$_3$NH$_2$ | H | | 11.3 ± 2.4 | 14 | 15.2 ± 6.6 | | |
| 156 | CO-Ph | Br | | >1000 | >1000 | 856 ± 156 | | |
| 157 | H | Br | | 1,570[d] | 531[d] | 54.0 ± 13.1 | | |
| 158 | | | H | 3,000 | 4,000 | 260 ± 87 | | |
| 159 | | | (CH$_2$)$_2$CH$_3$ | 2,000 | | 1.810 ± 720 | | |

[a]Displacement of specific [$^3$H] PIA binding in rat brain membranes, expressed as $K_i$ ± S.E.M. in nM (n = 3–5).
[b]Displacement of specific [$^3$H] CGS 21680 binding in rat striatal membranes, expressed as $K_i$ ± S.E.M. in nM (n = 3–6).
[c]Displacement of specific [$^{125}$I] AB-MECA binding at human $A_3$ receptors expressed in HEK cells, in membranes, expressed as $K_i$ ± S.E.M. in nM (n = 3–4), or as a percentage of specific binding displaced at the indicated concentration (M).
[d]IC$_{50}$ values from Francis et al., J. Med. Chem., 31, pp. 1014–1020 (1988).

TABLE 16

Affinities of triazoloquinazoline derivatives in radioligand binding assays at $A_1$, $A_{2a}$, and $A_3$ receptors.[a–e]

| Compound | $R_1$ | $R_2$ | $rA_1$ | $rA_{2A}$ | $hA_3$ | $rA_1/hA_3$ | $rA_{2A}/hA_1$ |
|---|---|---|---|---|---|---|---|
| 160 | CO—CH$_2$CH$_2$Ph | H | 45.2 ± 7.5 | 28.3 ± 10.3 | 29.7 ± 7.7 | | |
| 161 | CO—CH=CHPh | H | 282 ± 71 | 59.8 ± 13.4 | 60.0 ± 6.3 | | |
| 162 | CO—CH$_2$-Ph-4-NO$_2$ | H | 28 | | 8.70 ± 0.97 | | |

TABLE 16-continued

Affinities of triazoloquinazoline derivatives in radioligand binding assays at $A_1$, $A_{2a}$, and $A_3$ receptors.[a–e]

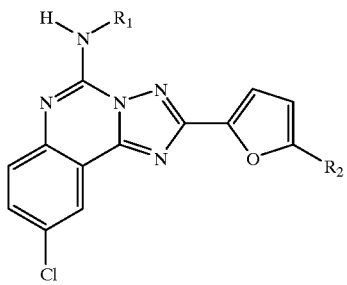

| | | | | | $K_i$ ($\mu$M) or % inhibition[c] | | | |
|---|---|---|---|---|---|---|---|---|
| Compound | $R_1$ | $R_2$ | $rA_1$ | $rA_{2A}$ | $hA_3$ | $rA_1/hA_3$ | $rA_{2A}/hA_1$ | |
| 163 | COCH$_2$-Ph-4-NH$_2$ | H | 30 | 20 | 4 | | | |
| 164 | COCH$_2$-Ph-3-I-4-NH$_2$ | H | | | 1 | | | |

[a]Displacement of specific [$^3$H] R-PIA binding in rat brain membranes, expressed as $K_i$ ± S.E.M. in nM (n = 3–5).
[b]Displacement of specific [$^3$H] CGS 21680 binding in rat striatal membranes, expressed as $K_i$ ± S.E.M. in nM (n = 3–6).
[c]Displacement of specific [$^{125}$I] AB-MECA binding at human $A_3$ receptors expressed in HEK cells, in membranes, expressed as $K_i$ ± S.E.M. in nM (n = 3–4), or as a percentage of specific binding displaced at the indicated concentration (M).

EXAMPLE 31

This Example illustrates the utility of the adenosine receptor antagonists of the present invention in the killing of cancer cells.

Reagents:

HL-60 and U-937 cells were obtained from the ATCC (Bethesda, Md.). RPMI 1640 medium and fetal bovine serum were obtained from Gibco BRL (Gaithersburg, Md.). IB-MECA (2-[4-[92-carboxyethyl)phenyl]ethylamino]-5'-N-ethylcarboxamidoadenosine) and Cl-IB-MECA (N$^6$-(3-iodobenzyl)-2-chloro-adenosine-5'-N-methyluronamide) were obtained from RBI (Natick, Mass.) through the NIMH Synthesis Program. The $A_3$ selective adenosine antagonists 101 and 153 were synthesized using procedures described earlier. L-249313 (6-carboxymethyl-5,9-dihydro-9-methyl-2-phenyl-[1,2,4]triazolo[5,1-a][2,7]-naphthyridine) supplied as the mesylate salt was the gift of Dr. Marlene Jacobson at Merck (West Point, Pa.). The Apoptosis Detection System was from Promega (Madison, Wis.), and the anti-bak antibody was from Calbiochem (La Jolla, Calif.). Rhodamine (TRITC)-conjugated AffiniPure Goat Anti-mouse IgG (H+L) is from Jackson ImmunoResearch Laboratories, Inc. Chromonycin $A_3$ was purchased from Sigma Chemical (St. Louis, Mo.).

Cell cultures and preparations:

The HL-60 cells were maintained in RPMI 1640 supplemented with 10% fetal calf serum, 100 units/ml penicillin, 100 mg/ml streptomycin and 2 mM L-glutamine. The cells were split every third day, and 2 days before each experiment cultures were diluted to 2×10$^5$ cells/ml. For analysis of DNA content, aliquots of 2 ml were placed into 12-well flat-bottomed plates (Costar, Cambridge, Mass., U.S.A.) containing 2~6 $\mu$l test-compound solutions at defined concentrations or 6 $\mu$l DMSO (diluting medium). Live cell counting was carried out using 0.1% trypan blue.

DNA content analysis by flow cytometry:

Cells were fixed by adding ~10$^7$ cells suspended in 1 ml of PBS of 1 ml 80% ethanol at –20° C. and stored for 48–120 hrs. After the cells were washed twice with PBS, the cells were stained with 20 mg/ml chromomycin A3 dissolved in PBS containing 2 mM MgCl$_2$ by incubation in subdued light (30 min; 4° C.). The cells were then analyzed using a FACScan flow cytometer (Becton Dickinson, Mountain View, Calif.).

In situ hybridization:

Cells were fixed by immersing slides in 4% methanol-free formaldehyde in PBS at pH 7.4, 4° C., for 25 min. Fixed cells were permeabilized in 0.2% Triton® X-100 in PBS at 4° C. for 5 min. After preincubation with 100 $\mu$M Promega equilibration buffer for 10 min at room temperature, the cells were covered with 50 $\mu$l TdT incubation buffer and a coverslip and maintained at 37° C. for 60 min inside the dark humidified chamber to protect from dry and direct light. In order to stop the reaction, the coverslip was removed and the slides were immersed in 2×SSC for 15 min at room temperature. The cells were restained by propidium iodide 1 $\mu$g/ml in PBS for 15 min. After every step, the cells were rinsed 2–3 times with fresh PBS for 5 min each. Finally, the glass slides were sealed with nail polish. The slides were stored at 4° C. in the dark.

Immunofluorescent staining:

Cells were fixed as following steps: 10 min with 1% formalin in PBS, 5 min with 10° C. methanol and 2 min with ice cold acetone, then permebilized with 0.1% Nonidet P-40 for 20 min. After the preparation, the specimens were incubated step by step: 10% goat serum in PBS for 20 min, mouse monoclonal anti-bak antibody (5 $\mu$g/ml PBS-BSA) for 60 min, Rhodamine (TRITC)-conjugated AffiniPure Goat Anti-mouse IgG (H+L) in PBS-BSA for 60 min. The specimens were washed 3–5 times with PBS after every step. The glass slides were stored at 4° C. in the dark.

Figure 10A:
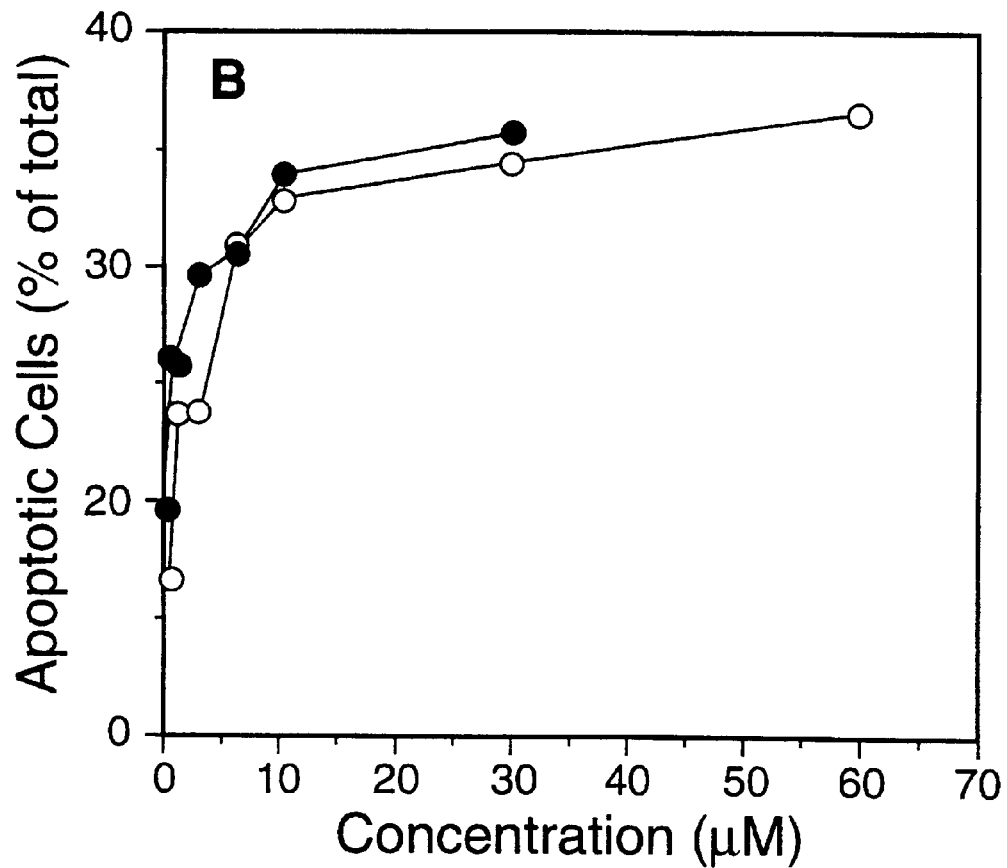
FIG. 10A depicts the percentage of HL-60 apoptotic cells (vertical axis) as a function of the concentration (horizontal axis) of $A_3$ adenosine receptor agonists IB-MECA (°) and Cl-IB-MECA (•), as determined by fluorescent cell sorting (flow cytometric DNA analysis).
Figure 10B:
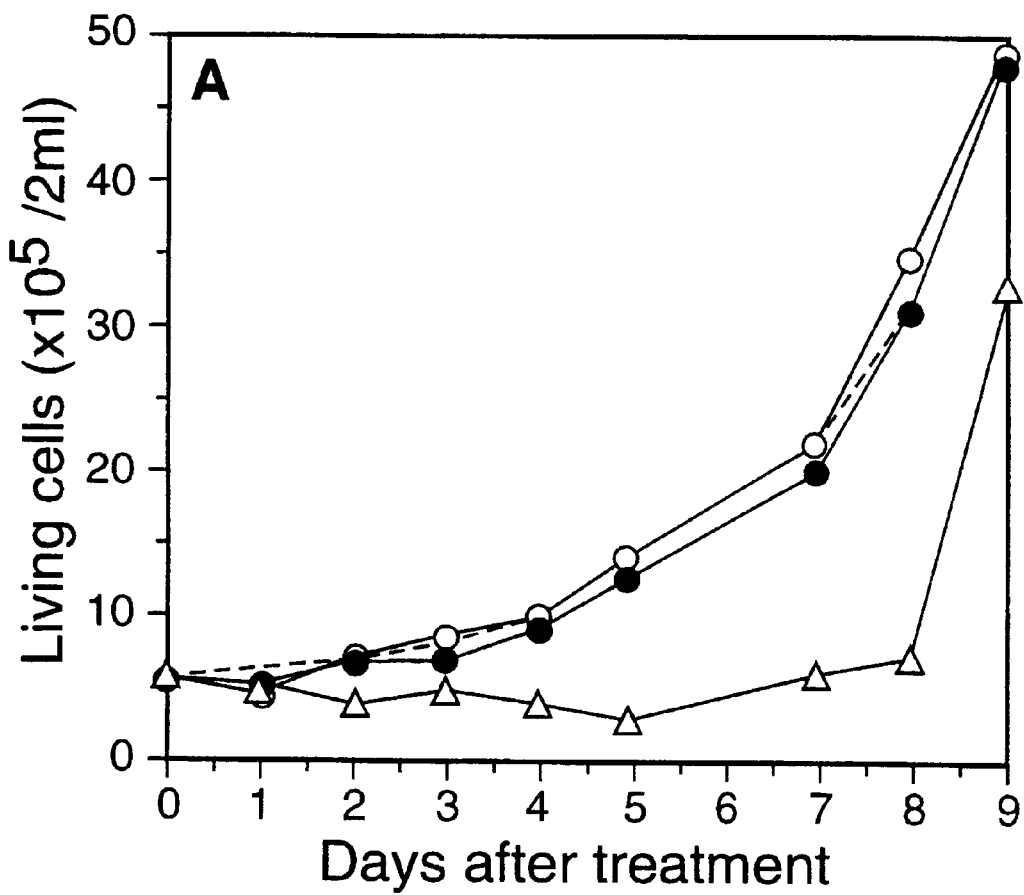
FIG. 10B depicts the percentage of U-937 apoptotic cells (vertical axis) as a function of the concentration (horizontal axis) of A₃ adenosine receptor agonists IB-MECA (°) and Cl-IB-MECA (•), as determined by fluorescent cell sorting (flow cytometric DNA analysis).

Flow cytometry data obtained are set forth in FIGS. 10A and 10B and indicate that high concentrations ($\geq \mu$M) of the $A_3$ receptor agonists, IB-MECA and Cl-IB-MECA, caused apoptosis in HL-60 promyelocytic leukemia cells. A similar response was observed in U-937 histiocytic lymphoma cells.

In FIG. 10, the percent of apoptotic cells was estimated from the percent cells having hypodiploid DNA content in a DNA frequency histogram. Upon incubation with the agonist for 48 hours, a plateau in the percent of apoptotic cells within the range of 30–50% of total was observed beginning at approximately 10 μM for either agonist in HL-60 (FIG. 10A) and in U-937 cells (FIG. 10B).

The more highly $A_3$ receptor selective agonist, Cl-IB-MECA, at lower concentrations ($\leq 1$ μM) did not significantly promote apoptosis, as determined using flow cytometry (FIGS. 10A–B), or general cell death, as determined using trypan blue staining (FIGS. 11A–D). In the latter assay, cell death was studied in HL-60 cells (FIGS. 11A–B) and in U-937 cells (FIGS. 11C–D) over a time course of 9 days. Cells in culture receiving no drug treatment proliferated geometrically until nearly the end of the experiment. In the presence of 0.01 or 1.0 μM Cl-IB-MECA alone, no deviation from this growth curve was observed.

Figure 11A:
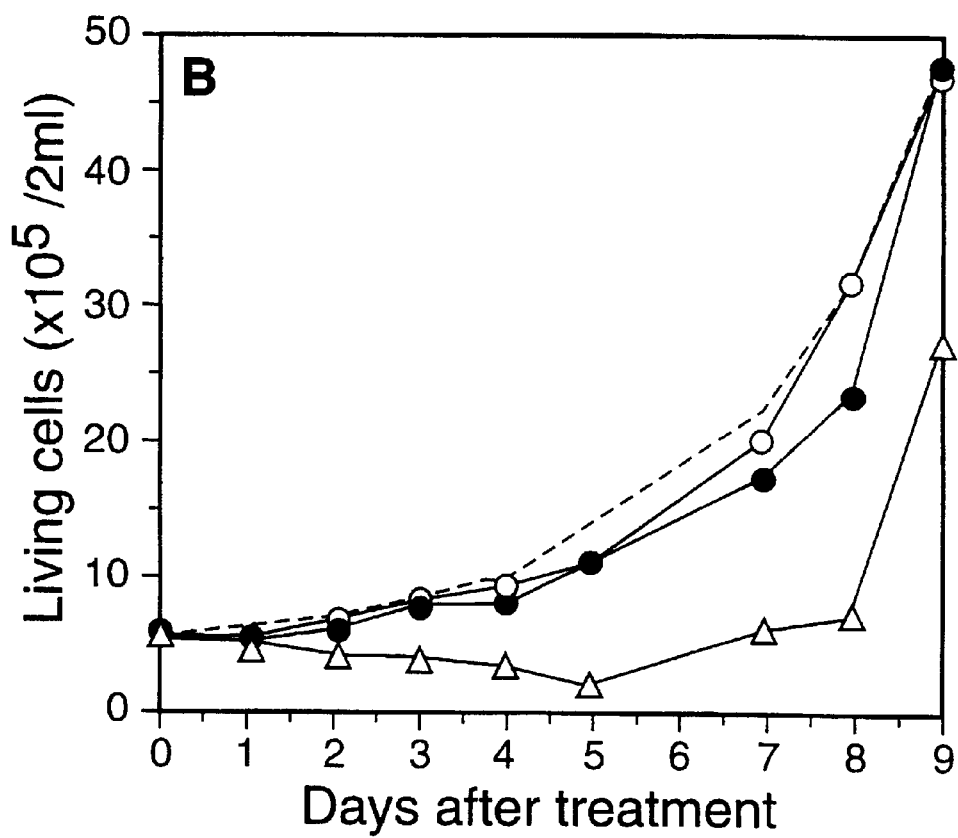
FIG. 11A depicts the number of living HL-60 cells (vertical axis) as a function of the concentration (horizontal axis) of A₃ denosine receptor antagonist and a low concentration of Cl-IB-MECA. The antagonist was compound 101.
Figure 11B:
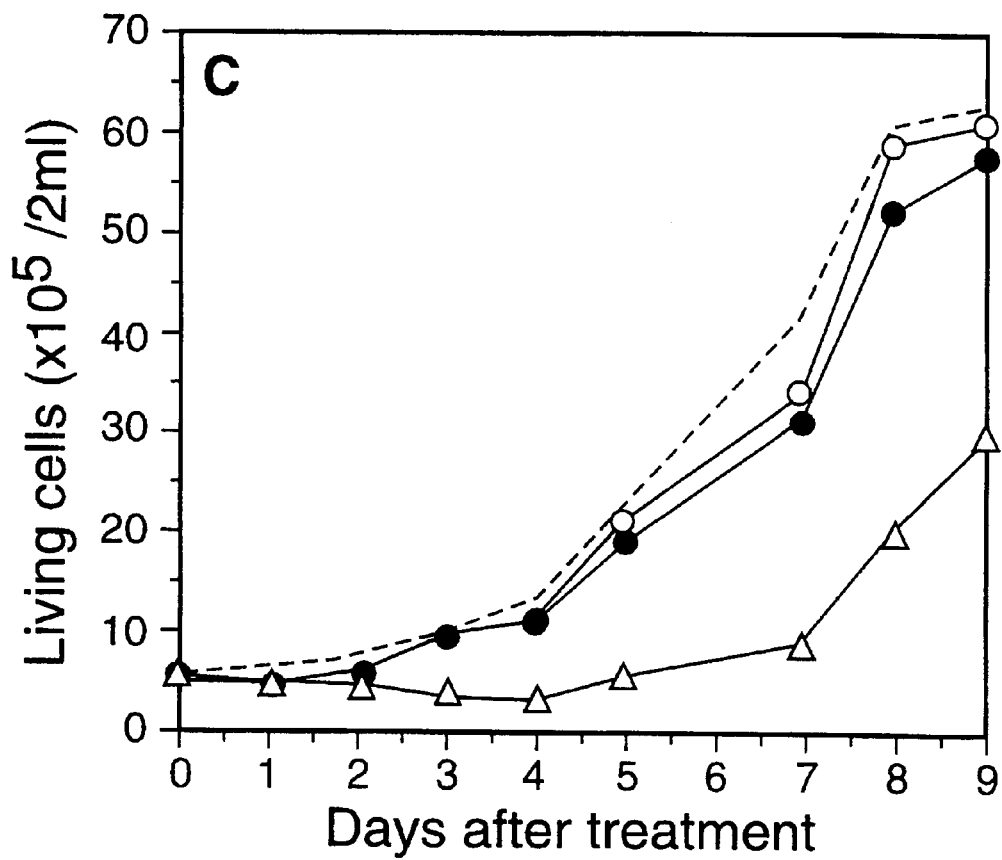
Figure 11C:
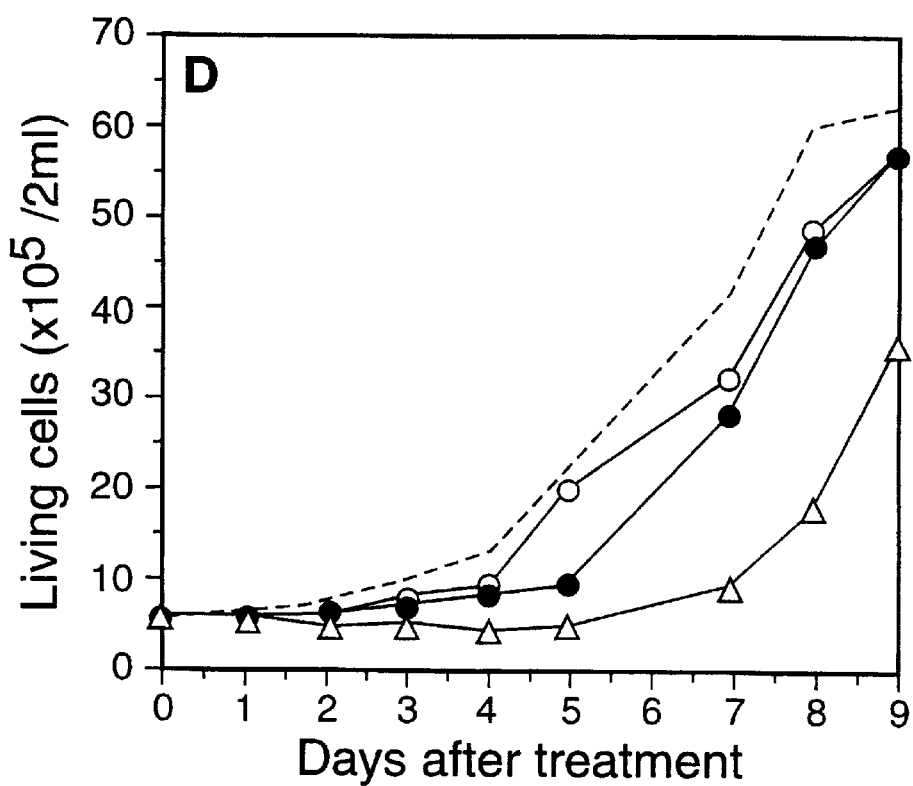
Figure 11D:
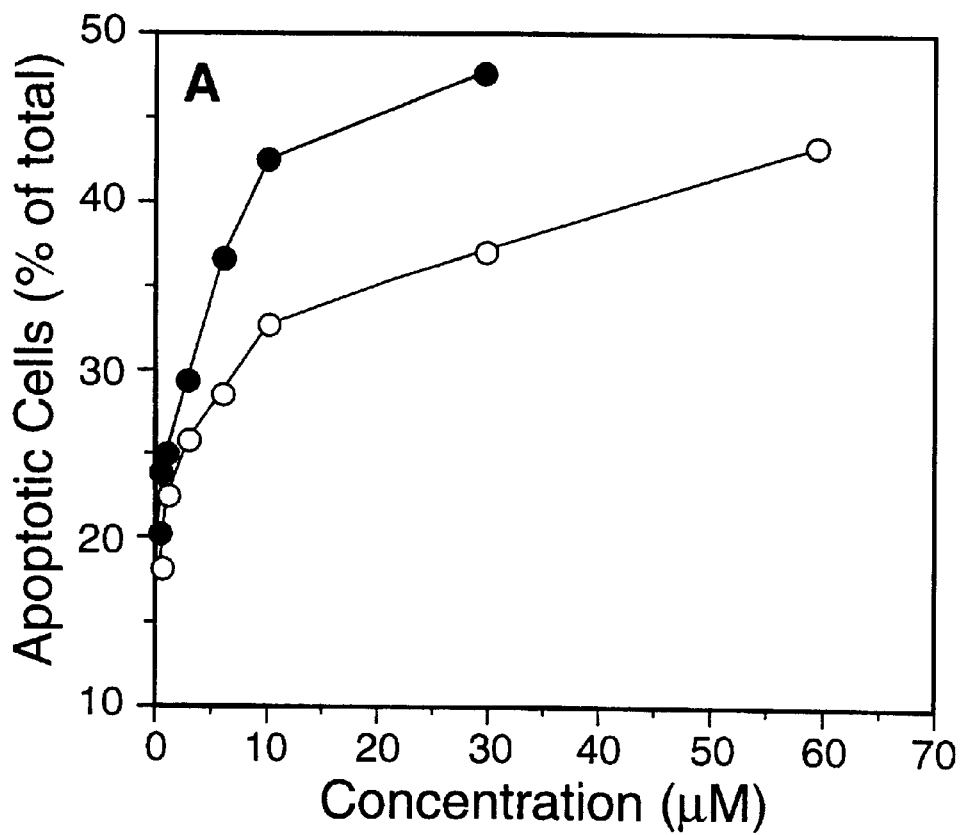

Cl-IB-MECA at a concentration of 20 or 40 μM caused death of >90% of HL-60 cells in culture after 4 days followed by a very slow increase in cell number. U-937 cells were slightly less sensitive to this agonist, with 40 μM Cl-IB-MECA required to obtain a similar effect. Either of the selective $A_3$ receptor antagonists, 101 or L-249313, at a concentration of 0.5 μM, alone caused a general inhibition of proliferation of cells during this time period. An initial reduction in the number of cells during the first 4–5 days was followed by highly impeded growth. However, in the presence of both an $A_3$ antagonist and either 0.01 or 1.0 μM Cl-IB-MECA, the growth curves were nearly coincident with control curves. Thus, this $A_3$ agonist at sublethal concentrations, including the very low concentration of 10 nM, reversed the impairment of cell proliferation induced by either of the selective antagonists in both HL-60 cells (FIGS. 11A–B) and U-937 cells (FIGS. 11C–D).

The evidence that DNA strand breaks, characteristic of apoptosis, are induced by the $A_3$ antagonists was obtained using in situ end-labeling in-situ of fragmented nuclear DNA by terminal deoxynucleotidyl transferase (TUNEL method, Cooke, H., *Trends in Biotech.*, 10, 23 (1992)), which incorporates a fluorescent label at the 3'-ends. In HL-60 and U-937 cells (Table 15), a 24 h incubation with either 50 nM 101 or 50 nM L-249313 produced widespread (approximately 30–40% of the cells present) fluorescent labeling of apoptotic cells. In the control cultures and in those treated with 10 nM Cl-IB-MECA alone, spontaneous apoptosis occured in only 5–7% of the cells (Table 17). Coadministration of 10 nM Cl-IB-MECA with either antagonist suppressed the increase in apoptotic cells. The reversal of antagonist-induced apoptosis by the agonist is similar to that observed for the growth curves, except that both agonist and antagonist were applied at lower concentrations. High concentrations of Cl-IB-MECA (30 μM) also caused extensive DNA fragmentation in both HL-60 and U-937 cells, as indicated by the TUNEL method, with approximately 50% labeling.

The mechanism of the apoptosis observed in response to either $A_3$ agonists was investigated. Expression of the apoptosis-inducing protein bak in response to the adenosine receptor ligands was studied using immunofluorescent methods (Towbin et al., *Proc. Natl. Acad. Sci. USA*, 76, 4350–4354 (1979)). Bak labeling was absent in control HL-60 cells or U-937 cells, but was present in the cells treated for 24 hours with either L-249313 or 101. The expression of bak protein was also induced in both HL-60 cells and U-937 cells using the triazoloquinazoline $A_3$ antagonist 153 (10 nM). Cl-IB-MECA, at 30 μM but not concentrations $\leq 1$ μM, induced a significant level of expression of bak in both HL-60 cells and U-937 cells.

Various other cell lines were investigated for the expression of bak in response to the $A_3$ agonist. Cl-IB-MECA at 10 μM was found to induce the expression of bak in MCF7 breast adenocarcinoma cells and 1321N astrocytoma cells, but not in U373 astrocytoma cells, so the upregulation of bak expression by $A_3$ agonists appears to be a widespread but not universal phenomenon.

These results suggest that both $A_3$ agonists and antagonists, by virtue of regulating programmed cell death, may have usefulness in treating diseases either in which cytotoxicity is undesirable, such as neurodegeneration, or desirable, such as cancer and inflammation. The level of agonist or antagonist should be carefully balanced to obtain the desired effect on the cells, e.g., death or protection.

TABLE 17

Percentage of apoptotic cell in HL60 and U937 after 48 hour treatment with $A_3$ antagonists (50 nM) and a low concentration of Cl-IB-MECA (10 nM), determined using end-labeling in-situ of fragmented nuclear DNA by terminal deoxynucleotidyl transferase. Both small and large cells that stained positive were counted manually.

| Cell | Control | Cl-IB MECA | 101 | 101 +Cl-IB-MECA | L-249313 | L-249313 +Cl-IB-MECA |
|---|---|---|---|---|---|---|
| HL-60 | 6.8 | 7.1 | 39.7 | 11.6 | 31.2 | 12.0 |
| U937 | 5.1 | 5.6 | 27.3 | 10.4 | 30.8 | 10.9 |

EXAMPLE 32

This Example illustrates the utility of the present inventive compounds in preserving neurons in stroke suffered by an animal.

Female Mongolian gerbils received bilateral 10 min. carotid occlusion, followed by injection 15 min. later with 100 μg/kg of the $A_3$ adenosine receptor antagonist, compound 101, in a vehicle of emulpher/saline (1:4). Control gerbils were injected with saline. The survival of the animals was followed as a function of time after ischemia. The animals injected with the antagonist showed high survival rates: 90% after 7 days and 80% after 90 days. The control group survival rates were 50% after 7 days and 20% after 90 days.

The number of intact neurons was also counted. After 7 days of ischemia, the animals injected with the antagonist had 75% intact neurons, and, after 90 days, the number of intact neurons was 90%, thereby indicating that neurons that are damaged under the influence of the antagonist are capable of recovery. The control group rates were 35% after 7 days and 90 days.

These data show that the $A_3$ adenosine receptor antagonist both protects and enhances the chances of survival among neurons that are damaged and, unless exposed to the drug, would eventually die.

EXAMPLE 33

This Example illustrates the bronchoconstricting effect of $A_3$ adenosine receptor agonists and the utility of $A_3$ adenosine receptor antagonists in combating the bronchconstricting effect of $A_3$ adenosine receptor agonists.

Adenosine receptors have been implicated in the bronchoconstriction (BC) in allergic asthma. It was found that after selectively blocking $A_1$ receptors by diphenyl cyclopentyl xanthine, IB-MECA, an $A_3$ agonist, induced a dosedependent BC in allergic rabbits. It was also found that after blocking both $A_1$ and $A_2$ specific binding sites with a xanthine amino congener, $A_3$ specific binding was displaced by APNEA, an $A_3$ agonist. These results confirmed that $A_3$ adenosine receptor agonist can cause BC.

It was further found that $A_3$ adenosine receptor antagonists can combat the BC induced by the $A_3$ agonist.

New Zealand white pasteurella free rabbit litter mates were exposed to $A_3$ adenosine agonist APNEA, IB-MECA, or Cl-IB-MECA and the percent change in dynamic compliance ($C_{dyn}$) was measured as a function of the adenosine dose using known procedures. Ali et al., *J. Pharmacol. & Exper. Therap.*, 268, 1328–1334 (1993). Allergy was induced in the rabbits using dust mites.

Figure 12:
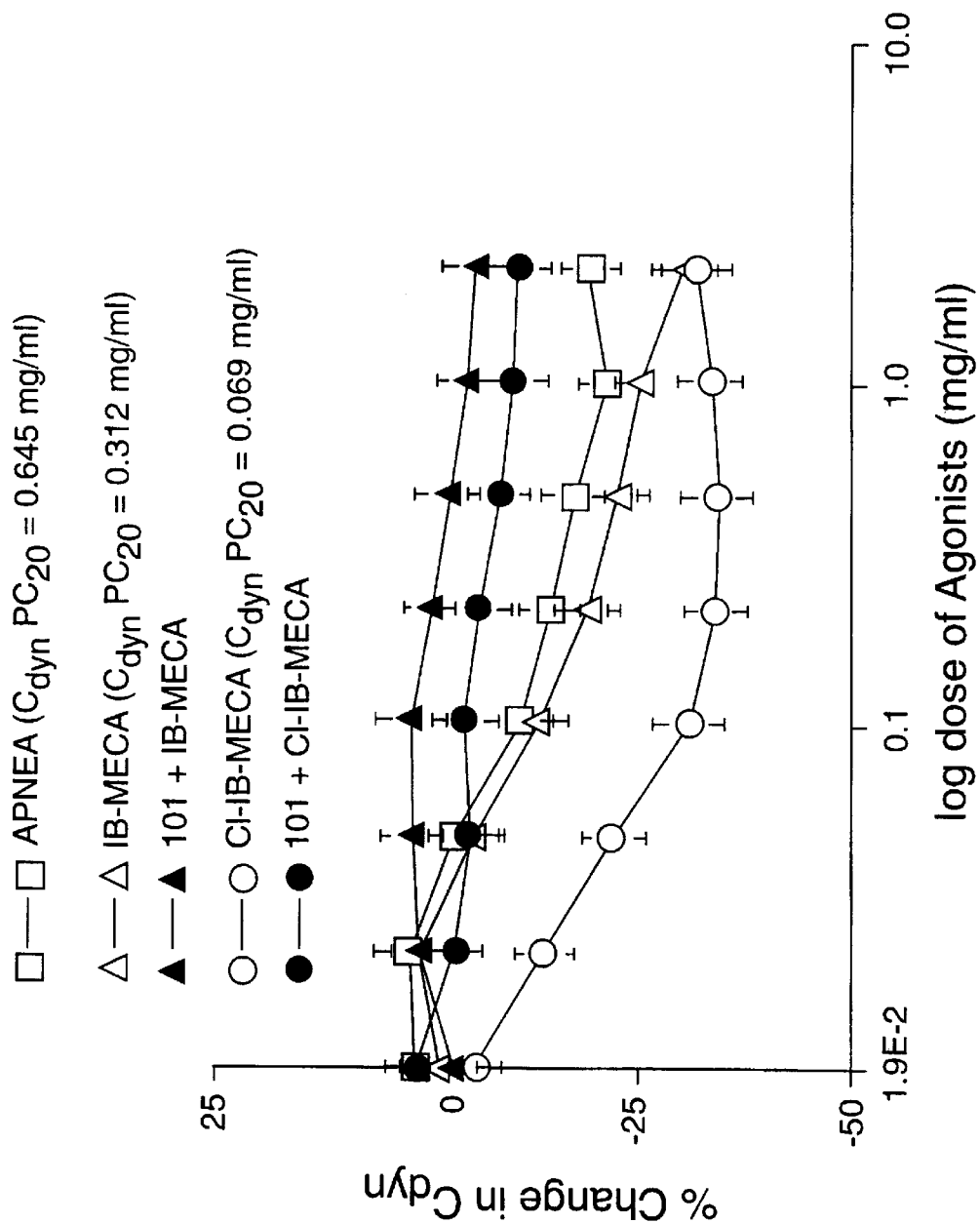
FIG. 12 depicts the percent change in dynamic compliance ($C_{dyn}$, vertical axis) of rabbit lung as a function of the adenosine agonist concentration using Cl-IB-MECA (o), APNEA ( ), or IB-MECA (Δ). (•) represents percent change in $C_{dyn}$ as a result of exposure to compound 101 plus Cl-IB-MECA and (▲) represents percent change in $C_{dyn}$ as a result of exposure to compound 101 plus IB-MECA.

The results obtained are set forth in FIG. 12 (open symbols) and show that the adenosine agonist causes the Cdyn to decrease, which is an indication of bronchoconstriction. However, when an adenosine antagonist, compound 101, was co-administered with the agonist, the percent change in dynamic compliance was much reduced (filled symbols). The antagonist was administered at a constant dose of $10^{-5}$ M through a 2 minute aerosilization, followed by a 15 minute wait before the measurement of dynamic compliance. The results confirm that the $A_3$ adenosine receptor antagonist is effective in combating inflammatory disorders such as asthma.

All of the references cited herein including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula

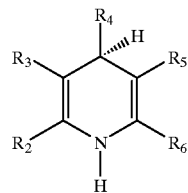

or a pharmaceutically acceptable salt thereof, wherein $R_2$ is a $C_1$–$C_6$ alkyl; $R_6$ is phenyl which may be further substituted with $C_1$–$C_6$ alkyl, halo, nitro, furyl, or thienyl; $R_3$ is selected from the group consisting of $C_1$–$C_6$ alkyl, $C_1$–$C_6$ alkyloxycarbonyl, aryl $C_1$–$C_6$ alkyloxycarbonyl, $C_1$–$C_6$ alkylthiocarbonyl, $C_1$–$C_6$ alkylaminocarbonyl, and $C_1$–$C_6$ alkyloxy $C_1$–$C_6$ alkylcarbonyl, or $R_3$ together with $R_2$ forms a ring having 2–4 methylene groups, and $C_1$–$C_6$ alkenyloxycarbonyl; $R_4$ is selected from the group consisting of $C_1$–$C_6$ alkyl, aryl $C_2$–$C_6$ alkenyl, $C_1$–$C_6$ alkylamino, $C_1$–$C_6$ alkyl silyl $C_1$–$C_6$ alkyloxy, aryl, heterocyclic, aryl $C_1$–$C_6$ alkyl, phenylacetylenyl which may be further substituted with nitro, $C_1$–$C_6$ alkyl, hydroxy, halo, amino, carboxy, $C_1$–$C_6$ alkoxy, $C_1$–$C_6$ haloalkyl, or $C_1$–$C_6$ alkylamino, and styryl whose phenyl ring may be further substituted with one or more substituents selected from the group consisting of halo, nitro, amino, hydroxy, $C_1$–$C_6$ alkyl, cyano, $C_1$–$C_6$ alkyloxy, $C_1$–$C_6$ alkyloxycarbonyl, $C_1$–$C_6$ alkylcarbonyl, hydroxy $C_1$–$C_6$ alkyl, $C_1$–$C_6$ haloalkyl, carboxy, aminocarbonyl, $C_1$–$C_6$ alkylamino, amino $C_1$–$C_6$ alkyl, and $C_1$–$C_6$ dialkylamino; and $R_5$ is selected from the group consisting of $C_1$–$C_6$ alkyloxycarbonyl, aryl $C_1$–$C_6$ alkyloxycarbonyl, $C_1$–$C_6$ alkyloxy $C_1$–$C_6$ alkyloxycarbonyl, aryloxy $C_1$–$C_6$ alkyloxycarbonyl, aryl $C_1$–$C_6$ alkyloxy $C_1$–$C_6$ alkyloxycarbonyl, silyl $C_1$–$C_6$ alkyloxycarbonyl, $C_1$–$C_6$ alkylthio, hydroxy, and $C_1$–$C_6$ alkylamino, wherein the aryl moiety of said $R_5$ may be further substituted with $C_1$–$C_6$ alkyl, $C_1$–$C_6$ halo alkyl, trifluoromethyl, halo, nitro, $C_1$–$C_6$ amino alkyl, $C_1$–$C_6$ aminoalkylamino, or $C_1$–$C_6$ amino alkylamino carbonyl; wherein the aryl moiety of said $R_3$, $R_4$, $R_5$, and $R_6$ is independently phenyl or naphthyl.

2. The compound of claim 1, wherein $R_4$ is selected from the group consisting of $C_1$–$C_6$ alkyl, aryl $C_2$–$C_6$ alkenyl, $C_1$–$C_6$ alkylamino, $C_1$–$C_6$ alkyl silyl $C_1$–$C_6$ alkyloxy, aryl, aryl $C_1$–$C_6$ alkyl, a heterocyclic selected from the group consisting of furyl, thienyl, pyridyl, and benzofuryl, phenylacetylenyl which may be further substituted with nitro, $C_1$–$C_6$ alkyl, hydroxy, halo, amino, carboxy, $C_1$–$C_6$ alkoxy, $C_1$–$C_6$ haloalkyl, or $C_1$–$C_6$ alkylamino, and styryl whose phenyl ring may be further substituted with one or more substituents selected from the group consisting of halo, nitro, amino, hydroxy, $C_1$–$C_6$ alkyl, cyano, $C_1$–$C_6$ alkyloxy, $C_1$–$C_6$ alkyloxycarbonyl, $C_1$–$C_6$ alkylcarbonyl, hydroxy $C_1$–$C_6$ alkyl, $C_1$–$C_6$ haloalkyl, carboxy, aminocarbonyl, $C_1$–$C_6$ alkylamino, amino $C_1$–$C_6$ alkyl, and $C_1$–$C_6$ dialkylamino.

3. The compound of claim 2, wherein $R_2$ is methyl.

4. The compound of claim 3, wherein $R_3$ is selected from the group consisting of methoxycarbonyl and ethoxycarbonyl.

5. The compound of claim 4, wherein $R_6$ is phenyl.

6. The compound of claim 5, wherein $R_4$ is selected from the group consisting of $C_1$–$C_3$ alkyl, phenylacetylenyl which may be further substituted with nitro $C_1$–$C_6$ alkyl, hydroxy, halo amino, carboxy $C_1$–$C_6$ alkoxy, $C_1$–$C_6$ haloalkyl, or $C_1$–$C_6$ alkylamino, and styryl whose phenyl ring may be further substituted with one or more substituents selected from the group consisting of halo, nitro, amino, hydroxy, $C_1$–$C_6$ alkyl, cyano, $C_1$–$C_6$ alkyloxy, $C_1$–$C_6$ alkyloxycarbonyl, $C_1$–$C_6$ alkylcarbonyl, hydroxy $C_1$–$C_6$ alkyl, $C_1$–$C_6$ haloalkyl, carboxy, aminocarbonyl, $C_1$–$C_6$ alkylamino, amino $C_1$–$C_6$ alkyl, and $C_1$–$C_6$ dialkylamino.

7. The compound of claim 6, wherein $R_5$ is selected from the group consisting of methyoxycarbonyl, ethoxycarbonyl, methoxyethoxycarbonyl, and benzyloxycarbonyl.

8. The compound of claim 7, wherein $R_4$ is phenyl substituted with one or more substituents selected from the group consisting of nitro, trifluoromethyl, methoxy, hydroxy, and methylenedioxy.

9. The compound of claim 8, wherein $R_5$ is selected from the group consisting of methoxycarbonyl, ethoxycarbonyl, and methoxyethoxycarbonyl.

10. The compound of claim 9, wherein $R_3$ is ethoxy, $R_4$ is phenylacetylenyl or trans-styryl, or phenylacetylenyl or trans-styryl which is substituted with methoxy or nitro groups, $R_5$ is ethoxy or benzyloxy, and $R_6$ is phenyl, which may be further substituted with nitro, halo, methyl, or methoxy group.

11. The compound of claim 10, wherein $R_3$ is ethoxycarbonyl, $R_4$ is phenylacetylenyl, $R_5$ is benzyloxycarbonyl, and $R_6$ is phenyl.

12. The compound of claim 11, wherein said compound is a mixture of diastereomers having R or S configuration at the 4-position.

13. The compound of claim 11, wherein said compound is an R-enantiomer.

14. The compound of claim 11, wherein said compound is an S-enantiomer.

15. The compound of claim 11, wherein said compound is modified as an acetoacetate ester of a (+) or (−) 2,2-dialkyl 1,3-dioxolane-4-methanol or a (+) or (−) alkyleneglycol methanol.

16. A pharmaceutical composition comprising a pharmaceutically acceptable carrier and a compound of claim 1.

17. A method of treating a mammal comprising selectively blocking the $A_3$ adenosine receptor of a mammal by administering to said mammal a compound of claim 1.

18. A method of cerebroprotecting a mammal comprising selectively blocking the $A_3$ adenosine receptor of the mammal by administering to the mammal an effective amount of a compound of claim 1.

19. A compound of the formula

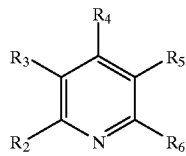

or pharmaceutically acceptable salts thereof, wherein $R_2$ is selected from the group consisting of hydrogen and $C_1$–$C_6$ alkyl; $R_3$ is selected from the group consisting of hydrogen and $C_1$–$C_6$ alkyloxycarbonyl; $R_4$ is selected from the group consisting of $C_1$–$C_6$ alkyl, phenyl $C_2$–$C_6$ alkenyl, phenyl $C_2$–$C_6$ alkynyl, aryl, and aryl substituted with one or more substituents selected from the group consisting of nitro and $C_1$–$C_6$ alkyloxy; $R_5$ is selected from the group consisting of hydrogen, $C_1$–$C_6$ alkyloxycarbonyl, and aryl $C_1$–$C_6$ alkyloxy carbonyl; $R_6$ is selected from the group consisting of hydrogen, aryl, and $C_1$–$C_6$ alkyl; with the proviso that when $R_2$=$R_3$=$R_5$=$R_6$=hydrogen, $R_4$ is not alkyl.

20. A compound of the formula

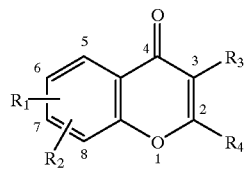

wherein $R_1$ and $R_3$ are selected from the group consisting of hydrogen, hydroxy, $C_1$–$C_6$ alkyloxy, and $C_1$–$C_6$ alkylcarbonyloxy; $R_2$ is selected from the group consisting of hydrogen, hydroxy, $C_1$–$C_6$ alkyloxy, $C_1$–$C_6$ alkylcarbonyloxy, and $C_2$–$C_6$ alkenyloxy, said alkenyloxy together with the carbon atom of the phenyl ring forming an oxygen heterocycle; and $R_4$ is selected from the group consisting of phenyl, styryl, phenylbutadienyl, phenylacetylenyl, and —CH=N-phenyl, and substituted phenyl, styryl, phenylacetylenyl, and phenylbutadienyl, wherein the phenyl ring is substituted with 1 to 5 $C_1$–$C_6$ alkyloxy groups; with the provisos that when $R_3$ is hydrogen, $R_1$ and $R_2$ are neither hydroxy nor alkyloxy; when $R_1$, $R_2$, and $R_3$ are hydrogen, $R_4$ is neither phenyl nor alkyloxyphenyl; when $R_3$ is hydrogen and $R_4$ is phenyl, neither $R_1$ nor $R_2$ is alkylcarbonyloxy; and when $R_3$ is hydroxy or alkyloxy, $R_1$ and $R_2$ are not dihydroxy.

21. A compound of the formula

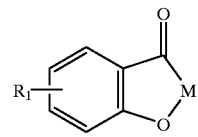

wherein $R_1$ is selected from the group consisting of hydroxy and $C_1$–$C_6$ alkyloxy, and M is a divalent radical selected from the group consisting of —CH(OH)—CH($R_2$)— and —C(OH)=C($R_2$)—, wherein $R_2$ is selected from the group consisting of styryl and phenylacetylenyl.

22. A method of treating a mammal comprising selectively blocking one or more adenosine receptors of said mammal by administering to said mammal at least one compound of the formula

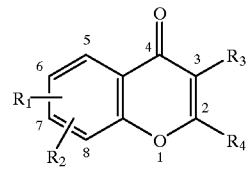

wherein $R_1$ and $R_3$ are selected from the group consisting of hydrogen, hydroxy, $C_1$–$C_6$ alkyloxy, and $C_1$–$C_6$ alkylcarbonyloxy; $R_2$ is selected from the group consisting of hydrogen, hydroxy, $C_1$–$C_6$ alkyloxy, $C_1$–$C_6$ alkylcarbonyloxy, and $C_2$–$C_6$ alkenyloxy, said alkenyloxy together with the carbon atom of the phenyl ring forming an oxygen heterocycle; $R_4$ is selected from the group consisting of phenyl, styryl, phenylbutadienyl, phenylacetylenyl, and —CH=N-phenyl, and substituted phenyl, styryl, phenylacetylenyl, and phenylbutadienyl, wherein the phenyl ring is substituted with 1 to 5 $C_1$–$C_6$ alkyloxy groups; with the provisos that when $R_3$ is hydrogen, $R_1$ and $R_2$ are neither hydroxy nor alkyloxy; when $R_1$, $R_2$, and $R_3$ are hydrogen, $R_4$ is neither phenyl nor alkyloxyphenyl; and when $R_3$ is hydrogen and $R_4$ is phenyl, neither $R_1$ nor $R_2$ is alkylcarbonyloxy.

23. A method of treating a mammal comprising selectively blocking one or more adenosine receptors of said mammal by administering to said mammal at least one compound selected from the group consisting of genistein, (±)dihydrogenistein, sakuranetin, α-naphthoflavone, β-naphthoflavone, amaryllidaceae, oxogalanthine lactam, acetylhaemanthine methiodide, 2,3-methylenedioxy-fluorene-9-one, hematoxylin, and arborinine.

24. A compound of the formula

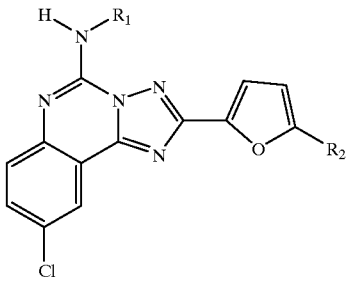

or a pharmaceutically acceptable salt thereof, wherein $R_1$ is selected from the group consisting of $C_1$–$C_6$ alkylcarbonyl, aryl $C_1$–$C_6$ alkylcarbonyl, aryl $C_2$–$C_6$ alkenylcarbonyl, $C_1$–$C_6$ alkyloxycarbonyl, amino $C_1$–$C_6$ alkylcarbonyl, and arylcarbonyl, wherein said aryl may be further substituted with halo, nitro, hydroxy, amino or cyano; and $R_2$ is hydrogen or halogen.

25. A pharmaceutical composition comprising a pharmaceutically acceptable carrier and a compound of claim 19.

26. A pharmaceutical composition comprising a pharmaceutically acceptable carrier and a compound of claim 20.

27. A pharmaceutical composition comprising a pharmaceutically acceptable carrier and a compound of claim 21.

28. A pharmaceutical composition comprising a pharmaceutically acceptable carrier and a compound of claim 24.

29. A method of treating a mammal comprising selectively blocking an adenosine receptor of a mammal by administering to said mammal a compound of claim 19.

30. A method of treating a mammal comprising selectively blocking an adenosine receptor of a mammal by administering to said mammal a compound of claim 20.

31. A method of treating a mammal comprising selectively blocking an adenosine receptor of a mammal by administering to said mammal a compound of claim 21.

32. A method of treating a mammal comprising selectively blocking an adenosine receptor of a mammal by administering to said mammal a compound of claim 24.

33. A method of cerebroprotecting a mammal comprising selectively blocking the $A_3$ adenosine receptor of the mammal by administering to the mammal an effective amount of a compound of claim 19.

* * * * *